US010172889B2

(12) United States Patent
Sokal et al.

(10) Patent No.: US 10,172,889 B2
(45) Date of Patent: Jan. 8, 2019

(54) METHOD FOR PRODUCING ADULT LIVER PROGENITOR CELLS

(71) Applicant: Promethera Biosciences S.A./N.V., Mont-Saint-Guibert (BE)

(72) Inventors: Etienne Sokal, Hoeilaart (BE); Sarah Snykers, Lede (BE); Tuba Baran, Fontaine-l'Eveque (BE); Kris Gellynck, Saint-Gilles (BE)

(73) Assignee: Promethera Biosciences S.A./N.V., Mont-Saint-Guibert (BE)

( * ) Notice: Subject to any disclaimer, the term of this patent is extended or adjusted under 35 U.S.C. 154(b) by 62 days.

(21) Appl. No.: 14/914,983

(22) PCT Filed: Aug. 28, 2014

(86) PCT No.: PCT/EP2014/068317
§ 371 (c)(1),
(2) Date: Feb. 26, 2016

(87) PCT Pub. No.: WO2015/028577
PCT Pub. Date: Mar. 5, 2015

(65) Prior Publication Data
US 2016/0206664 A1 Jul. 21, 2016

Related U.S. Application Data

(60) Provisional application No. 61/870,983, filed on Aug. 28, 2013.

(51) Int. Cl.
*A61K 35/407* (2015.01)
*G01N 33/50* (2006.01)
*C12N 5/071* (2010.01)

(52) U.S. Cl.
CPC .......... *A61K 35/407* (2013.01); *C12N 5/0672* (2013.01); *G01N 33/5023* (2013.01); *G01N 33/5067* (2013.01); *C12N 2501/11* (2013.01); *C12N 2501/12* (2013.01); *C12N 2501/734* (2013.01); *C12N 2533/54* (2013.01)

(58) Field of Classification Search
CPC .............. C12N 5/0672; C12N 2501/11; C12N 2501/12; C12N 2501/734; C12N 2533/54; A61K 35/407; G01N 33/5023; G01N 33/5067
See application file for complete search history.

(56) References Cited

U.S. PATENT DOCUMENTS 7,935,528 B2 * 5/2011 Faris .............................. 435/326
2007/0065520 A1 3/2007 Johansson
2008/0311094 A1 * 12/2008 Sokal et al. ................. 424/93.21

FOREIGN PATENT DOCUMENTS

| EP | 1969118 B1 | 2/2011 |
| WO | WO-2007071339 A1 | 6/2007 |
| WO | WO-2016/030525 A1 | 3/2016 |

OTHER PUBLICATIONS

International Search Report for International Application No. PCT/EP2014/068317, dated Dec. 1, 2014 (4 pages).
Lee et al., "The use of single-pass albumin dialysis to correct severe hyperbilirubinemia in acute Hepatitis A: a case report," The Korean Journal of Nephrology. 29:260-4 (2010).
Scheers et al., "Adult-derived human liver progenitor cells in long-term culture maintain appropriate gatekeeper mechanisms against transformation," Cell Transplant. 21(10):2241-55 (2012).
Sivasubramaniyan et al., "Prospective isolation of mesenchymal stem cells from human bone marrow using novel antibodies directed against Sushi domain containing 2," Stem Cells Dev. 22(13):1944-54 (2013) (12 pages).
Written Opinion for International Application No. PCT/EP2014/068317, dated Dec. 1, 2014 (7 pages).
Allameh et al., "Safety evaluation of stem cells used for clinical cell therapy in chronic liver diseases; with emphasize on biochemical markers," Clin Biochem. 45(6):385-96 (2012) (14 pages).
Alépée et al., "t4 Workshop Report*: State-of-the-art of 3D cultures (organs-on-a-chip) in safety testing and pathophysiology," available in PMC Mar. 8, 2016, published in final edited form as: ALTEX. 31(4):441-77 (2014) (68 pages).
Azuma et al., "Enrichment of hepatic progenitor cells from adult mouse liver," Hepatology. 37(6):1385-94 (2003).
Bale et al., "In vitro platforms for evaluating liver toxicity," available in PMC Sep. 5, 2014, published in final edited form as: Exp Biol Med. 239(9):1180-91 (2014) (23 pages).
Baudoin et al., "Evaluation of seven drug metabolisms and clearances by cryopreserved human primary hepatocytes cultivated in microfluidic biochips," Xenobiotica. 43(2):140-52 (2013) (Abstract only).
Benz et al., "Maintenance of 'stem cell' features of cartilage cell sub-populations during in vitro propagation," J Transl Med. 11:27 (2013) (23 pages).
Bieback, "Platelet lysate as replacement for fetal bovine serum in mesenchymal stromal cell cultures," Transfus Med Hemother. 40(5):326-335 (2013).
Busser et al., "Isolation and characterization of human mesenchymal stromal cell subpopulations: comparison of bone marrow and adipose tissue," Stem Cells Dev. 24(18):2142-57 (2015).
Bühring et al., "Novel markers for the prospective isolation of human MSC," Ann N Y Acad Sci. 1106:262-71 (2007) (11 pages).
Caralt et al., "Liver bioengineering: from the stage of liver decellularized matrix to the multiple cellular actors and bioreactor special effects," Organogenesis. 10(2):250-9 (2014).

(Continued)

*Primary Examiner* — Satyendra K Singh
(74) *Attorney, Agent, or Firm* — Clark & Elbing LLP; Susan M. Michaud

(57) ABSTRACT

Novel adult liver progenitor cells (called H2Stem Cells) have been have been characterized on the basis of a series of biological activities and markers. Methods for producing H2Stem Cells allow providing such cells in the form of adherent cells and three-dimensional cell clusters in suspension that can be differentiated into cells having strong liver-specific activities and/or that can be used for treating liver diseases or for evaluating the efficacy, the metabolism, and/or toxicity of a compound.

14 Claims, 10 Drawing Sheets

(56) References Cited

OTHER PUBLICATIONS

Castilho-Fernandes et al., "Human hepatic stellate cell line (LX-2) exhibits characteristics of bone marrow-derived mesenchymal stem cells," Exp Mol Pathol. 91(3):664-72 (2011) (10 pages).

Cigognini et al., "Engineering in vitro microenvironments for cell based therapies and drug discovery," Drug Discov Today. 18(21-22):1099-108 (2013) (10 pages).

Dan, "Clinical uses of liver stem cells," Methods Mol Biol. 826:11-23 (2011) (Abstract only) (7 pages).

Darwiche et al., "Biology of the adult hepatic progenitor cell: 'ghosts in the machine'," available in PMC Jun. 24, 2011, published in final edited form as: Prog Mol Biol Transl Sci. 97:229-49 (2010) (16 pages).

Egloff et al., "Scale-up of hepatic progenitor cells from multitray stack to 2-D bioreactors," BMC Proceedings. 7(Suppl 6):P61 (2013) (3 pages).

Gerets et al., "Characterization of primary human hepatocytes, HepG2 cells, and HepaRG cells at the mRNA level and CYP activity in response to inducers and their predictivity for the detection of human hepatotoxins," Cell Biol Toxicol. 28(2):69-87 (2012).

Griffiths et al., "Human platelet lysate stimulates high-passage and senescent human multipotent mesenchymal stromal cell growth and rejuvenation in vitro," Cytotherapy. 15(12):1469-83 (2013) (16 pages).

Gómez-Lechón et al., "Evaluation of cytochrome P450 activities in human hepatocytes in vitro," Methods Mal Biol. 806:87-97 (2011) (Abstract only) (4 pages).

Halladay et al., "An 'all-inclusive' 96-well cytochrome P450 induction method: measuring enzyme activity, mRNA levels, protein levels, and cytotoxicity from one well using cryopreserved human hepatocytes," J Pharmacol Toxicol Methods. 66(3):270-5 (2012) (6 pages).

Herrera et al., "Isolation and characterization of a stem cell population from adult human liver," Stem Cells. 24(12):2840-50 (2006).

Hoffmann et al., "Analysis of drug metabolism activities in a miniaturized liver cell bioreactor for use in pharmacological studies," Biotechnol Bioeng. 109(12):3172-81 (2012).

Hook, "Stem cell technology for drug discovery and development," Drug Discov Today. 17(7-8):336-42 (2012).

Kabel, "Bleeding disorders: insights into aetiology, pathogenesis, diagnosis and management," Int J Hematol Dis. 1(1):22-6 (2014).

Khuu et al., "In vitro differentiated adult human liver progenitor cells display mature hepatic metabolic functions: a potential tool for in vitro pharmacotoxicological testing," Cell Transplant. 20(2):287-302 (2011).

Lau et al., "The estimation of paracetamol and its major metabolites in both plasma and urine by a single high-performance liquid chromatography assay," J Pharm Biomed Anal 12(12):1563-72 (1994) (Abstract only).

Lee et al., "Liver extracellular matrix providing dual functions of two-dimensional substrate coating and three-dimensional injectable hydrogel platform for liver tissue engineering," Biomacromolecules. 15(1):206-18 (2014) (Abstract only).

Lin et al., "The application of engineered liver tissues for novel drug discovery," Expert Opin Drug Discov. 10(5):519-40 (2015) (22 pages).

Lu et al., "A novel 3D liver organoid system for elucidation of hepatic glucose metabolism," available in PMC Jan. 31, 2014, published in final edited form as: Biotechnol Bioeng. 109(2):595-604 (2012) (21 pages).

Lübberstedt et al., "HepaRG human hepatic cell line utility as a surrogate for primary human hepatocytes in drug metabolism assessment in vitro," J Pharmacol Toxicol Methods. 63(1):59-68 (2011).

Massie et al., "Cryopreservation of encapsulated liver spheroids for a bioartificial liver: reducing latent cryoinjury using an ice nucleating agent," Tissue Eng Part C Methods. 17(7):765-74 (2011) (Abstract only).

Masuda et al., "A novel marker of human endometrial mesenchymal stem-like cells," Cell Transplant. 21(10):2201-14 (2012).

Meng, "Three-dimensional culture of hepatocytes for prediction of drug-induced hepatotoxicity," Expert Opin Drug Metab Toxicol. 6(6):733-46 (2010). (Abstract only).

Mitaka et al., "Characterization of hepatic-organoid cultures," Drug Metab Rev. 42(3):472-81 (2010) (Abstract only).

Miyazaki et al., "Isolation of a bone marrow-derived stem cell line with high proliferation potential and its application for preventing acute fatal liver failure," Stem Cells. 25(11):2855-63 (2007).

Muscari et al., "Priming adult stem cells by hypoxic pretreatments for applications in regenerative medicine," J Biomed Sci. 20:63 (2013) (13 pages).

Najar et al., "Immune-related antigens, surface molecules and regulatory factors in human-derived mesenchymal stromal cells: the expression and impact of inflammatory priming," Stem Cell Rev. 8(4):1188-98 (2012) (abstract only) (22 pages).

Najar et al., "Impact of different mesenchymal stromal cell types on T-cell activation, proliferation and migration," Int Immunopharmacol. 15(4):693-702 (2013) (Abstract only).

Najimi et al., "Adult-derived human liver mesenchymal-like cells as a potential progenitor reservoir of hepatocytes?" Cell Transplant 16(7):717-28 (2007).

Parveen et al., "An update on hepatic stem cells: bench to bedside," Curr Pharm Biotechnol. 12(2):226-30 (2011). (Abstract only).

Pilz et al., "Human term placenta-derived mesenchymal stromal cells are less prone to osteogenic differentiation than bone marrow-derived mesenchymal stromal cells," Stem Cells Dev. 20(4):635-46 (2011) (Abstract only).

Raicevic et al., "Influence of inflammation on the immunological profile of adult-derived human liver mesenchymal stromal cells and stellate cells," Cytotherapy. 17(2):174-85 (2015).

Russo et al., "Stem cells in liver failure," Best Pract Res Clin Gastroenterol. 26(1):35-45 (2012) (Abstract only).

Sahin et al., "Isolation and characterization of a novel population of progenitor cells from unmanipulated rat liver," Liver Transpl. 14(3):333-45 (2008).

Saito et al., "Transplantation of liver organoids in the omentum and kidney," Artif Organs. 35(1):80-3 (2011).

Saleh et al., "Three-dimensional in vitro culture techniques for mesenchymal stem cells," Methods Mol Biol. 916:31-45 (2012).

Santamaria et al., "A combination of affinity chromatography, 2D DIGE, and mass spectrometry to analyze the phosphoproteome of liver progenitor cells," Methods Mol Biol. 909:165-80 (2012) (Abstract only).

Schmelzer et al., "Human hepatic stem cells from fetal and postnatal donors," J Exp Med. 204(8):1973-87 (2007).

Shiojiri et al., "Purification and culture of fetal mouse hepatoblasts that are precursors of mature hepatocytes and biliary epithelial cells," Methods Mol Biol. 826:3-10 (2012).

Sison-Young et al., "Comparative proteomic characterization of 4 human liver-derived single cell culture models reveals significant variation in the capacity for drug disposition, bioactivation, and detoxification," Toxicol Sci. 147(2):412-424 (2015).

Slany et al., "Cell characterization by proteome profiling applied to primary hepatocytes and hepatocyte cell lines Hep-G2 and Hep-3B," J Proteome Res. 9(1):6-21 (2010).

Smith et al., "A comprehensive evaluation of metabolic activity and intrinsic clearance in suspensions and monolayer cultures of cryopreserved primary human hepatocytes," J Pharm Sci. 101(10):3989-4002 (2012).

Snykers et al., "In vitro differentiation of embryonic and adult stem cells into hepatocytes: state of the art," Stem Cells. 27(3):577-605 (2009).

Sokal, "From hepatocytes to stem and progenitor cells for liver regenerative medicine: advances and clinical perspectives," Cell Prolif. 44(Suppl 1):39-43 (2011).

Sokal et al., U.S. Appl. No. 15/315,032, "Method for producing adult liver progenitor cells," filed Nov. 30, 2016 (109 pages).

Soto-Gutierrez et al., "Engineering of an hepatic organoid to develop liver assist devices," available in PMC Oct. 20, 2010, published in final edited form as: Cell Transplant. 19(6):815-22 (2010) (12 pages).

(56) References Cited

OTHER PUBLICATIONS

Sugahara et al., "Isolation of a novel mouse gene, mSVS-1/SUSD2, reversing tumorigenic phenotypes of cancer cells in vitro," Cancer Sci. 98(6):900-8 (2007).
Tanaka et al., "Identification and isolation of adult liver stem/progenitor cells," Methods Mal Biol. 826:25-32 (2012). (Abstract only).
Torres et al., "Hepatic progenitor cells: Another piece in the nonalcoholic fatty liver disease puzzle," Hepatology. 56(6):2013-5 (2012).
Tostöes et al., "Human liver cell spheroids in extended perfusion bioreactor culture for repeated-dose drug testing," Hepatology. 55(4):1227-36 (2012).
Vanheel et al., "Identification of protein networks involved in the disease course of experimental autoimmune encephalomyelitis, an animal model of multiple sclerosis," PLoS One. 7(4):e35544 (2012) (11 pages).
Wang et al., "Hepatitis B virus X (HBx) induces tumorigenicity of hepatic progenitor cells in 3,5-diethoxycarbonyl-1,4-dihydrocollidine-treated HBx transgenic mice," Hepatology. 55(1):108-20 (2012).
Watson et al., "Multiple functions of sushi domain containing 2 (SUSD2) in breast tumorigenesis," available in PMC May 10, 2015, published in final edited form as: Mol Cancer Res. 11(1):74-85 (2013) (23 pages).
White et al., "Identification of transcriptional networks during liver regeneration," J Biol Chem. 280(5):3715-22 (2005) (32 pages).
Wu et al., "Productive hepatitis C virus infection of stem cell-derived hepatocytes reveals a critical transition to viral permissiveness during differentiation," PLoS Pathog. 8(4):e1002617 (2012) (14 pages).
Yalaoui et al., "Hepatocyte permissiveness to Plasmodium infection is conveyed by a short and structurally conserved region of the CD81 large extracellular domain," PLoS Pathog. 4(2):e1000010 (2008) (12 pages).
Yu et al., "SyStemCell: a database populated with multiple levels of experimental data from stem cell differentiation research," PLoS One. 7(7):e35230 (2012) (11 pages).
Zhu et al., "Liver progenitor cell interactions with the extracellular matrix," J Tissue Eng Regen Med. 7(10):757-66 (2013) (Abstract only).
Jin et al., "Isolation and characterization of liver epithelial progenitor cells from normal adult rhesus monkeys (*Macaca mulatta*)," Cell Res. 19(2):268-70 and Suppl (2) (2009) (4 pages).
Berardis et al., "Gene expression profiling and secretome analysis differentiate adult-derived human liver stem/progenitor cells and human hepatic stellate cells," PLoS One. 9(1):e86137 (2014) (11 Pages).
Khuu et al., "Adult human liver mesenchymal stem/progenitor cells participate in mouse liver regeneration after hepatectomy," Cell Transplant. 22(8):1369-80 (2013).
Sokal et al., "Phase I/II clinical trial of heterologous human adult liver-derived progenitor cells (HHALPC, hepastem) in urea cycle disorders (UCD) and Crigler-Najjar syndrome (CN): six months follow-up results," Hepatology. 60(Suppl 4):525A (2014) (1 page).

\* cited by examiner

Fig. 2
A)
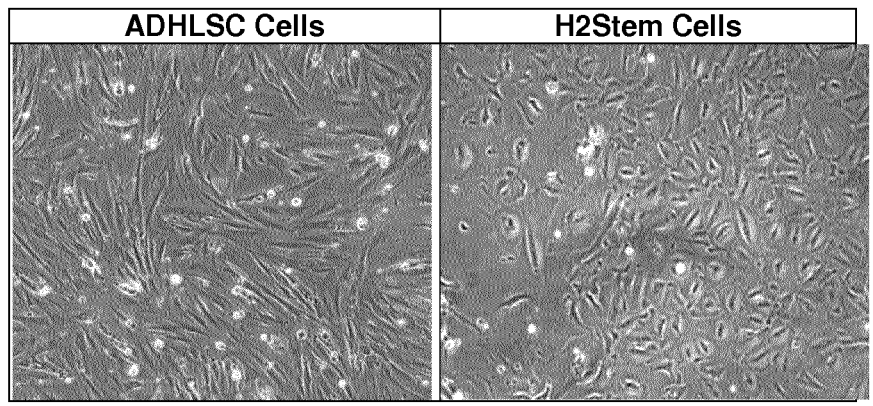
B)
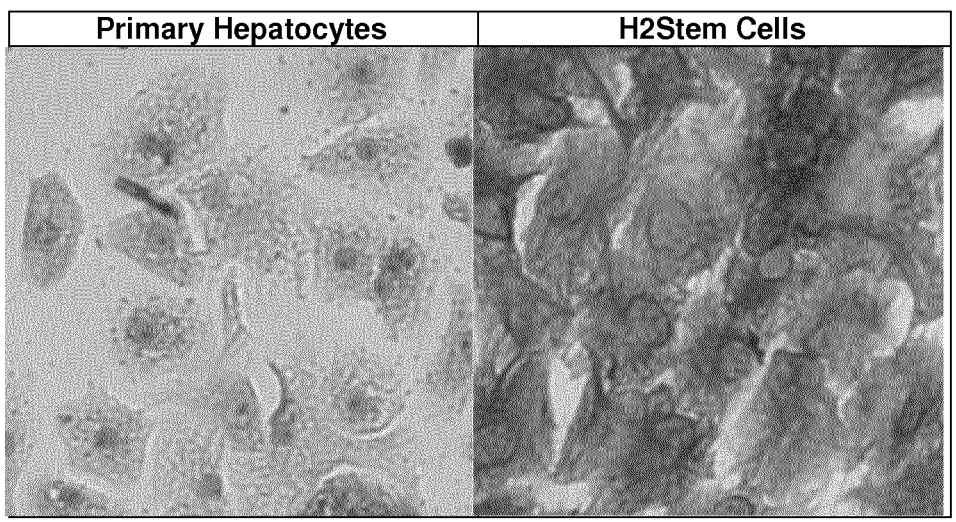

Fig. 3
A) After 24 hours
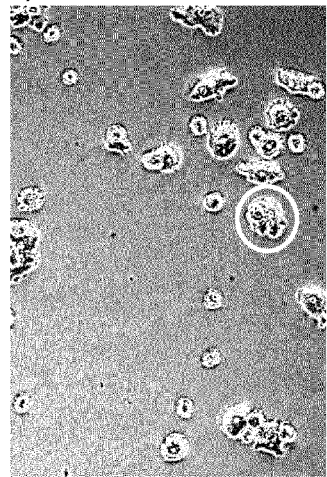
B) After 59 hours
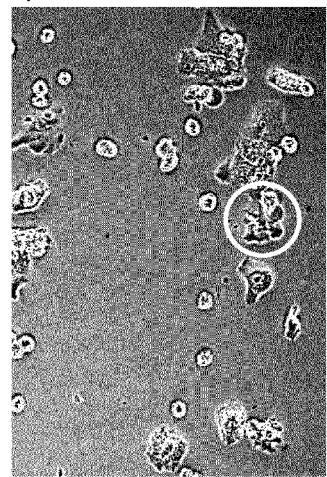
C) After 85 hours
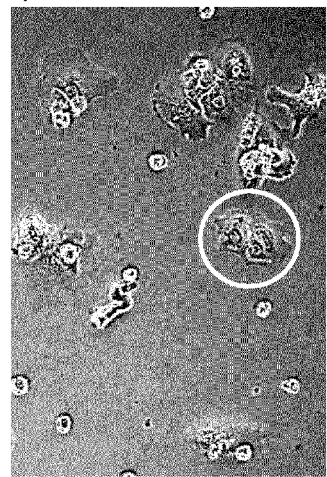
D) After 119 hours
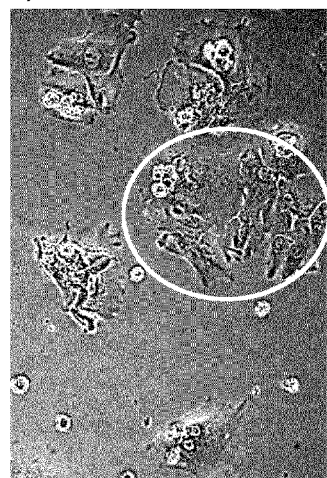
E) After 153 hours
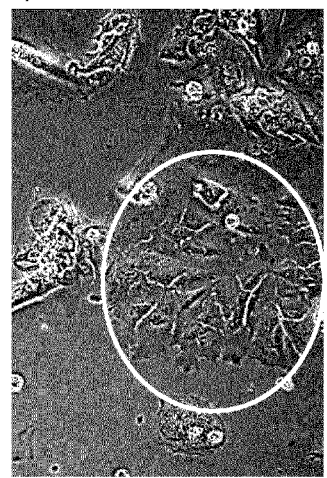
F) After 186 hours
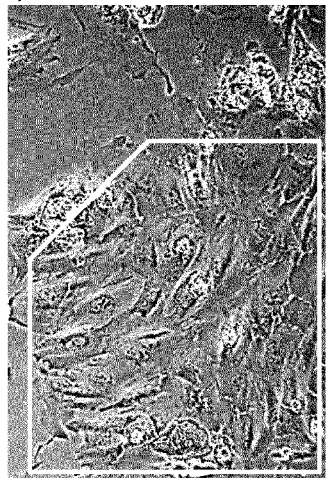

Fig. 4
A)
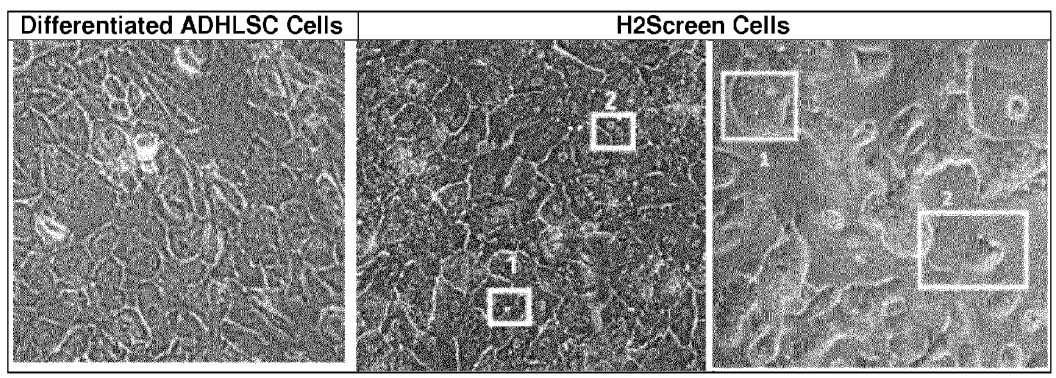
B)
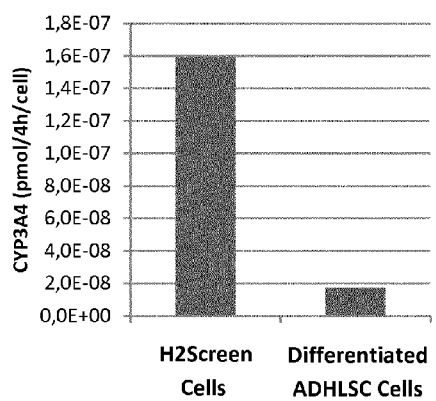
C)
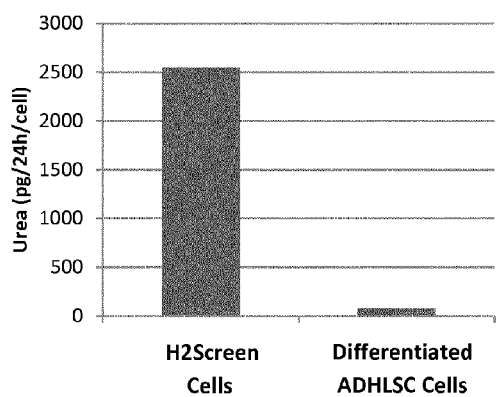
D)
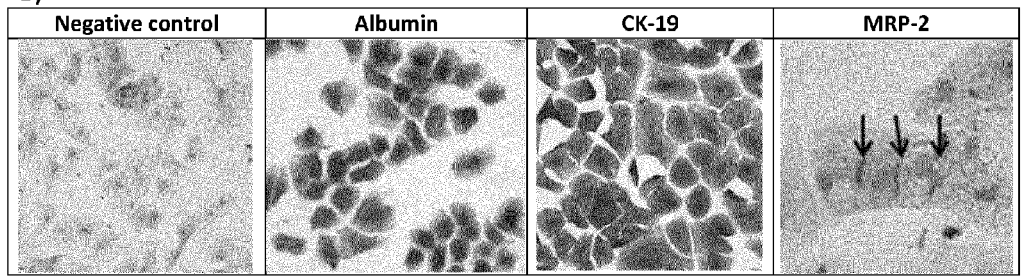

Fig. 5
A) H3Stem Cells
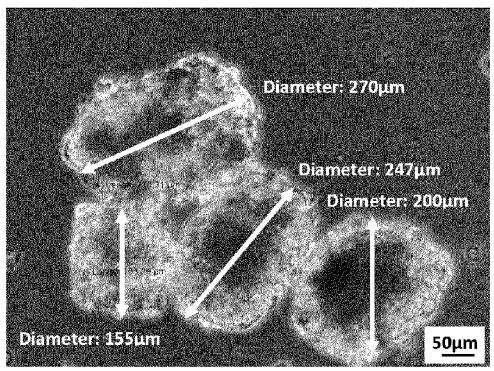
B) H3Screen-1 Cells
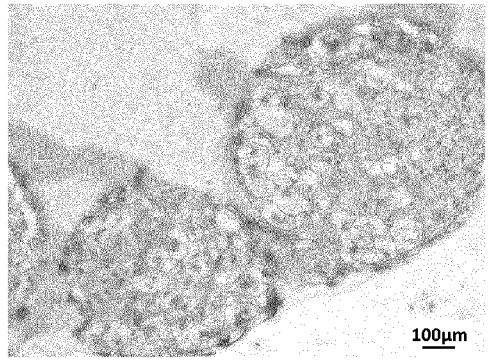
C) H3Screen-2a Cells (low binding plates)
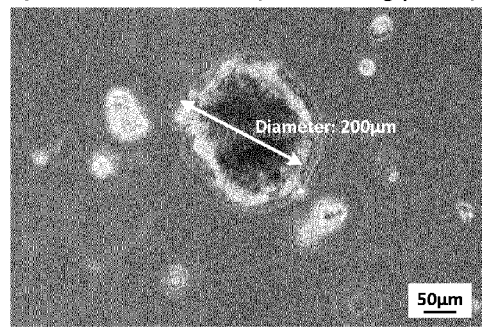
D) H3Screen-2a Cells (in U-shaped wells)
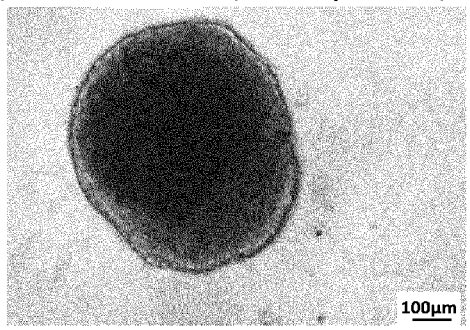
E) Collagen-plated H3Screen-2b Cells
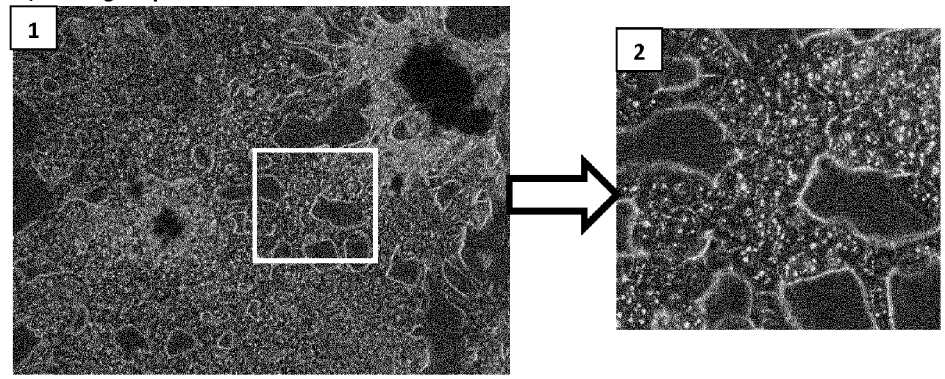

Fig. 6
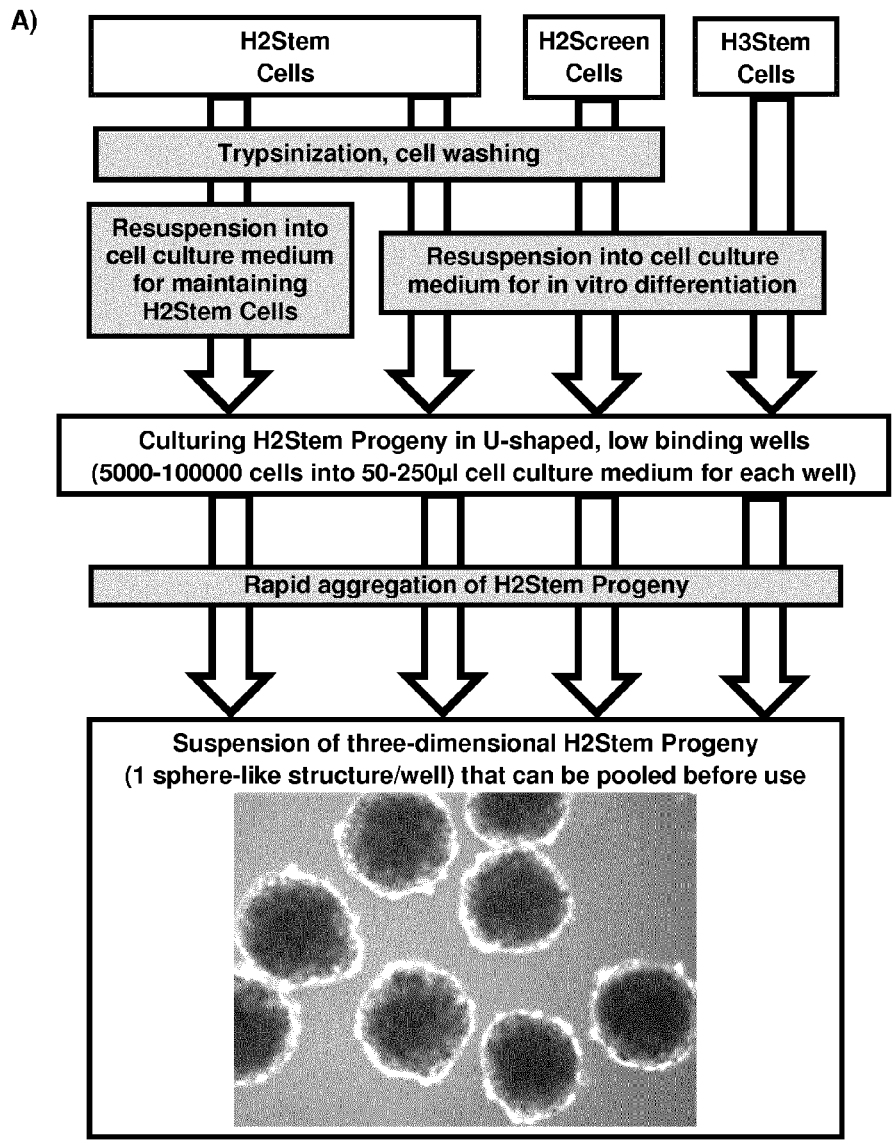
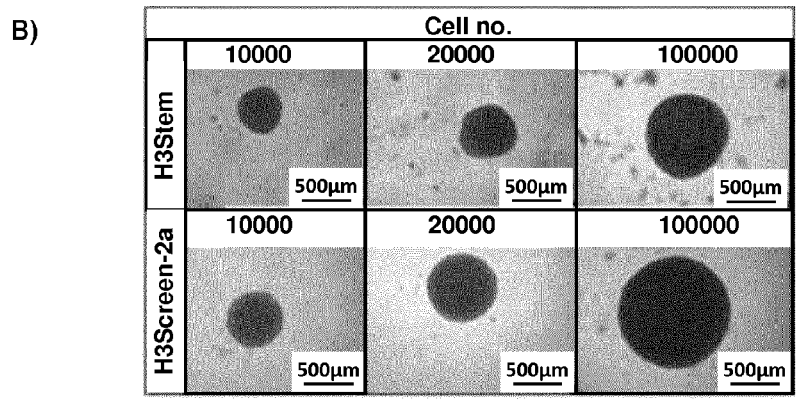

Fig. 8
A)
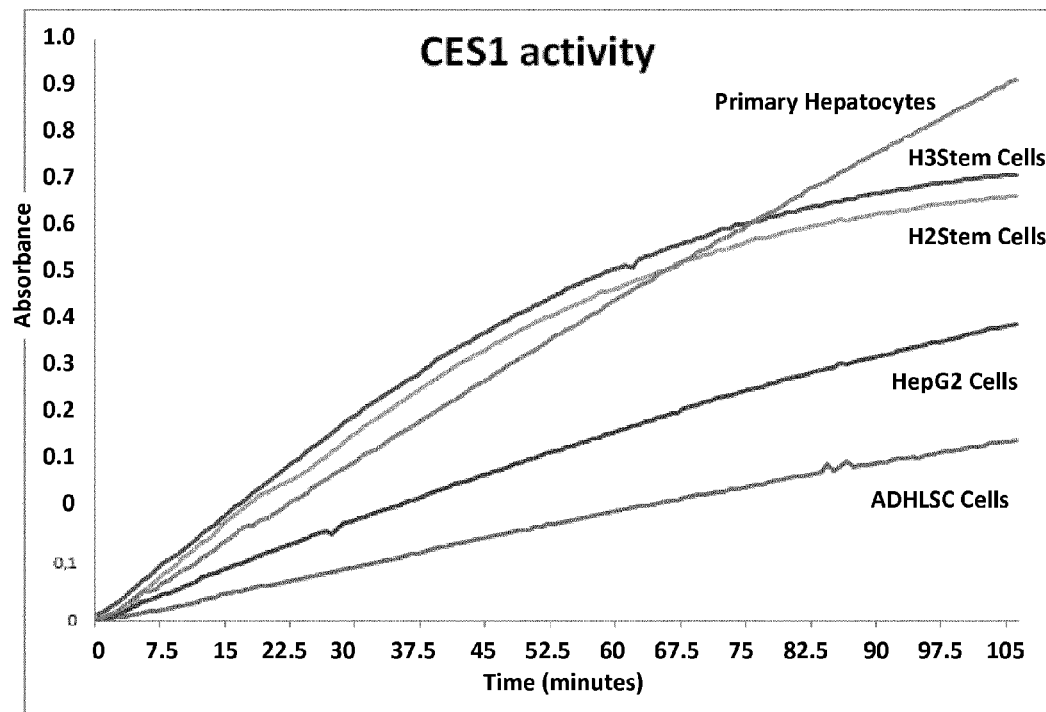
B)
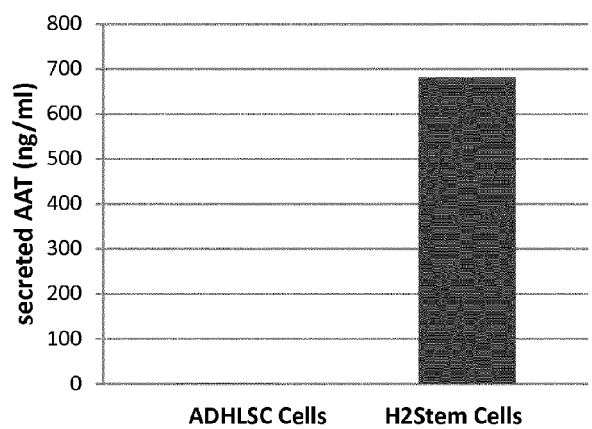

Fig. 10
A)
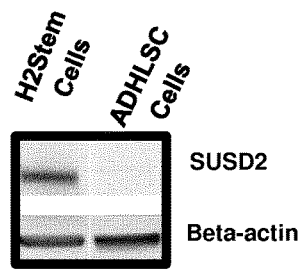
B)
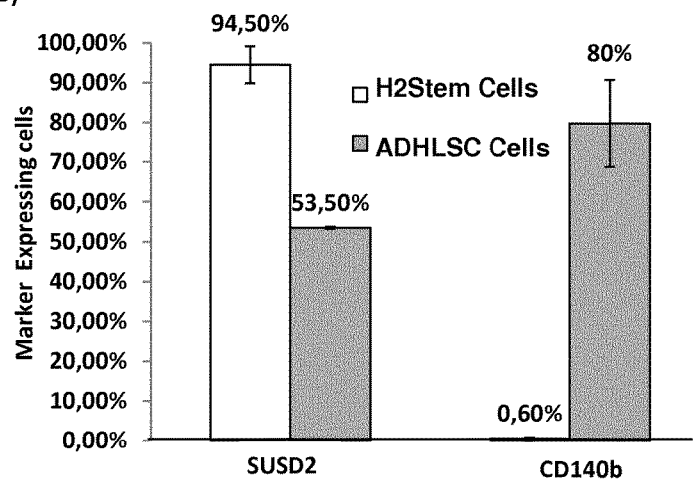
C)
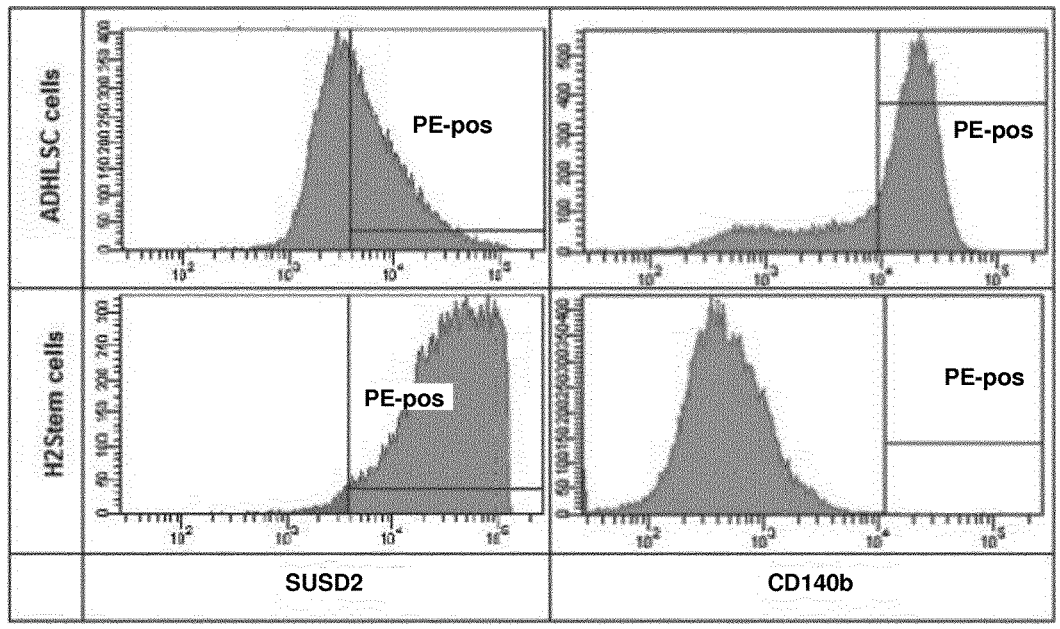

METHOD FOR PRODUCING ADULT LIVER PROGENITOR CELLS

TECHNICAL FIELD

The present Invention relates to adult liver progenitor cells that are generated using primary liver cells and their use for the medical management of liver diseases or for screening compounds of medical interest.

FIELD OF THE INVENTION

Liver is a key organ in the regulation of body homeostasis and is the site of many vital metabolic pathways. Impairment of only one protein within a complex metabolic pathway could be highly deleterious. The large presence of important liver enzymes substantially increases the risk occurrence of diverse liver diseases. Altogether, 200 different inborn errors of liver metabolism exist, affecting 1 child over 2500 live births. Current treatments, and long-term management, are not efficient enough. Orthotopic liver transplantation (OLT) is highly intrusive, irreversible, limited by shortage of donor grafts and demands state-of-art surgery. Liver cell transplantation (LCT) may exert only short-to-medium term efficacy due to the quality of hepatocyte preparations. Further improvements in tolerance towards cryopreservation, permanent engraftment, and high functionality of the infused cells, would be a major breakthrough (Sokal E M, 2011; Russo F P and Parola M, 2012; Allameh A and Kazemnejad S, 2012; Parveen N et al., 2011).

This improvement could be brought by the use of stem or progenitor cells, in particular liver progenitor cells that have been identified in the literature using liver tissues from different organisms, as well as in fetal or adult liver tissues (Schmelzer E et al., 2007; Sahin M B et al., 2008; Azuma H et al., 2003; Herrera M B et al., 2006; Najimi M et al., 2007; Darwiche H and Petersen B E, 2010; Shiojiri N and Nitou M, 2012; Tanaka M and Miyajima A, 2012). Such cells can provide, following the exposure to hepatogenic stimuli in vitro and/or after in vivo administration, cells with morphological and functional features typically associated to hepatic differentiation such as phase I/II enzymatic activities.

These liver progenitor cells or hepatocyte-like cells that are generated from them can be used in cellular transplantation as well as for drug testing in the development of new drugs since they represent a surrogate for primary human hepatocytes in drug metabolism and pharmacological or toxicological in vitro screening (Dan Y Y, 2012; Hook L A, 2012). However, it is currently impossible to determine which of the liver progenitor cells so far identified are the best for therapy of a given disease or use. This is largely due to the great variability in methods used to characterize cells and their differentiation ability, variability in transplantation models and inconsistent methods to determine the effect of cell grafting in vivo.

Hepatocyte spheroids or liver organoids, which are spherical, multicellular aggregates of hepatocytes greater than 50 µm in diameter, may provide a useful three-dimensional tissue construct for cell transplantation and bioartificial livers. Several methods, such as the culturing of hepatocytes on non-adherent plastic surfaces for self-assembly and rotational culturing via spinner flasks, have been employed for the formation of spheroids from mammalian hepatocytes (Lu Y et al., 2012; Saito R et al., 2011; Soto-Gutierrez A et al., 2010; Mitaka T and Ooe H, 2010; Tostoes R M et al., 2012). These structures may be generated by providing adequate support to the three-dimensional growth of the cells, in particular by mimicking their interactions with liver microenvironment and especially with the extracellular matrix (ECM).

There is considerable evidence from in vivo studies that matrix proteins affect the activation, expansion, migration and differentiation of adult liver progenitor cells but the information on the role that specific ECM proteins play on in vivo and in vitro activities is still limited (Zhu C et al., 2013). Some evidences on the expression of ECM-specific receptors in liver progenitor cells have been published (Najimi M et al., 2007; Miyazaki M et al., 2007). However, there is no evidence on how liver progenitor cells or other poorly differentiated cells of liver origin that present a specific combination of hepatic markers, mesenchymal markers and liver-specific metabolic activities can be produced in cell culture and that form three-dimensional cell clusters, without making use of inadequate and/or complex technical solutions involving embryonic or pluripotent stem cells, recombinant DNA technologies, or chemicals.

SUMMARY OF THE INVENTION

The present Invention is based on the observation that specific cell culture conditions allow obtaining novel adult liver progenitor cells with specific expression profile and improved biological features and that can be used for producing either cell-based pharmaceutical compositions that can be administered for the treatment of liver diseases, or metabolically and hepato-active cells that can be used for characterizing the efficacy, metabolism, and/or toxicity of a compound.

These cells, named H2Stem Cells, represent a cell population that has morphological and functional features that are distinct from those identified in previously described adult liver progenitor cells that are isolated or otherwise produced from human donors, in particular with respect to high level of expression of proteins providing liver-specific metabolic activities (e.g. CYP3A4 activity) in combination with at least one mesenchymal (for example, selected from Vimentin, CD90, CD73, CD29, CD44, Alpha Smooth Muscle Actin) and at least one hepatic marker (for example, selected from albumin, HNF-3b, HNF-4). In addition, in some embodiments further intracellular markers can provide relevant criteria for characterizing H2Stem Cells, such as the significant presence of cells expressing cytokeratin 19.

H2Stem Cells that are obtained or obtainable by the methods of the Invention are defined as a cell population being positive for at least one mesenchymal marker (optionally selected from ASMA, Vimentin, CD90, CD73, CD44, and CD29), being positive for at least one hepatic marker (optionally selected from HNF-4, HNF-3B, and albumin), and are positive for a least from one liver-specific metabolic activity (optionally selected from urea secretion, bilirubin conjugation, and CYP3A4 activity). Additionally, H2Stem Cells may further comprise one or more of the following additional properties: comprising at least 20%, between 20% and 90%, or between 20% and 40% of cytokeratin 19-positive cells (when measured by flow cytometry), being positive for a marker for Sushi domain 2 containing protein, presenting a cuboidal meso-epithelial morphology (that is, a morphology similar to epithelial cells derived from the mesoderm), and/or being capable of forming three-dimensional cell clusters that present liver-specific metabolic activities.

A main embodiment of the invention comprises an adult liver progenitor cell that is measured positive for a combination of biological activities and for markers that can be identified on their surface, intracellular, and/or secreted including the following:

(a) at least one hepatic marker selected from albumin, HNF-3B, HNF-4, CYP1A2, CYP2C9, CYP2E1 and CYP3A4;
(b) at least one mesenchymal marker selected from Vimentin, CD90, CD73, CD44, and CD29;
(c) at least one liver-specific activity selected from urea secretion, bilirubin conjugation, alpha-1-antitrypsin secretion, and CYP3A4 activity;
(d) Sushi domain containing protein 2 (SUSD2); and
(e) Cytokeratin-19 (CK-19).

In some embodiments, the adult liver progenitor cell can be further characterized by a series of negative markers, in particular H2Stem Cells can be measured negative for one or more of CD140b, CD45, CD117, CD31, CD133, and CD326. In further embodiments, H2Stem Cells may also be measured positive for one or more of the following activities and markers: Cytokeratin-18 (CK-18); alpha smooth muscle actin (ASMA); one or more coagulation-related secreted protein (such as fibrinogen alpha, fibrinogen beta, fibrinogen gamma, Factor V, Factor VII, Factor VIII, Factor IX, and Factor XIII); one or more further liver-specific activities (such as sulfotransferase activity, tryptophan-2,3-dioxygenase activity, liver carboxylase activity, ammonia metabolism, and glycogen storage).

The biological activities, the markers, and the morphological/functional features listed above can be present in H2Stem Cells in various different combinations. In some embodiments, H2Stem Cells are measured:

(a) positive for albumin, Vimentin, CD90, CD73, urea secretion, bilirubin conjugation, alpha-1-antitrypsin secretion, CYP3A4 activity, Sushi domain containing protein 2, Cytokeratin-19, and liver carboxylase activity; and also
(b) negative for CD140b.

Further criteria can be also determined for H2Stem Cells of the above embodiments in any functional and technical combination, for instance by measuring positive for:

At least one further hepatic marker selected from HNF-3B, HNF-4, CYP1A2, CYP2C9, CYP2E1 and CYP3A4;
At least one further mesenchymal marker selected from CD44 and CD29;
At least one further liver-specific activity selected from sulfotransferase activity, tryptophan-2,3-dioxygenase activity, ammonia metabolism, and glycogen storage;
At least one of Cytokeratin-18 (CK-18) and alpha smooth muscle actin (ASMA); and/or
At least one coagulation-related secreted protein selected from fibrinogen alpha, fibrinogen beta, fibrinogen gamma, Factor V, Factor VII, Factor VIII, Factor IX, and Factor XIII.

In some of the above embodiments, H2Stem Cells can be measured negative for at least one further marker selected from CD45, CD117, CD31, CD133, and CD326.

In a still further embodiment, H2Stem Cells present specific morphology and/or functional features. In particular, H2Stem Cells of the above embodiments may be adherent and may present cuboidal meso-epithelial morphology. Moreover, H2Stem Cells of the above embodiments may be further capable of forming three-dimensional cell clusters in suspension (named H3Stem Cells). As summarized in FIG. 1, both H2Stem Cells and H3Stem can further differentiate into cells that present strong liver-specific activities being adherent cells (named H2Screen Cells) and three-dimensional cell clusters in suspension (named H3Screen Cells).

Indeed, H2Stem Cells of any of the above embodiments can be used for providing additional, isolated cell populations, collectively grouped under the name of H2Stem Progeny, comprising H2Stem Cells as defined above that are obtained by passaging them in in cell culture conditions. In particular, H2Stem Progeny results from the maintenance, proliferation, and/or differentiation of H2Stem Cells in cell culture conditions (or following implantation in an animal model), as required for the desired use, and in particular as three-dimensional cell clusters (three-dimensional H2Stem Progeny). These three-dimensional structures not only present improved liver-specific metabolic activities and maintain a combination of specific cell markers but also provide H2Stem Progeny in a format that is particularly appropriate for establishing formulations for therapeutic uses and high-throughput screening.

Thus, the above cell population embodiments include the isolated H2Stem Progeny that comprises cells presenting the biological activity, the markers, the morphology and/or functional features listed above in a large majority (e.g. for instance at least 60%, at least 70%, at least 80%, at least 90%, at least 95%, or at least 99%). In a preferred embodiment, a population of H2Stem Cells comprises at least 60%, or between 60% and 99% or between 70% and 90% of cells that are measured:

(a) Positive for albumin, Vimentin, CD90, CD73, urea secretion, bilirubin conjugation, alpha-1-antitrypsin secretion, CYP3A4 activity, Sushi domain containing protein 2, Cytokeratin-19, and liver carboxylase activity; and
(b) Negative for CD140b.

In addition, such H2Stem Progeny can be provided as adherent cells or forming three-dimensional cell clusters in suspension, that preferably also present inducible Phase I CYP-dependent activity and uptake of Taurocholate, Estrone-3-sulfate, or 1-methyl-4-phenylpyridinium. Moreover, such cell population can be further differentiated into cells presenting liver-specific activities.

H2Stem Cells and H2Stem Progeny can be also modified by means of one or more chemical agents, cell culture medium, growth factors, and/or nucleic acids vectors for any in vivo or in vitro use that requires appropriately adding or eliminating any properties of such cells.

In a further main embodiment, the present Invention allows producing H2Stem Cells and H2Stem Progeny by means of a method for obtaining adult liver progenitor cells comprising:

(a) disassociating adult liver or a part thereof to form a population of primary liver cells;
(b) generating a preparation of the primary liver cells of (a);
(c) culturing cells comprised in the preparation of (b) onto a support that allows adherence and growth of cells thereto and emergence of a population of cells having cuboidal meso-epithelial morphology;
(d) passaging the cells of (c) at least once; and
(e) isolating a population of cells obtained after the passaging of (d) that are positive for at least one hepatic marker and at least one mesenchymal marker, have at least one liver-specific metabolic activity, and maintain a cuboidal meso-epithelial morphology.

Another aspect of the present invention relates to a method for obtaining adult liver progenitor cells comprising:

(a) disassociating adult liver or a part thereof to form a population of primary liver cells;

(b) generating a preparation of the primary liver cells of (a);
(c) culturing cells comprised in the preparation of (b) onto a support that allows adherence and growth of cells thereto and the emergence of a population of cells having cuboidal meso-epithelial morphology;
(d) passaging the cells of (c) at least once; and
(e) isolating a population of cells obtained after the passaging of step (d) that maintain a cuboidal meso-epithelial morphology, and that are positive for at least one hepatic marker, at least one mesenchymal marker, and have at least one liver-specific activity, wherein at least a fraction of the cell population of step (e) that may range from at least 20% or from 20 to 40% of the total cell population of step (e), is positive for cytokeratin-19 by flow cytometry.

Methods of the present invention relate to isolating liver cells that can provide H2Stem Cells (and consequently for providing also H2Stem Progeny) after being maintained in appropriate cell culture conditions. These methods are applicable starting from fresh primary liver cells of human origin and/or from cryopreserved preparations of primary liver cells. In some embodiments of the methods, these methods can also involve measuring the positivity to one or more marker in step (e) and/or in step (c).

For instance, the cells of step (c) and/or the cell population of step (e) may be measured positive for at least one marker or activity selected from cytokeratin 19, albumin, alpha-1-antitrypsin secretion, Sushi domain containing protein 2, and CYP3A4. In a preferred embodiment, the cells of step (c) and/or the cell population of step (e) are measured positive for:

(i) at least one mesenchymal marker selected from Vimentin, CD90, CD73, CD44, and CD29;
(ii) at least one hepatic marker selected from alpha-1-antitrypsin, HNF-3B, HNF-4, albumin, CYP1A2, CYP2C9, CYP2E1;
(iii) at least one liver-specific metabolic activity chosen from urea secretion, bilirubin conjugation, alpha-1-antitrypsin secretion, and CYP3A4 activity;
(iv) Sushi domain containing protein 2; and
(v) Cytokeratin-19 (CK-19).

The cells of step (c) and/or the cell population of step (e) can be further measured positive for Cytokeratin-18 (CK-18) and/or alpha smooth muscle actin (ASMA), and can be measured negative for CD140b.

In some of embodiments of the methods, the cells of step (c) and/or the cell population of step (e) is measured positive for a marker if at least 60%, at least 70%, at least 80%, at least 90%, at least 95%, or at least 99%, or between 60% and 99%, or between 70% and 90% of cells in the population are determined to be positive for that marker. In some of the above embodiments, the cells of step (c) and/or the cell population of step (e) is measured negative for a marker if less than 20% or less than 10% of the cells in the population are determined to be negative for the marker. In some of the above embodiments, the cell population of step (e) comprises adherent cells or forms three-dimensional cell clusters in suspension, while in other above embodiments, the cell population of step (e) presents inducible Phase 1 CYP-dependent activity and uptake of at least one of Taurocholate, Estrone-3-sulfate, and 1-methyl-4-phenylpyridinium. The cells of step (c) and/or cell population of step (e) can be also modified by means of chemical agents, cell culture medium, growth factors, and/or nucleic acid vectors for any appropriate later in vivo or in vitro use.

Thus, the above methods allow for obtaining H2Stem Cells and H2Stem Progeny of the embodiments above. In some embodiments of the methods, the cells of step (c) and/or cell population of step (e) may be cultured onto a support that can be coated with collagen or other appropriate peptide or extracellular matrix protein, may be isolated by measuring at least the positivity for specific combinations of hepatic markers, mesenchymal markers, and liver-specific metabolic activities. Then, depending on the desired use of H2Stem Cells and H2Stem Progeny, the cells that are obtained or obtainable by this method can be maintained in cell culture conditions allowing their proliferation as adherent cells, cell suspensions, or, by applying specific conditions for maintaining them, as hepatocyte-like or hepato-active cells. In particular, three-dimensional cell clusters (three-dimensional H2Stem Progeny) that can be formed in a particularly efficient manner using commercially available low adherence container (in the form of plates or U-shaped wells) or in a bioreactor and characterized according to their functional, dimensional, morphological, and/or antigenic features. The method of the invention may further comprise a step (f) in which the cell population of step (e) is maintained in a cell culture condition to differentiate them into cells presenting liver-specific activities.

A H2Sstem Progeny is a cell population that is obtainable by methods of the invention and comprising cells presenting the biological activity, the markers, the morphology and/or functional features listed above in a large majority (e.g. for instance at least 60%, at least 70%, at least 80%, at least 90%, at least 95%, or at least 99%). In a preferred embodiment, a population of H2Stem Cells obtainable by the methods of the invention comprises between 60% and 99% or between 70% or 90% of cells presenting the features listed above in connection to step (e).

The method of the invention also provides H2Stem Progeny as adherent cells or forming three-dimensional cell clusters in suspension, that preferably also present inducible Phase I CYP-dependent activity and uptake of at least one of Taurocholate, Estrone-3-sulfate, and 1-methyl-4-phenylpyridinium. Moreover, such cell populations can be further differentiated into cells presenting liver-specific activities. A population of H2Stem Cells that is obtained by the methods of the invention can be also modified by means of chemical agents, cell culture medium, growth factors, and/or nucleic acids vectors for any appropriate in vivo or in vitro use.

Biological materials that are obtained when generating H2Stem Cells or an H2Stem Progeny according to the invention can be further used for identifying biological entities that may have specific uses, in particular distinct medical applications. These biological materials include not only H2Stem Cells and H2Stem Progeny (or sub-population, cell lines, and fraction thereof) that present specific features (e.g. protein- or nucleic acid-based markers, biological activities, and/or morphology) but also any other entity that is obtained when producing preparations of H2Stem Cells or H2Stem Progeny from culture of primary liver cells. Biological materials of the invention include, for example, conditioned cell culture media and fractions of these media that may contain proteins, metabolites, membrane vesicles, antigens, and/or nucleic acids that, together or not with other features characterizing the cells themselves (e.g. cell surface antigen or enzymatic activities), can be identified and used as markers for detecting cells of medical interest or as compounds that present activities or distribution of medical interest, in particular in connection to liver diseases. Indeed, the comparative analysis of protein extracts that were obtained from H2Stem Cells have made possible identifying Sushi domain containing protein 2 as a further marker for which H2Stem Cells are positive and that may be used for characterizing H2Stem Cells and H2Stem Progeny.

H2Stem Cells, H2Stem Progeny, biological materials that are obtained when generating H2Stem Cells or an H2Stem Progeny, and compositions comprising such cells or biological materials ("H2Stem Products", collectively), can be useful for a large number of methods and applications, either in vivo or in vitro. In particular, an H2Stem Product can be used for treating diseases (e.g. liver diseases) and for establishing methods and biological assays that require cells presenting biological features (such as metabolic or enzymatic activities, or an antigenic profile) as similar as possible to those observed for primary hepatocytes for the desired period of time, once they are differentiated either in vivo or in vitro. Preferred H2Stem Products are an H2Stem Progeny, a biological material that is obtained when generating H2Stem Progeny, and a composition comprising either H2Stem Progeny or such biological material. More preferably, an H2Stem Product is an H2Stem Progeny or a composition comprising an H2Stem Progeny.

In particular, an H2Stem Product can be used for in vivo administration (in humans or in animals, such as in animal models), for example in the form of a pharmaceutical composition comprising such cells, for treating a liver disease (such as an inborn error of liver metabolism, an inherited Blood Coagulation Disorder, progressive familial intrahepatic cholestasis type 1/2/3, alpha 1-Antitrypsin Deficiency, defect of liver cell transporters, Porphyria, fatty liver or other fibrotic liver disease, primary biliary cirrhosis, sclerosing cholangitis, liver degenerative disease, and acute or chronic liver failure). These pharmaceutical compositions can be provided as H2Stem Products combining H2Stem Cells (or a given H2Stem Progeny) with a support (e.g. a matrix, a capsule, a scaffold, or a device) and/or a solution (e.g. cell culture medium or buffer) that is appropriate for the desired method of treatment, administration, and/or storage, as well as in the preferred means for providing such pharmaceutical compositions (e.g. within a kit). Other agents of biological (e.g. antibodies or growth factor) or chemical origin (e.g. drugs, preserving or labeling compounds) that may provide any other useful effect can be also combined in such compositions.

A method for preventing and/or treating a disease comprises administering an H2Stem Product, such as H2Stem Cells or a given H2Stem Progeny, and preferably within a composition, to a subject in need thereof. In particular, a method of treating a disease (e.g. a liver disease) in a patient in need thereof comprises administering an effective amount of an H2Stem Product to the patient.

An H2Stem Product can also be used for in vitro studies, in particular for pharmacological studies for evaluating the efficacy, metabolism, stability and/or toxicity of one or more exogenous components such as a biological product (such a protein, a nucleic acid, lipids, or a sugar) or a chemical compound (organic or inorganic, including salts or metals). This approach may be used also for studying effects of other cells (such as bacteria or other cells, preferably of human origin) on an H2Stem Product, as well as evaluating the infection and/or the replication of liver-specific viruses (e.g. hepatitis viruses) that can be later purified or otherwise detected.

Thus, the present invention also provides methods for evaluating the efficacy, the metabolism, the stability, and/or the toxicity of one or more exogenous components, either in vitro or in vivo, said method comprising:

(a) providing an H2Stem Product;
(b) exposing said H2Stem Product to one or more exogenous components selected from chemical compounds, proteins, nucleic acids, lipids, sugars, metals, salts, viruses, bacteria, and cells; and
(c) detecting the effects of said one or more exogenous components on said H2Stem Product and/or detecting the presence, localization, or modification of said one or more exogenous components following the exposure to said H2Stem Product.

This general method can include in some embodiments further steps and features that apply to specific uses and/or technologies. For instance, step (c) as defined above can comprise detecting the effects on cell morphology, on cell viability, on up- or down-regulation of liver-specific or unspecific proteins, and/or on the degradation, aggregation, activation, or inhibition of proteins within an H2Stem Product. Furthermore, step (c) as defined above can comprise detecting the internalization of such one or more exogenous components into, or the physical association with, an H2Stem Product. The H2Stem Product can be also provided to an animal at step (a), and then one or more exogenous components is administered to said animal in step (b). Finally, the step (c) comprises detecting the effects of said one or more exogenous components on said H2Stem Product or on said animal, and/or detecting the presence, localization, or modification of said one or more exogenous components following the exposure to said H2Stem Product in the animal.

The methods of using H2Stem Products may also involve exposing the cell population, composition, or biological material in step (b), simultaneously or sequentially in any order, to:
(i) one or more exogenous components that have an effect cell morphology, cell viability, up- or down-regulation of liver-specific or unspecific proteins, and/or that degrade, aggregate, activate, or inhibit proteins within an H2Stem Product; and
(ii) one or more exogenous components that is intended to block or avoid such effects within the H2Stem Product.

In some embodiments, this method is intended to use any H2Stem Product, and in particular an H2Stem Progeny as a model of hepatic cells for determining if, when exposed to an exogenous component that is pathogenic agent, a further exogenous components that is a candidate drug specifically targeting the pathogenic agent and/or their effects has therapeutic properties since it prevents or blocks any undesirable effect of the pathogenic agent (e.g. viral infection, apoptosis, oncogenic transformation, reduction of liver-specific activities, etc.). In particular, the exogenous component of (i) above that is pathogenic agent, comprises an infectious, tumorigenic, cytotoxic, or genotoxic agent, and the further exogenous components of (ii) above that is a candidate drug specifically targeting the pathogenic agent and/or their effects, comprises a protein, a nucleic acid, a cell, a virus, or a chemical compound.

The H2Stem Product can also be provided in a kit, for example, for the uses and methods of the applications as described above, including for transferring an H2Stem Product to a clinical institution and providing means for administering it to a patient. This kit can comprise an H2Stem Product and, optionally, further elements that allow using and/or detecting the H2Stem Product and their activities, as well as for using and/or detecting any relevant additional compound. This kit can comprise one or more vials containing an H2Stem Product (e.g. an H2Stem Progeny or a composition comprising H2Stem Progeny) and one or more of the following elements to be selected according to the specific use: devices, disposable materials, solutions, chemical products, biological products, and/or instructions for using the elements of said kit.

The Detailed Description and the Examples provide additional details on the cells, the cell populations, the methods, the cells obtainable by these methods, and on further embodiments of the Invention that are associated to said methods and H2Stem Products.

DESCRIPTION OF FIGURES

FIG. 2: Features distinguishing adherent, undifferentiated ADHLSC Cells or primary human hepatocytes from adherent, undifferentiated H2Stem Cells and H2Stem Progeny when cultured on a substrate such as collagen. Morphologically, non-differentiated ADHLSC Cells appear as a homogenous population of elongated cells, while H2Stem Cells appear as a homogenous population of cuboidal, meso-epithelial cells (A). When analyzed by immunocytochemistry using an anti-CK-19 antibody, primary human hepatocytes appear (as ADHLSC Cells) poorly expressing CK-19, meanwhile H2Stem Cells appears as highly positive for CK-19, with nuclei surrounded by strongly CK-19 positive darker filaments (B). The cells were photographed at a magnification of 10× (A) or 40× for (B).

FIG. 3: Morphology of H2Stem cells that are obtained by culturing primary liver cells in appropriate cell culture conditions. Images were taken using Cell-IQ equipment each hour on the same position in the plate from days 1 to −8 and a selection of images at the indicated hours has been made to show the morphological transition of primary liver cells to a cluster of adherent, proliferating H2Stem Cells. The cells were photographed at a magnification of 20×.

FIG. 4: Features distinguishing adherent, differentiated ADHLSC Cells from adherent, undifferentiated H2Screen Cells when cultured on a substrate such as collagen. Morphologically, following differentiation as adherent cells, ADHLSC Cells appear as a non-granular, polygonal homogenous population of cells (A, left panel, early stage), while an H2Stem Progeny comprising H2Screen Cells appear as a homogenous population of granular, cuboidal/polygonal cells with stromal support that, at a more advanced stage of cell culture and differentiation, may form cell clusters distributed within large stromal structures (A, right panel, late stage). In these latter images, white box 1 indicates areas of cells with morphology similar to hepatocytes and bile canaliculi start appearing; white box 2 indicates an area with binucleated cells and extracellular matrix. The cells were photographed at a magnification of 20×). Differentiated ADHLSC Cells and H2Screen Cells were characterized according to their CYP3A4 activity (B) and urea secretion (C). Baseline level of activity is $10^{-9}$ pmol/cell/4 h and 5 μg/cell/24 h, respectively. Higher urea secretion levels for H2Screen Cells, when compared to ADHLSC Cells, were also measured by performing the assays for shorter periods (2-6 hours). Immunohistochemistry (D) further confirms H2Screen strong expression, when compared to negative control (no primary antibody), of intracellular albumin and CK-19, as well as of the efflux transporter MRP2 (at the interface between cells; see arrows).

FIG. 5: Morphology of distinct forms of H2Stem Progeny consisting of three-dimensional cell clusters. H3Stem Cells initially form clusters of about 50-100 μm with a denser core of cells that later on can form larger structures (up to 1000 μm or more) and that comprise 100000 or more of such cells (A). H3Screen-1 Cells that are obtained from H2Screen Cells appear as cluster of granular cuboidal/polygonal, hepatocyte-like cells surrounded by supportive stroma (B). H3Screen-2a Cells also consist of three-dimensional clusters of granular cuboidal/polygonal hepatocyte-like cells surrounded by supportive stroma that can be obtained by performing in vitro differentiation using low binding plates (C) or in U shaped, low-binding wells where more uniform three-dimensional H3Screen-2a Cells are obtained (D; also H3Stem Cells form similar structures when using the same approach for culturing them). Finally, when H3Screen Cells are cultured on a substrate like collagen, the resulting H3Screen-2b Cells appear as adherent clusters of cells that are similar to hepatocytes and distributed within supportive stroma and extensive intracellular granular structures (E; the white box in panel 1 is enlarged in Panel 2). The cells were photographed at a magnification of 10× (panel 1 of E).

FIG. 6: Distinct types of H2Stem Progeny can provide three-dimensional H2Stem Progeny having homogeneous size according to different approaches. The flowchart summarizes the steps for obtaining such cell preparations (A). A specific H2Stem Progeny is used for seeding cells, at a given volume and concentration, in each Ultra-Low Attachment cell culture flasks, adding 5 ml of fresh cell culture medium with same frequency. Otherwise, Ultra-Low Attachment, U-shaped/round cell culture microplates containing 96 wells can be used to seed and grow these cells in order to obtain a sphere-like structure for each well. The resulting three-dimensional H2Stem Progeny can be used within the same well (by substituting the cell culture medium and/or adding reagents) or after transferring and pooling the content of 2, 5, 10 or more wells into an appropriate container. The photo in the text box at the bottom of the flowchart in (A) shows such a pooled preparation of H3Screen-2a Cells but it is representative of other three-dimensional H2Stem Progeny that are either undifferentiated (H3Stem Cells) or differentiated (H3Screen-1 Cells) and obtained using the same approach. The morphology of sphere-like structures comprising H3Stem Cells or H3Screen-2a Cells that are generated using the Ultra-Low Attachment, U-shaped/round cell culture microplates appears can be compared (B). Due to the differentiation that provides larger cells, the sphere-like structures comprising H3Screen-2a Cells are larger than sphere-like structures comprising an equivalent number of H3Stem Cells.

FIG. 8: Other liver-specific activities and markers characterize H2Stem Progeny. Liver carboxylase activity (CES1 activity) has been compared with ADHLSC Cells, reference cell line HepG2, primary hepatocytes, H2Stem Cells, and H3Stem Cells over the indicated period of time (A). Secretion of alpha-Antitrypsin (AAT) has been compared using ELISA between ADHLSC cells and H2Stem Cells (B).

FIG. 10: Cell surface proteins can be used as biomarkers for distinguishing H2Stem Cells from ADHLSC Cells. A cell surface protein named Sushi domain containing protein 2 (SUSD2) is much strongly expressed when protein extracts of H2Stem Cells and ADHLSC are compared by Western Blot, using an anti-SUSD2 antibody and (as a control for the amount of total proteins in the sample) an anti-Beta actin antibody (A). When the analysis is performed by FACS to compare expression of SUSD2 with another cell surface marker such as CD140b and the cut-off point between expressing and non-expressing cells is placed at the intensity where 3% of the cells is positive for the isotype negative control, the difference in SUSD2 expression appears more reduced, especially when comparing CD140b positivity which clearly allow differentiating between low expressing H2Stem Cells and high expressing ADHLSC Cells (B). However, the details on the distribution of signal intensity for the specific fluorophore in positive cells (PE-pos) shows that those ADHLSC Cells expressing SUSD2 actually express it at much lower levels than H2Stem Cells, while CD140b data show that this marker is clearly strongly expressed only in a large majority of ADHLSC Cells.

DETAILED DESCRIPTION OF THE INVENTION

Figure 1:
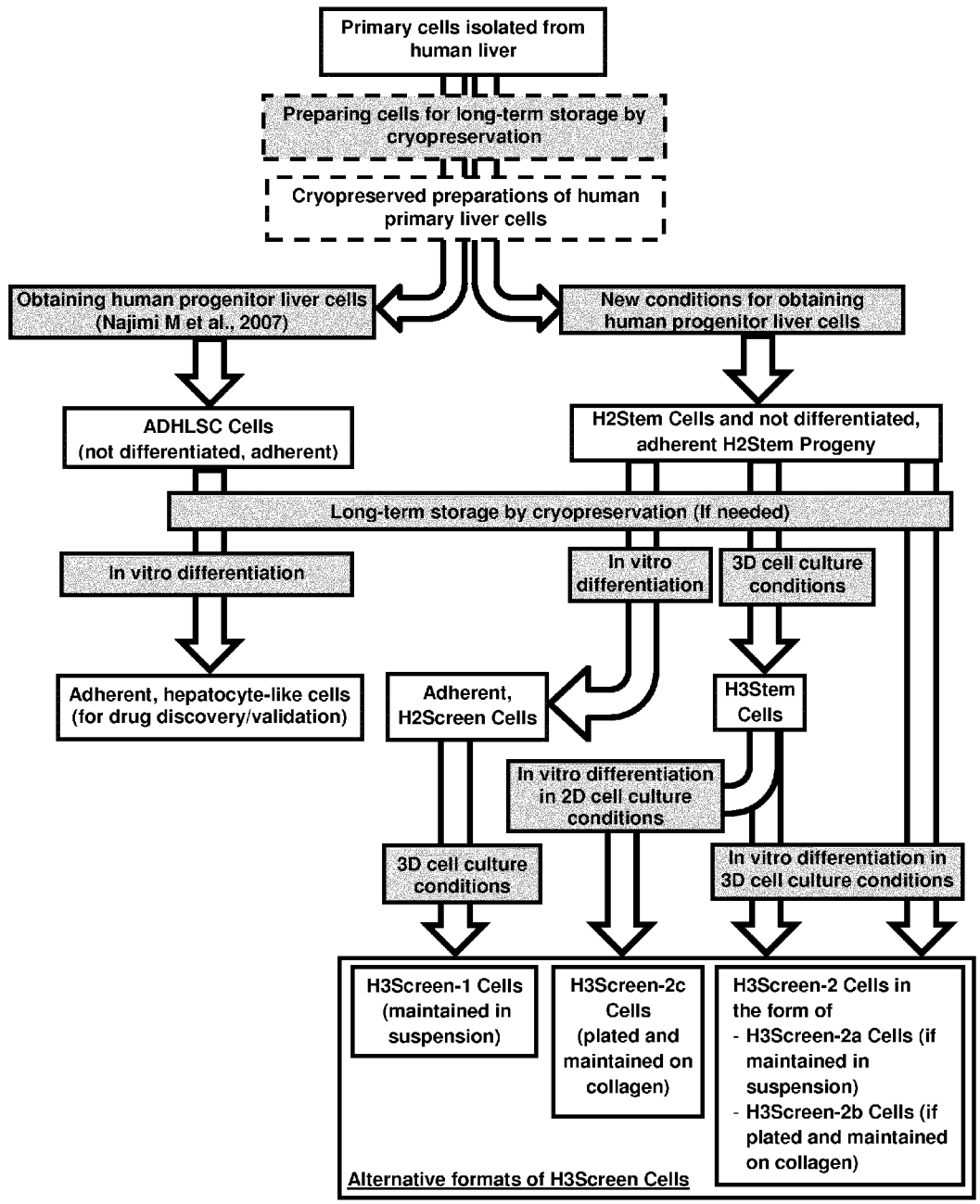
FIG. 1: Flowchart comparing the process for obtaining and using of ADHLSC Cells and H2Stem Cells. Both ADHLSC Cells and H2Stem Cells can be prepared starting from primary cells isolated from human liver that can be used directly or by preparing cryopreserved preparations of human primary liver cells for long-term storage. H2Stem Cells with improved liver-specific features and a cuboidal meso-epithelial morphology can be used for the generating H2Stem Progeny for appropriate in vivo or in vitro applications, in either two-dimensional (2D) or three-dimensional (3D) cell culture conditions (i.e. by maintaining H2Stem Cells and H2Stem progeny as adherent cells or in flasks and other containers with low cell adherence properties, respectively). The three-dimensional H2Stem Progeny are formed by clusters of cells that are characterized by means of specific markers and/or biological activities. Initially, H2Stem Cells can be used for generating, with or without an intermediate expansion as adherent cells (e.g. on a substrate such as collagen), a H2Stem Progeny that is characterized as either differentiated, adherent hepatocyte-like cells (H2Screen Cells) or three-dimensional clusters comprising liver progenitor cells (H3Stem Cells). Each of these two types of H2Stem Progeny can be further used for generating three-dimensional H2Stem Progeny comprising highly metabolically active cells that are defined respectively as H3Screen-1 Cells and H3Screen-2 Cells, according to two alternative protocols for generating them. H3Screen-2 Cells may be also generated directly from H2Stem Progeny (i.e. without the step of obtaining H3Stem Cells) by culturing H2Stem Progeny in three-dimensional conditions and in a cell culture medium providing in vitro, liver-specific differentiation. Depending on the cell culture conditions in which H3Screen Cells are maintained, these cells can form alternative formats of three-dimensional cell clusters in suspension (H3Screen-2a Cells and H3Screen-1 Cells) or as adherent cells (H3Screen-2b Cells and H3Screen-2c Cells). Long-term storage by cryopreservation is applicable to both ADHLSC Cells and H2Stem Cells if needed (i.e. if expansion, differentiation, and/or culturing as three-dimensional H2Stem Progeny is not immediate but applied later on in the process), as well as to a specific H2Stem Progeny in a given structural or differentiation state.

A main embodiment of the invention comprises H2Stem Cells and H2Stem Progeny characterized by novel combinations biological activities and markers that can be identified on their surface, intracellular, and/or secreted in cell culture medium. These features, together with morphological and functional features, were determined in association to the methods for producing H2Stem Cells and H2Stem Progeny in cell culture conditions, defining the positive (or negative) criteria characterizing such cells, in particular for a method comprising:
(a) Disassociating adult liver or a part thereof to form a population of primary liver cells;
(b) Generating preparations of the primary liver cells of (a);
(c) Culturing the cells comprised in the preparations of (b) onto a support which allows adherence and growth of cells thereto and the emergence of a population of cells having cuboidal meso-epithelial morphology;
(d) Passaging the cells of (c) at least once; and
(e) Isolating the cell population that is obtained after passaging of (d) that are positive for at least one hepatic marker and one mesenchymal marker and for at least a liver-specific metabolic activity, and maintain a cuboidal meso-epithelial morphology.

Concerning Step (a) of the method, the dissociation step involves obtaining adult liver or a part thereof that contains, together with fully differentiated hepatocytes, an amount of primary cells that can be used for producing H2Stem Cells. The liver primary cells are preferentially isolated from human liver tissues which can be obtained from adult liver.

The term "liver" refers to liver organ. The term "part of liver" generally refers to a tissue sample derived from any part of the liver organ, without any limitation as to the quantity of the said part or the region of the liver organ where it originates. Preferably, all cell types present in the liver organ may also be represented in the said part of liver. Quantity of the part of liver may at least in part follow from practical considerations to the need to obtain enough primary liver cells for reasonably practicing the method of the invention. Hence, a part of liver may represent a percentage of the liver organ (e.g. at least 1%, 10%, 20%, 50%, 70%, 90% or more, typically w/w). In other non-limiting examples, a part of liver may be defined by weight (e.g. at least 1 g, 10 g, 100 g, 250 g, 500 g, or more). For example, a part of liver may be a liver lobe, e.g., the right lobe or left lobe, or any segment or tissue sample comprising a large number of cells that is resected during split liver operation.

The term "adult liver" refers to liver of subjects that are post-natal, i.e. any time after birth, preferably full term, and may be, e.g., at least at least 1 day, 1 week, 1 month or more than 1 month of age after birth, or at least 1, 5, 10 years or more. Hence, an "adult liver", or mature liver, may be found in human subjects who would otherwise be described in the conventional terms of "infant", "child", "adolescent", or "adult". The liver or part thereof is obtained from a "subject" or "donor", interchangeably referring to a vertebrate animal, preferably a mammal, more preferably a human. In another embodiment, the adult liver or part thereof may be from a non-human animal subject, preferably a non-human mammal subject (e.g. a rodent or pig).

A donor may be living or dead, as determined by clinically accepted criteria, such as the "heart-lung" criteria (involving an irreversible cessation of circulatory and respiratory functions) or the "brain death" criteria (involving an irreversible cessation of all functions of the entire brain, including the brainstem). Harvesting may involve known procedures such as biopsy, resection or excision. Harvesting of liver tissue from a living human donor may need to be compatible with sustenance of further life of the donor. The liver or part thereof may be obtained from a donor, esp. human donor, who has sustained circulation, e.g., a beating heart, and sustained respiratory functions, e.g., breathing lungs or artificial ventilation. Only a part of liver may typically be removed from a living human donor (e.g., by biopsy or resection), such that an adequate level of normal liver functions is maintained in the donor, as required by legal and ethical norms.

Subject to ethical and legal norms, the donor may need to be or need not be brain dead (e.g., removal of entire liver or portion thereof, which would not be compatible with further survival of a human donor, may be allowed in brain dead human beings). Harvesting of liver or part thereof from such donors is advantageous, since the tissue does not suffer substantial anoxia (lack of oxygenation), which usually results from ischemia (cessation of circulation). At the time of harvesting the tissue may have ceased circulation and/or respiratory functions, with no artificial ventilation. While liver or part thereof from these donors may have suffered at least some degree of anoxia, liver from cadaveric donors can be used for obtaining H2Stem Cells in cell culture conditions, for instance within about 1 hour, 3 hours, 6 hours, 12 hours, 24 hours or more after the donors circulation ceased.

The tissues harvested as above may be cooled to about room temperature, or to a temperature lower than room temperature, but usually freezing of the tissue or parts thereof is avoided, esp. where such freezing would result in nucleation or ice crystal growth. For example, the tissue may be kept at any temperature between about 1° C. or about 4° C. and room temperature, and may advantageously be kept at about 4° C., e.g. on ice. The tissue may be cooled for all or part of the ischemic time, i.e., the time after cessation of circulation in the donor. That is, the tissue can be subjected to warm ischemia, cold ischemia, or a combination of warm and cold ischemia. The harvested tissue may be so kept for, e.g., up to 48 hours before processing, preferably for less than 24 hours, e.g., more preferably for less than 12 hours (e.g., less than 6, 3, or 1 hour). The harvested tissue may advantageously be but need not be kept in, e.g., completely or at least partly submerged in, a suitable medium and/or may be but need not be perfused with the suitable medium, before further processing of the tissue. A skilled person is able to select a suitable medium which can support the survival of the cells of the tissue during the period before processing.

The method of the invention comprises disassociating adult liver tissue as described above to form a population of primary cells. The term "disassociating" as used herein generally refers to partly or completely disrupting the cellular organization of a tissue or organ, i.e., partly or completely disrupting the association between cells and cellular components of a tissue or organ, to obtain a suspension of cells (a cell population) from the said tissue or organ. The suspension may comprise solitary or single cells, as well as cells physically attached to form clusters or clumps of two or more cells. Disassociating preferably does not cause or causes as small as possible reduction in cell viability. A suitable method for disassociating liver or part thereof to obtain a population (suspension) of primary cells therefrom may be any method well known in the art, including but not limited to, enzymatic digestion, mechanical separation, filtration, centrifugation and combinations thereof. In particular, the method for disassociating liver or part thereof may comprise enzymatic digestion of the liver tissue to release liver cells and/or mechanical disruption or separation of the liver tissue to release liver cells.

Methods for disassociating liver or part thereof as above are documented in the literature as the widely used collagenase perfusion technique in two or more steps, which has been variously adapted and modified for performing it with whole livers or segments of liver. The liver tissue is perfused with a divalent cation-free buffer solution, preheated at 37° C., containing a cation-chelating agent (e.g. EDTA or EGTA). Buffer solutions can comprise salt solutions (e.g. HEPES, Williams E medium) or any other balanced salt solution that can also include salts such as NaCl and KCl, among others. This leads to disruption of the desmosomal structures that hold cells together. The tissue is then perfused with the buffer solution containing divalent cation(s), such as Ca2+ and Mg2+, and matrix-degrading enzymes that act to digest the tissue.

The primary liver cells are usually released by gentle mechanical disruption and/or pressing through filters, to mechanically complete the cell dissociation process. Such filters may have sieve sizes that allow passage of cells through about 0.1 mm, 0.25 mm, 0.50 mm, 1 mm or more. A succession of filters with progressively smaller sieve sizes may be used to gradually disassociate the tissue and release cells. The dissociated cells are rinsed with a buffer containing protease inhibitor, serum and/or plasma to inactivate collagenase and other enzymes used in the perfusion process, and then separated from the mixture by pelleting them with low speed centrifugation (e.g. at between 10×g and 500×g). Most of, if not all, viable cells can be pelleted, while dead cells and cell debris are substantially eliminated and subsequently are washed with ice-cold buffer solution to purify the cell suspension. The number and quality of the primary liver cells can vary depending on the quality of the tissue, the compositions of different solutions that are used, and the type and concentration of enzyme. The enzyme is frequently collagenase but also pronase, trypsin, hyaluronidase, thermolysin, and combinations thereof can be used. Collagenase may consist of a poorly purified blend of enzymes and/or exhibit protease activity, which may cause unwanted reactions affecting the quality and quantity of viable cells that can in turn be avoided by selecting enzyme preparations of sufficient purity and quality. Other methods of harvesting primary liver cells may exclude enzymatic digestion techniques and may involve perfusing liver with solutions containing sucrose followed by mechanical disruption.

Concerning Step (b) of the method, the preparation of liver primary cells that is obtained following the disassociation of liver tissue may typically be a heterogeneous population of primary liver cells, comprising cells belonging to any liver-constituting cell types, including progenitor or stem cells, that may have been present in liver parenchyma and or in non-parenchyma thereof. Exemplary liver-constituting cell types include hepatocytes, cholangiocytes, Kupffer cells, hepatic stellate cells, and liver endothelial cells, in addition to stem or progenitor cells.

The term "hepatocyte" encompasses epithelial, parenchymal liver cells, including but not limited to hepatocytes of different sizes or ploidy (e.g., diploid, tetraploid, octaploid).

The term "primary cell" includes cells present in a suspension of cells obtained from a tissue or organ of a subject, e.g. liver, by disassociating cells present in such explanted tissue or organ with appropriate techniques.

The methods of the Invention may preferably start from a cell population representative of most, if not all, liver cell types at the scope of obtaining the desired adult liver progenitor cells in cell culture conditions. A suitable starting cell population for obtaining H2Stem Cells may comprise hepatocytes in different proportions (0.1%, 1%, 10%, or more of total cells), according to the method of disassociating liver and/or any methods for fractioning or enriching the initial preparation for hepatocytes and/or other cell types on the basis of physical properties (dimension, morphology), viability, cell culture conditions, or cell surface marker expression by applying any suitable techniques.

The population of primary cells as defined and obtained herein by disassociating liver (or part of it) can be used immediately for establishing cell cultures as fresh primary liver cells or, preferably, stored as cryopreserved preparations of primary liver cells using common technologies for their long-term preservation. Indeed, the use of cryopreserved cell preparations appears having a positive effect on the efficiency with which H2Stem Cells and H2Stem Progeny are later produced in cell culture. Cells in these samples may be frozen in a cell culture medium or a solution for preserving cells or organs (e. g. Viaspan, Cryostor, Celsior) that is supplemented or not with other compounds such as growth factors, serum, buffer solutions, Glucose, Albumin, ethylene glycol, sucrose, dextrose, DMSO or any other cryoprotectant. Each cryopreserved preparation may contain at least $10^3$, $10^4$, $10^5$, $10^6$, $10^7$, $10^8$ cells or more per cryovial or bag, at scope of producing and isolating higher amount of H2Stem Cells in cell culture conditions after appropriately thawing the sample and, if needed, washing the cells with appropriate buffer or cell culture medium for eliminating residual cell culture medium or a solution for preserving cells or organs.

Concerning Step (c) of the method, the preparation of liver primary cells can be cultured directly onto a fully synthetic support (e.g. plastic or any polymeric substance) or a synthetic support pre-coated with feeder cells, protein extracts, or any other material of biological origin that allow the adherence and the proliferation of similar primary cells and the emergence of a population of adult liver progenitor cells having a cuboidal meso-epithelial morphology. Preferably cells from the primary cell population that have adhered to the said substrate, are cultured for at least 7 days, preferably at least 10, or at least 12 days. More preferably, the cells from the primary cell population are cultured within 7 and 12 days, to obtain a population of adherent cells that is sufficiently enriched for viable that can provide H2Stem Cells.

The term "culturing" broadly refers to conditions for the maintenance and/or growth of cells, and in particular of H2Stem and/or of H2Stem Progeny in cell culture. Elements such as the support where cells are cultured and allowing cell adhesion (or, when needed, allowing growth of cell clusters in suspension), composition of cell culture medium, density at which the cells are seeded and maintained, the $O_2$ and $CO_2$ concentration, may be adapted for culturing H2Stem Cells and H2Stem Progeny, as detailed below in the Detailed Description and in the Examples.

The term "liver progenitor cell" refers to an unspecialized and proliferation-competent cell which is produced using by culturing cells that are isolated from liver and which or the progeny of which can give rise to at least one relatively more specialized cell type. A liver progenitor cell give rise to descendants that can differentiate along one or more lineages to produce increasingly more specialized cells (but preferably hepatocytes or hepato-active cells), wherein such descendants may themselves be progenitor cells, or even to produce terminally differentiated liver cells (e.g. fully specialized cells, in particular cells presenting morphological and functional features similar to those of primary human hepatocytes).

Given that the liver tissues that are used in the Methods of the invention come from adult liver, H2Stem Cells can be defined as adult liver progenitor cells, having a cuboidal meso-epithelial morphology with large and transparent cytoplasm, irregular membrane without protrusions, developing intercellular contacts and junctions, and displaying growth contact inhibition. Following emergence and proliferation as adherent colony or clusters of cells (see FIG. 3), H2Stem Cells can be further characterized by technologies that allow detecting relevant markers already at this stage (that is, before passaging cells as indicated in step (d)) and that were initially characterized at a later stage, as described below at step (e) as being one hepatic marker and at least one mesenchymal marker, and at least one liver-specific activity.

Among the technologies for identifying such markers and measuring them as being positive or negative, immunocytochemistry or analysis of cell culture media are preferred since allowing marker detection even with the low amount of H2Stem Cells that are available at this step, without destroying them (as it would be in the case of Western Blot or Flow Cytometry). In particular, the detection of Cytokeratin-19-positive cells (as shown in FIG. 2B), or of secreted liver proteins, including albumin or enzymes like alpha-1-antitrypsin (see FIG. 8B), can be performed at this stage, together or not the detection of other relevant markers as described below, including cell surface protein (such as SUSD2, CD90, CD73, CD29, CD44, and/or liver-specific transporters), intracellular proteins (such as Vimentin or ASMA), and hepatic enzymes and related activities (such as liver carboxylase, tyrosine transferases, tryptophan-2,3-dioxygenase, urea secretion, CYP3A4 or any other phase I cytochrome P450 activities).

H2Stem Cells emerge from primary population of liver cells that is plated onto a substrate allowing adherence of cells within an in vitro environment capable of promoting survival and/or growth of such cells. This environment may prevent an undesired exchange of matter between the said environment (i.e. the cell culture container) and the surroundings (e.g. by avoiding contamination of the laboratory environment), while it can allow continuous or intermittent exchange of other, useful, components between culture vessels (e.g. by an occasional exchange of a part or all of the culture medium, the continuous exchange of gases).

The culture vessels can be cell culture flasks, bottles, well plates, bioreactors and dishes of various formats but displaying one or more substrate surfaces compatible with cell adhesion, such that the plated cells can contact this substrate to be maintained adherent cell cultures. In general, a substrate which allows adherence of cells thereto may be any substantially hydrophilic substrate, being glass or a synthetic polymeric material (such as polycarbonates, polystyrenes, polyorthoesters, polyphosphazenes, polyphosphates, polyesters, nylons or mixtures thereof) that are generally shaped and treated in order to provide hydrophilic substrate surfaces and thereby enhance the likelihood of effective cell attachment (as shown in the Examples by using CellBind commercial materials). Surface treatment may take the form of a surface coating, or may involve generating chemical groups on the polymer surface that have a general affinity for water or otherwise exhibit sufficient polarity to permit stable adsorption to another polar group. These functional groups lead to hydrophilicity and/or an increase in surface oxygen and are properties recognized to enhance cell growth on so modified substrate surfaces. Such chemical groups may include groups such as amines, amides, carbonyls, carboxylates, esters, hydroxyls, or sulfhydryls that can be also introduced by treating them with specific wave frequency-based technologies.

Cell adhesion can be facilitated by coating the treated plastic surfaces with a layer of matrix. The coating may involve suitable polycations (e.g., polyomithine or polylysine) or, preferably, one or more components of extracellular matrix: fibrin, laminin, non-/fibrous collagens (preferably collagen type 1), glycosaminoglycans (e.g., heparin or heparan sulphate) or proteins such as fibronectin, gelatine, vitronectin, elastin, tenascin, aggrecan, agrin, bone sialoprotein, cartilage matrix protein, fibrinogen, fibulin, mucins, entactin, osteopontin, plasminogen, restrictin, serglycin, osteonectin, versican, thrombospondin 1, or cell adhesion molecules including cadherins, connexins, selectins, by themselves or in various combinations. Preferred examples may include collagen compositions, comprising or not other extracellular matrix components). Alternatively, synthetic peptides that are fragments or otherwise derived from the proteins listed above, gels, molecular scaffolds and other three-dimensional structures that are formed from synthetic and/or biological materials can be used in this scope.

The primary cell suspension may be contacted with the adherent surface for a period of time (e.g. at least 2, 4, 6, 12, 24 hours, or more) that is sufficient for allowing the primary liver cell populations to attach to adherent substrate, before removing any non-adherent matter from the culture system (e.g., non-viable or dead cells and cell debris) by discarding medium from the culture system and optionally washing, once or repeatedly, the adherent cells. Then, the culture system is provided with any suitable medium or isotonic buffer (e.g., PBS). Hereby, cells from the primary liver cell population, which have adhered to the surface, are selected for further culturing and may be counted in order to evaluate the plating density that may be expressed as number of cells plated per $cm^2$ of the said surface (e.g. between 10 and $10^5$ cells/$cm^2$).

The preparation of primary cells, directly at plating or after washing the cells, is maintained in a liquid medium, which supports their survival and/or growth of the cells. The medium may be added to the system before, together with or after the introduction of the cells thereto. The medium may be fresh (i.e., not previously used for culturing of cells) or may comprise at least a fraction which has been conditioned by prior culturing cells of liver origin (or of any other origin) therein. In particular, the medium may be any suitable culture medium for culturing liver progenitor cells as described in the literature and it may be regularly exchanged (e.g., each hour, 3 hours, 12 hours, 24 hours or more) with a fresh medium presenting the same or a different features (e.g. composition, pH). The whole volume of the medium may be changed or, alternatively, only part of the medium may be changed, such that a fraction of the medium conditioned by the previous culturing of the cells is retained. Alternatively, the medium is not exchanged until the cells are transferred into another culture vessel, prolonging the culture of the cells in a way that most of the cells not of interest (e.g. hepatocytes and other fully differentiated cells of liver origin) are detached and die, and fresh medium may be simply added regularly.

The adherent, primary cells are cultured in the presence of a liquid culture medium. for growing adherent cells that is based on defined chemical media with addition of bovine, human or other animal serum that, besides providing nutrients and/or growth promoters, may also promote the growth/adherence or the elimination/detachment of specific cell types.

Basal media formulations (available, e.g., from the American Type Culture Collection, ATCC; or from Invitrogen, Carlsbad, Calif.) can be used to culture the primary cells herein, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of these basal media and criteria to adapt concentrations of media and/or media supplements as necessary for the cells cultured are generally known. A preferred basal medium formulation may be those available commercially such as Williams Medium E, IMDM or DMEM, which are reported to sustain in vitro culture of adult liver cells.

Such basal media formulations contain ingredients necessary for mammal cell development, which are known per se such as inorganic salts (in particular salts containing Na, K, Mg, Ca, CI, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g. glucose, pyruvate). Additional supplements can be used to supply the cells with the necessary trace elements and substances for optimal growth and expansion. Such supplements include insulin, transferrin, selenium salts, and combinations thereof. These components can be included in a salt solution such as Hanks' Balanced Salt Solution (HBSS), Earle's Salt Solution. Further antioxidant supplements may be added, e.g. β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds. Most importantly, cell culture media can be complemented with mammalian plasma or sera that contain cellular factors and components that are necessary for cell viability and expansion and that, under certain condition, may be replaced with synthetic components.

The term "serum", as conventionally defined, is obtained from a sample of whole blood by first allowing clotting to take place in the sample and subsequently separating the so formed clot and cellular components of the blood sample from the liquid component (serum) by an appropriate technique, typically by centrifugation. An inert catalyst, e.g., glass beads or powder, can facilitate clotting. Advantageously, serum can be prepared using serum-separating vessels (SST), which contain the inert catalyst to mammals.

The serum or plasma may be obtained commercially and from an organism of the same species as is the species from which the primary liver cells are obtained. Human serum or plasma may be used for culturing primary human liver cells. Alternatively, the medium comprises bovine serum or plasma, preferably foetal bovine (calf) serum or plasma, more preferably foetal bovine (calf) serum (FCS or FBS). The medium comprises between about 0.5% and about 40% (v/v) of serum or plasma or serum replacement, preferably between about 5% and 20% (v/v), e.g., between about 5% and 15% (v/v), e.g. about 10% (v/v). A medium for culturing human liver cells may comprise a mixture of human plasma or serum, preferably human serum, and bovine plasma or serum, preferably bovine serum.

Prior to storage or use, the plasma or serum can be irradiated (e.g. gamma-irradiated) or heat inactivated. Heat inactivation is used in the art mainly to remove the complement. Heat inactivation typically involves incubating the plasma or serum at 56° C. for 30 to 60 minutes, e.g., 30 minutes, with steady mixing, after which the plasma or serum is allowed to gradually cool to ambient temperature. Optionally, the plasma or serum may also be sterilized prior to storage or use (e.g. by filtration through one or more filters with pore size smaller than 1 μm).

Ordinary components of basal media (before addition of serum or plasma), e.g., in particular, isotonic saline, buffers, inorganic salts, amino acids, carbon sources, vitamins, antioxidants, pH indicators and antibiotics, are not considered growth factors or differentiation factors in the art. On the other hand, serum or plasma is a complex composition possibly comprising one or more such growth factors.

The term "growth factor" as used herein refers to a biologically active substance which influences proliferation, growth, differentiation, survival and/or migration of various cell types, and may effect developmental, morphological and functional changes in an organism, either alone or when modulated by other substances. A growth factor may typically act by binding, as a ligand, to a receptor (e.g., surface or intracellular receptor) present in cells. A growth factor herein may be particularly a proteinaceous entity comprising one or more polypeptide chains. The term "growth factor" encompasses the members of the fibroblast growth factor (FGF) family, bone morphogenic protein (BMP) family, platelet derived growth factor (PDGF) family, transforming growth factor beta (TGF-beta) family, nerve growth factor (NGF) family, the epidermal growth factor (EGF) family, the insulin related growth factor (IGF) family, the hepatocyte growth factor (HGF) family, the interleukin-6 (IL-6) family (e.g. oncostatin M), hematopoietic growth factors (HeGFs), the platelet-derived endothelial cell growth factor (PD-ECGF), angiopoietin, vascular endothelial growth factor (VEGF) family, or glucocorticoids. Where the method is used for human liver cells, the growth factor used in the present method may be a human or recombinant growth factor. The use of human and recombinant growth factors in the present method is preferred since such growth factors are expected to elicit a desirable effect on cellular function The medium may comprise a combination of serum or plasma with one or more exogenously added growth factors as defined above, preferably at concentrations in which particular growth factors can induce an effect on in vitro cultured cells. For example, the medium may comprise EGF and insulin, or EGF and dexamethasone, or insulin and dexamethasone, or each EGF, insulin and dexamethasone. EGF may be typically used at concentrations between about 0.1 ng/ml and 1 μg/ml and preferably between 1 ng/ml and 100 ng/ml, e.g., at about 25 ng/ml; insulin can be typically used at concentrations between about 0.1 μg/ml and 1 mg/ml and preferably between about 1 μg/ml and 100 μg/ml, e.g., at about 10 μg/ml; dexamethasone can be typically used at concentrations between about 0.1 nM and 1 μM, preferably between about 1 nM and 100 nM, e.g., at about 10 nM.

Hormones can also be used in cell culture, for example D-aldosterone, diethylstilbestrol (DES), dexamethasone, insulin, estradiol, hydrocortisone, prolactin, progesterone, hyrotropin, thyroxine, L-thyronine. Liver cells can also benefit from culturing with triiodithyronine, α-tocopherol acetate, and glucagon. Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

The morphological and phenotypic features of H2Stem Cells described in the Examples may allow obtaining such cells not only when cryopreserved preparations of primary liver cells have low plating efficiency, but also by testing and/or adapting known technologies for preparing adherent cells from heterogeneous preparations of primary cells by selecting and combining different technologies, conditions, and/or materials (e.g. the synthetic polymeric material, the component(s) of extracellular matrix, the cell culture medium, the amount or oxygen and/or $CO_2$ in the incubator, the washing buffer, etc.). In particular, culturing in hypoxic conditions (as obtained by adding an anti-oxidant compound at millimolar or lower concentrations), together with one or more combinations of these other elements can be applied in order to obtain H2Stem Cells in greater amount and/or more quickly from cell culture.

This step of culturing of primary liver cells as defined above leads to emergence and proliferation of H2Stem Cells in the culture and can be continued until H2Stem Cells have proliferated sufficiently. For example, the said culturing can be continued until the cell population achieved a certain degree of confluence (e.g., at least 50%, 70%, or at least 90% or more confluent). The term "confluence" as used herein refers to a density of cultured cells in which the cells contact one another, covering substantially all of the surfaces available for growth (i.e., fully confluent).

Concerning Step (d) of the method, primary cells are cultured in a cell culture medium sustaining their adherence and the proliferation of and the emergence of a homogenous cell population that, following at least one passage, is progressively enriched for H2Stem Cells. H2Stem Cells can be rapidly expanded for generating sufficient cells for obtaining H2Stem Progeny having the desired properties (e.g. as bi-dimensional adherent cells or three-dimensional cell clusters, at a given density and/or differentiation status), with cell doubling that can be obtained within 48-72 hours and maintenance of H2Stem Progeny having the desired properties for at least for 2, 3, 4, 5 or more passages.

When passaged, the cultured cells are detached and dissociated from the culture substrate and from each other. Detachment and dissociation of the cells can be carried out as generally known in the art, e.g., by enzymatic treatment with proteolytic enzymes (e.g., chosen from trypsin, collagenase, e.g., type I, II, III or IV, dispase, pronase, papain, etc.), treatment with bivalent ion chelators (e.g., EDTA or EGTA) or mechanical treatment (e.g., repeated pipetting through a small bore pipette or pipette tip), or any combination of these treatments.

A suitable method of cell detachment and dispersion should ensure a desired degree of cell detachment and dispersion, while preserving a majority of cells in the culture. Preferably, the detachment and dissociation of the cultured cells would yield a substantial proportion of cells as single, viable cells (e.g., at least 50%, 70%, 90% of the cells or more). The remaining cells may be present in cell clusters, each containing a relatively small number of cells (e.g., on average, between 1 and 100 cells).

Next, the so detached and dissociated cells (typically as a cell suspension in an isotonic buffer or a medium) may be re-plated onto a substrate which allows the adherence of cells thereto, and are subsequently cultured in a medium as described above sustaining the further proliferation of H2Stem Cells and of H2Stem Progeny. These cells may be then cultured by re-plating them at a density of between 10 and $10^5$ cells/cm$^2$, and at a splitting ratio between about 1/16 and 1/2, preferably between about 1/8 and 1/2, more preferably between about 1/4 and 1/2. The splitting ratio denotes the fraction of the passaged cells which is seeded into an empty (typically a new) culture vessel of the same surface area as the vessel from which the cells were obtained. The type of culture vessel, as well as of surface allowing cell adherence into the culture vessel and the cell culture media, can be the same as initially used and as described above, or may be different. Preferably, cells are maintained onto CellBind or any other appropriate support that is coated with extracellular matrix proteins (such as collagens, and preferably collagen type I) or synthetic peptides.

Concerning step (e) above, the isolation of population of H2Stem Cells applies to cells that have maintained a cuboidal meso-epithelial morphology, that are positive for at least one hepatic marker and at least one mesenchymal marker, and that have at least one liver-specific activity, further validating the criteria for initially identifying H2Stem Cells at step (c) above but that can be more easily established given the higher amount of cells that are available after passaging.

The terms "isolating" or "isolation" refers to both the physical identification and the isolation of a cell population from a cell culture or a biological sample that can be performed by applying appropriate cell biology technologies that are either based on the inspection of cell cultures and on the characterization (and physical separation when possible and desired) of cells corresponding to the criteria, or on the automated sorting of cells according to the presence/absence of antigens and/or cell size (such as by FACS). In some embodiments, the terms "isolating" or "isolation" may comprise a further step of physical separation and/or quantification of the cells, especially by carrying out flow cytometry.

The terms "cell population" and "population of cells" refer generally to a group of cells. Unless indicated otherwise, the term refers to a cell group consisting essentially of or comprising cells as defined herein. A cell population may consist essentially of cells having a common phenotype or may comprise at least a fraction of cells having a common phenotype. Cells are said to have a common phenotype when they are substantially similar or identical in one or more demonstrable characteristics, including but not limited to morphological appearance, the level of expression of particular cellular components or products (e.g., RNA or proteins), activity of certain biochemical pathways, proliferation capacity and/or kinetics, differentiation potential and/or response to differentiation signals or behavior during in vitro cultivation (e.g., adherence or monolayer growth). Such demonstrable characteristics may therefore define a cell population or a fraction thereof. A cell population may be "substantially homogeneous" if a substantial majority of cells have a common phenotype. A "substantially homogeneous" cell population may comprise at least 60%, e.g., at least 70%, at least 80%, at least 90%, at least 95%, or even at least 99% of cells having a common phenotype, such as the phenotype specifically referred to H2Stem Cells (or to H2Stem Progeny). Moreover, a cell population may consist essentially of cells having a common phenotype such as the phenotype of H2Stem Cells (i.e. an H2Stem Progeny) if any other cells present in the population do not alter or have a material effect on the overall properties of the cell population and therefore it can be defined as a cell line.

In general, any technology for identifying and characterizing cellular markers for a specific cell type (e.g. mesenchymal, hepatic, hematopoietic, epithelial, endothelial markers) or having a specific localization (e.g. intracellular, on cell surface, or secreted) that are published in the literature may be considered appropriate for characterizing H2Stem Cells and H2Stem Progeny. Such technologies may be grouped in two categories: those that allow maintaining cell integrity during the analysis, and those based on extracts (comprising proteins, nucleic acids, membranes, etc.) that are generated using such cells. The Examples contain data on how such technologies have been used for characterizing H2Stem Cells and H2Stem Progeny, e.g. by performing an analysis of the presence of cell surface antigens before performing a more detailed and comparative analysis with other liver progenitor cells or adult liver primary cells in order to assess their distinctive features and biological activities.

At the protein level, technologies such as flow cytometry, FACS, or immunocytochemistry, allow determining the presence/absence of surface or intracellular proteins in H2Stem Cells by using antibodies or other protein-specific reagents. Flow cytometry is a preferred technology for characterizing cell populations according to the combined presence/absence of surface, or intracellular markers, as determined by single or multiple staining techniques, and/or size and granularity evaluation. Immunocytochemistry also provides relevant information regarding the morphological features that are associated to the combined presence/absence of surface, cytoskeletal, and/or other intracellular markers. In fact, the Examples show that, in some embodiments, a significant percentage of cells in a preparation of H2Stem Cells is positive for cytokeratin-19, (CK-19) a cytoskeletal and intracellular marker. This percentage may be estimated as being at least 20% or between 20 and 40% when detected by flow cytometry but it can be much higher (i.e. up to 90% or more) when CK-19 is detected by immunocytochemistry (see FIG. 2B). This further feature (i.e. positivity to CK-19) allows establishing and identifying a cell population that is produced by culturing primary liver cells as H2Stem Cells.

In particular, the presence of at least one mesenchymal marker (in particular selected from ASMA Vimentin, CD90, CD 73) and of at least one hepatic marker should be measured by flow cytometry, immunocytochemistry, or any other technique (generally making use of antibodies, lectins, or other proteins and not requiring the protein or nucleic acid extraction) that allows evaluating the percentage of cells presenting the receptor. Positivity by flow cytometry and immunocytochemistry is here defined when at least 60% of cells present the desired marker or receptor (as shown in the Examples). Similarly, the negativity by flow cytometry and immunocytochemistry is here defined when less than 20% of cells present the given marker or receptor (as shown in the Examples). In some embodiments, less than 10% of cells present a given negative marker, as in the case of CD140b (see FIG. 10B).

In some embodiments, when measuring a given marker, the agent that is used for detection of a marker as defined above or a cell surface protein is immobilized on a solid phase (e.g. a bead, a plate, or a biomaterial), labeled (e.g. fluorescently labeled), and/or recognized by another compound that is labeled (e.g. a secondary antibody). There are numerous methods by which the label can produce a signal detectable by external means, for example, desirably by visual examination or by electromagnetic radiation, heat, and chemical reagents. The label or other signal producing system component can also be bound to a specific binding partner, another molecule or to a support such as beads, using any method known in the art, such as chemically cross-linking or using the biotin-streptavidin system. The label can directly produce a signal, and therefore, additional components are not required to produce a signal. Numerous organic molecules, for example fluorochromes (such as FITC, PE, PC5, PC7, APC, or any other known to be compatible with flow cytometry), absorb ultraviolet and visible light. Other types of label directly produce a signal, such as radioactive isotopes and dyes. Alternatively, the label may need other components to produce a signal, and the signal producing system would then include all the components required to produce a measurable signal, which may include substrates, coenzymes, metal ions, or substances that react with enzymatic products (e.g. chemiluminescent detection of Horseradish Peroxidase).

The liver-specific metabolic activities of H2Stem Cells comprise biological activities generally associated with liver cells (and to hepatocytes in particular) and that distinguish liver cells from cells present in other tissues, and in particular comprise activities involving binding, activation, and/or degradation of proteins or other substrates as described in the literature and in the Examples. These biological activities are established on the basis of the detection of liver-specific metabolic activities that can be protein/drug binding activities and, more preferably, enzymatic activities on given substrates, or in association to liver-specific molecules that are detected by blotting technologies (Western, or Northern blot), sequencing, isoelectrofocusing, ELISA, or of the internalization of synthetic or natural compounds known to be specifically transported and metabolized within liver cells.

At the nucleic acid level, whole genome sequencing, PCR, or RT-qPCR can be used to characterize H2Stem Cells or H2Stem Progeny. Hereby, real time PCR can be used to quantify the expression of the gene under investigation, based on the number of cycles and having it normalized against the cycles obtained for 1 or more endogenous controls. In particular, the RT-PCR reaction can be performed using H2Stem Cells and appropriate primers and buffers but the number of cycle to obtain a signal should not superior to 25, 30 or 35 cycles.

At the activity level, the presence of a liver-specific metabolic activity can be measured by any appropriate technique that allows evaluating the presence and/or the level of activity of liver-specific enzymes, but preferably should allow quantifying in vitro the actual enzymatic activity, with a given limit of detection of the specific end-product (as it can be easily established with the support of literature and commercially available products) for measuring CYP450 activities, detoxification, glycogen storage, secretion of Alpha1-Antitrypsin or albumin, bile production, thrombopoietin production, angiotensinogen production, conversion of ammonia to urea, cholesterol synthesis, glycogenolysis, glycogenesis and lipogenesis. In particular, the positivity for at least a liver-specific metabolic activity is here defined when the activity is measured as being statistically superior to the limit of detection of the end-product (being at least twice, five times, or ten times more than the limit of detection) or approaching the level of activity of primary hepatocytes (superior, identical or 10%; 25%, 50%, 75%, or 90% lower).

The literature provides extensive description of the technologies for evaluating cytochrome P450 activities in human hepatocytes in vitro, in particular regarding the compounds specifically inducing an enzyme activity and the formats that can be used for performing these experiments (Baudoin R et al., 2012; Gerets H H et al., 2012; Gomez-Lechon M J et al., 2012; Halladay J S et al., 2012; Hoffmann S A et al., 2012; Lubberstedt M et al., 2011; Smith C M et al., 2012). Among the different inducers, drug metabolism in these cells can be assessed using midazolam, ethoxyresorufin, benzoxyresorufin, bupropion, Phenacetin, Diclofenac, tolbutamide, phenobarbital, rifampicin, caffeine, beta-naphthoflavone, omeprazole, dextromethorphan, 3-methylcholanthrene, repaglinide, or other known cyto/hepatotoxic compounds as probes. Metabolite detection and quantification can be associated to the activity of hepatic enzymes on specific compounds such as CYP1A2 (by detecting paraxanthine or acetaminophen), CYP3A4 (by detecting 1-OH-midazolam or omeprazole sulfone), CYP2C6 (by detecting HO-Bupropion), CYP2C8 (by detecting hydroxyl-repaglinide), CYP2C9 (by detecting 4'HO-Diclofenac), CYP2C19 (by detecting hydroxy-omeprazole or HO-Mephenytoin), CYP2D6 (by detecting dextrorphan), CYP2E1 (by detecting 6-OH-chlorzoxazone), as well as for other major cytochrome P450 activities such as CYP1A2, CYP2A6, CYP1B1, CYP2B6, CYP3A5, CYP3A7, or CYP7A1 (singularly or in appropriate combinations).

Other enzymes whose expression or (preferably) activity can be established in H2Stem Cells and H2Stem Progeny are UDP-glucuronosyltransferases (such as UGT1A1, UGT2B4, UGT2B7), sulfotransferases (catalyzing the sulfate conjugation of several pharmacologically important endogenous molecules and xenobiotics), tyrosine transferases, tryptophan-2,3-dioxygenase (TDO2 or TDO), indoleamine-2,3-dioxygenases (IDO1 or IDO2), lysyl oxidase (LOX), glutathione S-transferases (e.g. GSTalpha), multidrug resistance proteins (MDR or MRP-1/-2/-3), liver-specific transporters (such as OATP1B1), and other phase I/II/III biotransformation enzymes. Moreover albumin/urea production and secretion, ammonia metabolism, glycogen storage, bile production, thrombopoietin/angiotensinogen production, and galactose/sorbitol elimination rates can be also observed and compared by applying well established protocols.

When a preparation of H2Stem Cells is obtained by the methods of the invention, this cell population can be either maintained and/or propagated in conditions that allow growth and doubling without differentiation or, after one or more passaging in this status, induced to differentiate into hepatocyte-like or hepato-active cells (see FIG. 1, FIG. 4A, and FIG. 5B-E). In both cases, the resulting cells represent H2Stem Progeny. In the first case, the conditions for maintaining H2Stem Cells as undifferentiated H2Stem Progeny may be the same conditions used for obtaining the original population of H2Stem Cells with the purpose of increasing the number of available cells or, as shown in the Examples, generating three-dimensional cell clusters (H3Stem Cells). In the second case, well established cell culture conditions for differentiating adult liver progenitor cells into cells having morphological, biological, functional features typical of cells differentiating into hepatocytes can be applied.

Following step (e) of the methods of the invention, an optional further step (f) may comprise maintaining H2Stem Cells into cell culture conditions allowing the differentiation into cells presenting liver-specific activities, being for instance hepatocyte-like or hepato-active cells (that is, adult liver progenitor cells that have lost their positivity to most, if not all, mesenchymal markers and are positive for most, if not all, morphological, biological and functional features of hepatocytes). The Examples provide details on how to generate such hepatocyte-like or hepato-active cells as H2Stem Progeny in the form of adherent cells (as H3Screen-2b, H3Screen-2c, or H2Screen Cells) or three-dimensional cell clusters that can be easily maintained into suspension (as H3Screen-1 Cells or as H3Screen-2a Cells).

On this latter aspect, the Examples show that Ultra-Low Attachment cell culture plates or flasks, and even more appropriately Ultra-Low Attachment, U-shaped/round culture microplates, provide three-dimensional H2Stem Progeny as cell clusters in suspension showing improved functional and structural features that characterize hepatocytes, and in general hepato-active cells. The U-shaped/round culture microplates comprising 96 or 384 wells (or in any other available format containing a different number of wells with U-shaped bottom and allowing to maintain cell cultures in a volume of cell culture medium below 0.5 ml or, even better, below 0.25 ml) provide three-dimensional H2Stem Progeny as cell clusters in suspension with a more regular size and shape that makes them more appropriate for in vitro and in vivo uses.

Thus, the cell population that is produced and isolated in Step (e) above may, in some embodiments, be maintained in cell culture conditions allowing the formation of cell clusters that represent specific three-dimensional H2Stem Progeny. This step of the method may be as a further Step (g) (e.g. for obtaining H3Screen-1 Cells from H2Screen Cells), as an alternative Step (f1) (e.g. for obtaining H3Stem Cells from H2Stem Cells), or as further alternative Step (f2) that combines in vitro differentiation and formation of three-dimensional H2Stem Progeny (e.g. for obtaining H2Screen-2a Cells directly from H2Stem Cells).

The additional passages (e.g., cell detachment and dispersion, re-plating, etc.) and culturing (e.g., medium addition or changes following confluence, etc.) may be performed at conditions substantially identical or analogous to those of the first passage, as described above or including modifications which would be suggested in the literature and/or for the specific use of H2Stem Cells or H2Stem Progeny, in particular in the form of three-dimensional cell clusters (three-dimensional H2Stem Progeny). Thus, the conditions for maintaining and/or differentiating H2Stem Cells or H2Stem Progeny in cell culture may be further optimized according to different criteria such as timing/medium for the differentiation into hepatocyte-like or hepato-active cells, systems for maintaining three-dimensional cell cultures as cell suspensions, use of specific substrates or scaffolds, hypoxia, combined or sequential addition of growth factors and chemical compounds within cell culture medium, or cell density.

The methods of the Invention provide H2Stem Cells, presenting morphological, protein expression, and functional features that are distinct from those identified in previously described adult progenitor liver cells. Consequently, H2Stem Cells that are obtained or obtainable by the methods defined above represent a further embodiment of the Invention. These methods allow providing cell populations comprising a high proportion of the specific cells (at least 30%, 40%, 50%, 60%, 70%, 80%, 90% or more), even yielding a substantially homogeneous cell population as it can be evaluated by any appropriate standard method, e.g., by flow cytometry or any other immunostaining approach. The stromal elements in a given H2Sstem Progeny, in particular within hepato-active cells and three-dimensional cell clusters (see FIG. 4A and FIG. 5), are considered as part of such progeny and have not to be considered as elements contaminating such cell clusters but rather as constitutive elements.

H2Stem Cells and H2Stem Progeny can be used for establishing cell cultures for any immediate use or stored as cryopreserved preparations each containing at least $10^3$, $10^6$, $10^9$ cells or more, aimed to produce or use higher amount of H2Stem Cells or H2Stem Progeny after appropriately thawing the preparations and, if needed, for producing H2Stem Cells and H2Stem Progeny a the industrial scale (e.g. using bioreactors, membranes, microspheres, microfluidics, or any other technical solution for improving bioprocessing and cell expansion while maintaining desired cell properties). Samples of cell populations corresponding to any of the H2Stem Cells and H2Stem Progeny may be cryostored in a serum-containing or serum-free preservation medium (e.g. commercially available cryopreservation formulations) and/or in the presence of a cryoprotecting agent (e.g. dimethyl sulfoxide at an appropriate concentration).

In particular, preparations of H2Stem Cells and H2Stem Progeny comprising a predetermined number of cells (e.g. 50000, 100000, 500000, 1 million, 10 million, 100 million, 1 billion or more cells) or of three-dimensional cell clusters each having an approximately similar number of cells (e.g. 1, 10, 100, 1000 or more spheroids as the ones shown in FIG. 6) can be provided in one or more vials that can be then included in a kit comprising such vials and any other appropriate device, disposable materials (e.g. filters, syringes), solutions (e.g. PBS, cell culture medium, diluent), chemicals (e.g. enzymatic substrates, fluorochromes, drugs), biological products (e.g. growth factors, antibodies, primers) and/or instructions for using the components of such kit that can be appropriately packaged and sent to clients for using H2Stem Cells and H2Stem Progeny in vivo (e.g. for the administration to a patient or to animal) or in vitro (e.g. for testing toxicity or efficacy of compounds as candidate drugs) consequently.

The maintenance, proliferation, and/or differentiation of H2Stem Cells and H2Stem Progeny in cell culture conditions (or following implantation in an animal model or in a patient) can be performed as required for the desired use. The literature provides several protocols for maintaining liver progenitor cells and/or generating from them hepatocyte-like or hepato-active cells. The Examples provide means for obtaining H2Stem Cells and H2Stem Progeny in cell culture conditions, and for differentiating them into cells presenting liver-specific activities in the form of adherent cells or as three-dimensional cell clusters. In this latter case, H2Stem Cells and H2Stem Progeny can be provided for the desired use as three-dimensional cell clusters similar to the liver spheroids or organoids that, according to the literature, may provide cells with significant improvements in viability and functionality when administered intra- or extrahepatically, used for testing the hepatotoxicity of compounds, maintained as cryopreserved preparations, expanded in bioreactors for upscaling manufacturing process, or used in liver assist devices (Lu Y et al., 2012; Saito R et al., 2011; Massie I et al., 2011; Soto-Gutierrez A et al., 2010; Mitaka T and Ooe H, 2010; Meng Q, 2010; Tostoes R M et al., 2012). In addition to the methods described in the Examples, the three-dimensional growth of H2Stem Cells and H2Stem Progeny may be obtained also by encapsulating the cells in synthetic or biological matrices.

The maintenance, proliferation, and/or differentiation of H2Stem Cells and H2Stem Progeny can be improved by adapting cell culture conditions using technical solutions well known in the art for stem, progenitor, or mesenchymal cells of different origin. For example, ex-vivo protocols of non-cell damaging low oxygen atmosphere and other approaches for adapting in vitro microenvironments may facilitate survival, genetic stability, proliferation, post-engraftment differentiation, secretion of paracrine factors, and overall therapeutic potential of such cells, (Muscari C et al., 2013; Cigognini D et al., 2013). Otherwise, human blood-derived components such as umbilical cord blood serum and platelet lysate are tested and developed as cell culture components that are non-xenogenic alternative to fetal bovine serum and still compliant with good manufacturing practice (GMP) guidelines to yield clinically relevant cell doses without the well-known problems associated to serum such variability in the quality, risk of contamination, and undesired immunizing effects (Bieback K, 2013; Griffiths S et al., 2013).

Before being administered or otherwise used, H2Stem Cells and H2Stem Progeny can be transiently or stably modified by exposing said cells to heterologous biological or chemical agents, or by introducing said agents into the cells. In particular H2Stem Cells and H2Stem Progeny can be modified (or engineered, following their transformation with appropriate vectors) in cell culture (e.g. after and/or before their differentiation) by treating cells with growth factors and/or introducing nucleic acids that affect overall expression profile of the cells, preferably towards specific hepatic features or features helping cell culture (e.g. by transducing cells with microRNAs or with lentiviral vectors expressing recombinant proteins, such as growth factors, or transcription factors known to affect hepatic differentiation or the differentiation towards any other cell type, or fluorescent proteins).

In particular, H2Stem Cells and H2Stem Progeny may consequently present improved and/or additional biological activities in vivo and/or in vitro, after and/or before their differentiation into cells presenting a full range of liver-specific activities. Preferably, H2Stem Cells and H2Stem Progeny are engineered before being differentiated so that any of the progeny of such cells are consistently modified to have improved biological activities, independently from differentiation.

The treatment of H2Stem Progeny with chemical agents, cell culture medium, and/or nucleic acid vectors that are known as inducing the differentiation of other known liver progenitor/stem cells into other non-hepatic cell types (e.g. osteocytes, insulin-producing beta cells, or bone marrow cells) may equally provide such non-hepatic cell types. Non-hepatic cell populations that are obtained by applying these technologies known in the literature to H2Stem Cells (or any specific type of H2Stem Progeny) are additional types of differentiated H2Stem Progeny than the one described in the Examples (obtained by using a cell culture medium for inducing hepatic differentiation) that can be used in vitro and/or in vivo (in particular for therapeutic uses) according to the biological activities that the H2Stem Progeny has lost and/or acquired as a consequence to such treatment (e.g. a differentiated H2Stem Progeny that produce and secrete insulin may be used for treating diabetes).

Conventional gene transfer methods applicable to liver progenitor cells can be used to introduce nucleic acids into H2Stem Cells and H2Stem Progeny, including microinjection, electroporation, co-precipitation with calcium phosphate, liposomes, or viral transfection. Following their transformation with appropriate vectors, H2Stem Cells and H2Stem Progeny may express recombinant proteins or contain nucleic acids that allow said cells performing improved and/or additional biological activities in vivo and/or in vitro, after and/or before their differentiation into hepatocyte-like or hepato-active cells (for instance, at scope of establishing liver progenitor cell-based models for gene therapy). When the vectors are viral vectors (e.g., a lentivirus vector), they will be characterized by determination of their titer in order to select the optimal transduction efficiency conditions and proliferation rate, and to analyze their expression profile as well as their safety.

The liver is anatomically connected with the circulatory system in such a way that it allows an efficient release of various proteins into the bloodstream. Therefore, genes encoding proteins that have systemic effects may be inserted into H2Stem Cells and H2Stem Progeny (in particular before being cultured for obtaining three-dimensional cell clusters) for further improving their efficacy, as well as for their engraftment and maintenance when administered in vivo.

For example, a variety of genes coding for hormones or antibodies may be inserted into liver cells of the present invention for the secretion of their gene products into the circulation. In particular, H2Stem Cells and H2Stem Progeny may be modified to constitutively or transiently over-express a protein normally expressed by hepatocytes (and possibly already expressed by such cells), but being defective or absent in a patient (this defect underlying a pathological state of the patient, as in inborn errors of liver metabolism) and then helping restoring production of the protein and thereby helping in the treatment of the patient. Examples of such proteins are metabolic proteins such as ornithine transcarbamylase, arginosuccinate synthetase, arigininosuccinate lyase, arginase, carbamyl phosphate synthase, N-acetyl glutamate synthase, glutamine synthetase, glycogen synthetase, glucose-6-phosphatase, alkaline phosphatase, succinate dehydrogenase, glucokinase, pyruvate kinase, acetyl CoA carboxylase, fatty acid synthetase, alanine aminotransferase, glutamate dehydrogenase, ferritin, low density lipoprotein (LDL) receptor, P450 enzymes, and/or alcohol dehydrogenase.

Alternatively, H2Stem Cells and H2Stem Progeny may be modified by introducing the DNA encoding a secreted plasma protein such as albumin, a growth factor or hormone, insulin, transferrin, complement, component C3, alpha2-macroglobulin, fibrinogen alpha/beta/gamma chain, coagulation Factors (Factor V, Factor VII, Factor VIII, Factor XIII, Factor IX), alpha1-antitrypsin, or the like.

Biological materials that are obtained when generating H2Stem Cells and H2Stem Progeny can be further used for identifying biological entities that may have specific uses, in particular distinct medical applications. These biological materials include not only sub-population (or cell lines) of H2Stem Cells or of H2Stem Progeny that present specific markers, activities, and/or morphology but also any other biological entity that is obtained as intermediate or final products, such as conditioned cell culture media and fractions of these cells and media including proteins, metabolites, cell vesicles, and/or nucleic acids that can be used as biomarkers for detecting cells of medical interest or as compounds that present activities or distribution of medical interest. Even though such approach can be pursued using the cells of interest directly, additional information can be also determined by measuring the content of the conditioned cell culture media which can provide relevant information on the secretome and in particular on the paracrine effects of H2Stem Cells and of H2Stem Progeny.

Relevant biological features of H2Stem Cells or H2Stem Progeny can be identified by using technologies such as flow cytometry, immunocytochemistry, mass spectrometry, gel electrophoresis, an immunoassay (e.g. immunoblot, Western blot, immunoprecipitation, ELISA), nucleic acid amplification, enzymatic activity, 'omics technologies (proteomics, glycomics, transcriptomics, metabolomics) and/or other biological activity. In particular, technologies such as genomics, transcriptomics, proteomics, lipidomics, glycomics, etc. may provide additional means for comparing H2Stem Cells or H2Stem Progeny using databases and other datasets that are published for stem or progenitor cells, and in particular for liver progenitor cells (Yu J, et al., 2012; Santamaria E, et al., 2012; Slany A, et al., 2010). In this manner, proteins such as SUSD2 can be identified as markers whose significantly higher presence in H2Stem Cells differentiate them from cells having similar origin such ADHLSC Cells (or, in the opposite direction, the absence of CD140b expression distinguishes H2Stem Cells from ADHLSC Cells, as shown in FIG. 10).

These approaches may provide means for defining novel biomarkers associated to adult liver progenitor cells, either in vivo or in vitro (e.g. for establishing quantity, quality and homogeneity of a cell population before, during, or after its preparation and use). In particular, the biomarkers can be defined by means of the concentration of a given cell population (H2Stem Cells and/or H2Stem Progeny) in a biological sample or in a cell culture in general or in combination with the concentration of cells that present a specific protein, lipid, enzyme, phospholipid, and/or glycan. Such biomarkers can correspond to a peptide, a protein, a phospholipid, a lipid, a nucleic acid, a glycan, or any combinations of such elements components. The biomarker can be specific for assessing the suitability of a cell population being H2Stem Cells or a H2Stem Progeny, for a given use (e.g. treating a specific liver disease, obtaining hepato-active cells types following in vitro differentiation or modification with chemical agents and/or nucleic acid vectors, assessing the metabolism of a specific compound). Otherwise, the biomarker allows assessing if a given liver tissue (or sample of fresh or cryopreserved liver cells) is appropriate for obtaining H2Stem Cells more efficiently (e.g. by screening banks of liver tissues and libraries of other liver-originated biological samples such as protein extracts and cDNA libraries) for establishing which donors and/or samples can be selected).

The term "biomarker" or "marker" refers to a molecule, a parameter, a characteristic, or an entity that is objectively measured and evaluated as characterizing H2Stem Cells and or H2Stem Progeny. The quantitative evaluation of a biomarker that is associated to H2Stem Cells and/or H2Stem Progeny in a specific sample (such a tissue or a biological fluid) can be associated to a quantitative evaluation of total cells, to the efficiency with which H2Stem Cells and/or H2Stem Progeny can be produced and isolated, or a specific medical status of a patient.

H2Stem Cells and H2Stem Progeny can be used in regenerative medicine and in biological assays requiring cells that present biological features (such as metabolic or enzymatic activities, an antigenic profile, or other phenotype) as similar as possible to those observed for primary hepatocytes for the desired period of time, once they are differentiated either in vivo or in vitro, or even before inducing a full differentiation towards cells presenting a larger number and/or stronger liver-specific activities (that is, hepato-active cells). H2Stem Cells and H2Stem Progeny can be also used for in vitro applications such as pharmacological or toxicological studies (e. g. screening and characterization of biological or chemical agents) H2Stem Cells and H2Stem Progeny allow establishing of in vitro and animal models of toxicology, pharmacology and pharmaco-genetics (as extensively described for primary hepatocytes and hepatocyte-like cells derived from progenitor or stem cell of various origin) or identification of biomarkers for identifying in vivo and/or in vitro cell population of medical interest, in particular in connection to the diagnosis, the prevention, and/or the treatment of liver diseases.

The term "in vitro" as used herein denotes outside, or external to, animal or human body. The term "in vitro" as used herein should be understood to include "ex vivo". The term "ex vivo" typically refers to tissues or cells removed from an animal or human body and maintained or propagated outside the body, e.g., in a culture vessel or a bioreactor.

If H2Stem Cells and H3Stem Cells may be preferably used for in vivo applications, the H2Stem Progeny corresponding to H2Screen Cells, H3Screen-1 Cells, and the different categories of H3Screen-2 Cells may be preferably used as differentiated hepatocyte-like or hepato-active cells for drug discovery/validation H2Stem Cells and H2Stem Progeny (or corresponding biological materials that are obtained when generating them) can be provided in compositions comprising them, and in particular as pharmaceutical compositions that can be used in therapeutic methods for in vivo administration (in humans or in animal models) or in vitro applications in the form of a composition including such cells either as fresh cells or cells suitable for long-term storage (e.g. cryopreserved cells). Preferably, a composition comprising H2Stem Cells or H2StemProgeny may comprise at least $10^3$; $10^6$, $10^9$ or more cells. Such cell-based compositions may also include other agents of biological (e.g. antibodies or growth factor) or chemical origin (e.g. drugs, cell preserving or labeling compounds) that may provide a further therapeutic, diagnostic, or any other useful effect. The literature provides several examples of optional additives, excipients, vehicles, and/or carrier that are compatible with cell-based pharmaceutical compositions that may include further specific buffers, growth factors, or adjuvants, wherein the amount of each component of the composition is defined (in terms of micrograms/milligrams, volume, or percentage), as well as the means to combine them with H2Stem Cells and H2Stem Progeny.

H2Stem Cells and H2Stem Progeny can be administered in the form of a composition which depending on chosen administration method, can be a suspension of cells, a sponge or other three-dimensional structure where cells can grow and differentiate in vitro and/or in vivo including bioartificial liver devices, natural or synthetic matrices, or other systems allowing the engraftment and functionality of cells. In particular, H2Stem Cells and H2Stem Progeny can be administered via injection (encompassing also catheter administration) or implantation, e.g. localised injection, systemic injection, intrasplenic or intraperitoneal, injection intraportal injection, injection to liver pulp, e.g., beneath the liver capsule, parenteral administration, or intrauterine injection into an embryo or foetus. Moreover, H2Stem Cells and H2Stem Progeny can be used biological components of detoxification devices such as liver perfusion or liver assist devices with rigid, plastic outer shell and hollow semi-permeable membrane fibers in which H2Stem Cells or H2Stem Progeny (like other stem cells, differentiated hepatocytes, or cell types derived from tstem cells) are seeded. Bodily fluid can be perfused through the device for detoxification according to well-known procedures and then returned to the patient.

H2Stem Cells, H2Stem Progeny or composition containing them can be used for tissue engineering and cell therapy via liver cell transplantation (LCT) in intra-hepatic or extra-hepatic locations. Using this approach, animal models of human liver diseases can be also obtained by transplanting H2Stem Cells of human origin, H2Stem Progeny of human origin, or a composition containing them in animals wherein the effects of a compound on human hepatocytes can be more effectively evaluated and distinguished from effects in the animal model.

When administering a therapeutic composition comprising H2Stem Cells or a specific H2Stem Progeny, it may generally be formulated in a unit dosage. In any case, it may be desirable to include agents and/or adapt known methods for administering cells to patients that ensure viability of H2Stem Cells or H2Stem Progeny, for example by incorporating the cells into a biopolymer or synthetic polymer. Examples of suitable biopolymers include, but are not limited to, fibronectin, fibrin, fibrinogen, thrombin, collagen, and proteoglycans laminins, adhesion molecules, proteoglycans, hyaluronans, glycosaminoglycan chains, chitosan, alginate, natural or synthetically modified peptides that are derived from such proteins, and synthetic, biodegradable and biocompatible polymers. These compositions may be produced with or without including cytokines, growth factors, and administered as a suspension or as a three-dimensional gel with the cells embedded there within.

The methods of the invention contemplate not only using any donor of liver tissues for generating H2Stem Cells or H2Stem Progeny but using a patient's own liver tissue to produce and isolate H2Stem Cells and generating H2Stem Progeny or composition containing them. Such cells would be autologous to the patient and could be readily administered to the patient. Otherwise H2Stem Cells may be produced and isolated from tissue which is not patient's own. Where administration of such cells to a patient is contemplated, it may be preferable that the liver tissue subjected to the method of the present invention to obtain H2Stem Cells is selected such as to maximize, at least within achievable limits, the tissue compatibility between the patient and the administered cells, thereby reducing the chance of rejection of the administered cells by patient's immune system (e.g., graft vs. host rejection).

An issue concerning the therapeutic use of H2Stem Cells and H2Stem Progeny is the quantity of cells necessary to achieve an optimal effect. Doses for administration may be variable, may include an initial administration followed by subsequent administrations; and can be ascertained by the skilled artisan by applying the teaching of the present disclosure. Typically, the administered dose or doses will provide for a therapeutically effective amount of the cells and it may require optimization of the amount of administered cells. Thus, the quantity of cells to be administered will vary for the subject being treated (e.g. between $10^2$ to $10^{10}$ cells per each treatment in a cycle or for the entire cycle of treatment). However, the precise determination of a therapeutically effective dose may be based on factors individual to each patient, including their size, age, size tissue damage, and amount of time since the damage occurred.

Preferably, compositions comprising H2Stem Cells or a specific H2Stem Progeny should contain a substantially homogeneous cell population as defined above and the amount of cells within each dose can be consequently adjusted. In particular, when the composition comprises H3Stem Cells or any other H2Stem Progeny that form three-dimensional cell clusters, such compositions may be prepared according not only to the total number of cells (or of cell clusters) but also on the their dimension by selecting cell clusters to be administered having a diameter within a given range (e. g. between 50 μm and 200 μm or between 50 μm and 100 μm) or below/above a given size (e.g. 100 μm, 200 μm, 500 μm, or 1000 μm) and/or comprising a given number of cells (e.g. at least 10000, 20000, 50000, 100000 or more).

The distribution, differentiation, and/or proliferation of H2Stem Cells or H2Stem Progeny after their administration or implantation can be determined (as well as their activity after/before the administration of a different therapeutic agent) can be tested in human subject or in animal models (preferably a rodent). For example, the analysis of the livers of SCID mice intrasplenically transplanted with H2Stem Cells or H2Stem Progeny may demonstrate that these cells are able to engraft by detection of a human marker, and to differentiate into active, mature hepatocytes by detection of human albumin, or any other typical human liver-specific marker (or a recombinant gene that was previously transfected in the administered H2Stem Cells or H2Stem Progeny).

Another aspect of the invention is a method for preventing and/or treating a liver disease, comprising administration of H2Stem Cells, H2Stem Progeny or a composition containing them to a subject in need thereof. H2Stem Cells and H2Stem Progeny can be used for treating liver diseases, in particular those requiring the permanent (or time-limited)

re-establishment of liver function in a subject that, according to the literature, requires liver transplantation, hepatocyte transplantation, or liver regeneration given the loss of liver mass and/or function that is observed and that can be grouped in different categories.

A method for treating a liver disease comprises administering an H2Stem Product, such as H2Stem Cells or a given H2Stem Progeny, and preferably within a composition, to a subject in need thereof. In particular, a method of treating a disease in a patient in need thereof comprises administering an effective amount of an H2Stem Product to the patient, the disease being preferably a liver disease such as an inborn error of liver metabolism, an inherited Blood Coagulation Disorder, progressive familial intrahepatic cholestasis type 1/2/3, alpha 1-Antitrypsin Deficiency, defect of liver cell transporters, Porphyria, fatty liver or other fibrotic liver disease, primary biliary cirrhosis, sclerosing cholangitis, liver degenerative disease, or acute or chronic liver failure. A first category of liver diseases is represented by inborn errors of liver metabolism that can be further distinguished into errors of amino acid metabolism (such as Maple Syrup Urine Disease, Phenylketonurias, Tyrosinemia, Propionic Acidemia, Organic Aciduria, and Urea Cycle Disorders including Argininosuccinic Aciduria, Carbamoyl-Phosphate Synthase I Deficiency, Citrullinemia, Hyperargininemia, and Ornithine Carbamoyltransferase Deficiency), of metal metabolism (such as Wilson's Disease or Hemochromatosis), and of carbohydrate metabolism (such as Glycogen Storage Disease type I/II, fructosemia, or Galactosemias), lysosomal disorders (such as Wolman disease, Niemann Pick disease), peroxisomal disorders (such as Refsum Disease), Familial Hypercholesterolemias and other lipid metabolism disorders, mitochondrial diseases (such as Pyruvate Carboxylase Deficiency), and Hyperbilirubinemia (such as Crigler-Najjar Syndrome, Gilbert Syndrome, or Dubin-Johnson syndrome). A second category is represented by inherited Blood Coagulation Disorders such as Factor V Deficiency, Factor VII Deficiency, Factor VIII Deficiency, Factor IX Deficiency, Factor XIII deficiency and other deficiencies due to the insufficient amount of other coagulation-related factors (including other coagulation factors and fibrinogen alpha/beta/gamma chains) or other proteins specifically expressed and secreted by liver into blood stream (such as albumin). A third category is represented by other liver diseases not directly associated to deficiencies of coagulation or metabolism and includes progressive familial intrahepatic cholestasis type 1/2/3, alpha 1-Antitrypsin Deficiency, Caroli Disease, defects of liver cell transporters, Porphyrias (such as Acute Intermittent Porphyria), fatty liver and other fibrotic liver diseases (NASH/NAFLD), primary biliary cirrhosis, sclerosing cholangitis, liver degenerative diseases, or acute or chronic liver failure (e.g. post-hepatectomy, fulminant, virally induced, acute-on-chronic liver failure).

The use of H2Stem Cells or H2Stem Progeny in general (or specific cell populations, such as H3Stem Cells), within compositions and in methods of treatments, can provide therapeutic effects to liver diseases such as those listed above but can be also associated to in vitro studies in substitution of primary hepatocytes or liver cell lines. In particular, H2Stem Progeny can be used in (early) pharmacological and toxicological methods for evaluating the efficacy (if the H2Stem Product expresses a potential drug target for a liver-specific or non-specific disease), the metabolism, the stability, and/or the toxicity of compounds (e.g. biological or chemical entities).

Such in vitro methods and uses should generally comprise the following steps:
(a) Providing a preparation of H2Stem Product (e.g. H2Stem Cells or H2Stem Progeny in the form of cells, cell extract, or conditioned medium obtained from H2Stem Cells or H2Stem Progeny);
(b) Exposing said H2Stem Product to one or more exogenous components selected from chemical compounds, proteins, nucleic acids, lipids, sugars, metals, salts, viruses, bacteria, or cells; and
(c) Detecting the effects of said one or more exogenous components on H2Stem Product and/or detecting the presence, localization, or alteration of said one or more exogenous components following the exposure to H2Stem Product.

H2Stem Cells and H2Stem Progeny express at high level enzymes and other liver-specific proteins that are known to metabolize most of chemicals that are already registered drugs, candidate drugs still under development and pre-clinical evaluation for liver-specific effects, or any other chemical that is suspected having liver-specific effects that can be undesired (i.e. for an hepatotoxic compound) or desired (if H2Stem Cells and H2Stem Progeny express an enzyme and other liver-specific protein that is known to be itself a target for candidate drugs for a liver-specific or unspecific disease such as cancer and the compound may be then considered as a candidate drug for such disease).

In general, H2Stem Cells or H2Stem Progeny in the form of cells, cell extract, or conditioned medium obtained from H2Stem Cells or H2Stem Progeny can be evaluated in step (c) above for evaluating metabolism, elimination and toxicology of chemicals, inorganic compounds, biologicals, bacteria, viruses, or cells by the analysis of general features such as cell morphology or viability (e.g. in cytotoxicity tests). However, alternative or additional criteria may be included such as the up- or down-regulation of liver-specific (or unspecific) proteins, or any alteration (e.g. degradation, aggregation, activation, or inhibition) of proteins within the H2Stem Product (e.g. H2Stem Cells, H2Stem Progeny, or cell extract, or conditioned medium obtained from H2Stem Cells or H2Stem Progeny).

Alternatively (or in combination with the criteria evaluated for the H2Stem Cells or H2Stem Progeny and derived biological materials), step (c) may involve the analysis on how these one or more exogenous components have been internalized and/or modified or not by H2Stem Cells or H2Stem Progeny and derived biological materials. These analytical criteria vary according to the type of exogenous components as described in the literature, for example degradation, binding with other proteins, persistence in cell culture, aggregation, infectivity (for viruses), or differentiation or viability (for cells).

The literature on in vitro assays involving cells and derived products (i.e. cell extracts, conditioned media) can provide a guidance on how H2Stem Cells or H2Stem Progeny in the form of cells, compositions, and derived biological materials (i.e. H2Stem Products) can be used in vitro as indicated in the steps (a)-(c), e.g. regarding concentration, timing, culturing and assay condition, and analytical technologies. Similar assays may be also performed by introducing H2Stem Cells or H2Stem Progeny in animals in step (a) and then administering one or more exogenous components to the animals in step (b) to determine, in step (c), if and how said one or more components modify H2Stem Cells or H2Stem Progeny (or related biological materials) and/or are modified by H2Stem Cells or H2Stem Progeny in these animals.

H2Stem Products, and H2Stem Cells and H2Stem Progeny in particular, can used for the in vivo (i.e. for therapeutic uses of such cells) and in vitro (e.g. for pharmaco-toxicological uses) methods involving chemicals or biologicals described above within a kit as described above. In particular, the kit can comprise, in addition to such cells (or derived biological materials), further elements that allow using and/or detecting them and their activities when they are exposed to a panel of compounds (resulting from at least one change in the structure, the metabolite, and/or the concentration of the compound to be tested), as well as reference compounds, solutions and/or other cells that would help comparing and evaluating the effects that are observed in assays involving the use of H2Stem Cells and H2Stem Progeny.

The characterization of chemical entities as drug candidates during preclinical evaluation requires (in addition to potency, safety, or pharmacokinetics) drug metabolism assessment for identifying the relevant metabolic pathways as well as potential drug-drug interactions (with cytochrome P450-dependent induction and inhibition). This information is essential for the pharmaceutical industry when deciding to bring a lead compound towards clinical phase development. Innovative, reliable, and predictive in vitro cell-based assays for early preclinical development is urgently needed as still a large proportion of drug candidates fails during clinical development due to inadequate toxicological evaluation, in particular for hepatotoxicity.

As of today, such cell-based models are based either on human primary hepatocytes or rodent or human hepatoma-derived cell lines (such as HepaRG or HepG2 cells). None of the available models are completely satisfactory for regular pharmacological and toxicity testing. The use of human hepatocytes is limited for both qualitative and quantitative reasons due their limited availability and technical difficulties in establishing reliable sources and long-term maintenance of their hepatic functionality in culture.

Alternatively, hepatocyte-based models that are based on cells of rodent origin do not provide an optimal representation of human liver metabolism. Then, when in culture, these cells may rapidly dedifferentiate (progressively losing their key features such as drug metabolizing enzymes) and have a short lifespan (not expanding in vitro). Human hepatoma derived cell-lines are easy to expand in vitro but they lack the complete differentiated phenotype that may be important in determining metabolism and toxicity. Reliable high-throughput sub-chronic and chronic toxicity evaluation can hence not be assessed using the available human hepatocyte-based models. Acute and sub-acute toxicity screening is on the other hand hampered by the limited availability of human hepatocytes and their incapacity to expand.

Hence, H2Stem Cells and H2Stem Progeny (in particular when forming three-dimensional cell clusters) can provide better in vitro models involving continuous and readily available cells with limited variability in the hepatocyte-like pattern of enzymes stable over time in culture and from batch to batch, in particular as alternative cells to primary hepatocytes in "ADMET" (administration, distribution, metabolism, elimination and toxicology) or cytotoxicity tests (i.e. on hepatocyte viability and/or functional efficiency).

H2Stem Cells and H2Stem Progeny (in particular when forming three-dimensional cell clusters) can be used in methods for testing agents for treating liver infections or for allowing the efficient replication of a virus that infects liver and hepatocytes in particular. H2Stem Cells and H2Stem Progeny can be differentiated and/or genetically modified before or after exposing to the virus (e.g. a hepatitis virus). Then, the infected cell population can be exposed to a predetermined amount of candidate compound for treating the infection for observing any useful effect (e.g. on viral replication), used for purifying viral particles, or used for assessing any potential in vivo effect of viral infection, as shown for other liver progenitor cells in connection to Hepatitis C infection, liver fibrosis, or carcinogenesis (Wu X et al., 2012; Wang C et al., 2012; Torres D M and Harrison S A, 2012).

The teachings of all references herein specifically referred to are incorporated by reference. The invention will now be illustrated by means of the following examples, which do not limit the scope of the invention in any way.

EXAMPLES

Example 1: Preparation and Characterization of H2Stem Cells and H2Stem Cells Progeny from Primary Liver Tissues Materials & Methods
Mediums and Other Materials for Cell Culture The following materials were used: Williams' E medium (Cat. No. 22551022, Invitrogen), DMEM with high glucose concentration (4.5 g/l) and L-Glutamine (high glucose DMEM, Cat. No. 41965047, Invitrogen), IMDM (Cat. No. 21980032, Invitrogen), IMDM without phenol red (Cat. No. 21056023, Invitrogen), Hepatocyte culture medium (HCM; Cat. No CC-3198, Lonza), Fetal Bovine Serum (FBS; Cat. No. F7524, Sigma), recombinant human Epidermal Growth Factor (EGF; Cat. No. AF-100-15, Peprotech), recombinant human Hepatocyte Growth Factor (HGF; Cat. No. 100-39, Peprotech), recombinant human Oncostatin M (OSM; Cat. No. 300-10, Peprotech), recombinant human insulin (INS; Cat. No. H10219, Lilly), Insulin-Transferrin-Selenium-G Supplement (ITS; Cat. No. 41400045, Invitrogen), human albumin (50 g/L, Cat. No. 1501466 Baxter), heparin sodium (Heparin LEO®) Dexamethasone (Dex; Cat. No. D4902, Sigma), liquid penicillin/streptomycin (P/S; Cat. No. 15070063, Invitrogen), rat tail collagen I-coated T-75 flasks (Biocoat, Cat. No. 356485, BD Biosciences), Corning® CellBIND® 75 cm$^2$ Rectangular Canted Neck Cell Culture Flask with Vent Cap (Cat. No. 3290, Corning).

Preparation of Primary Human Liver Cells

The procedure for obtaining human liver cells is based on previous publications been previously described (Najimi M et al., 2007), with minor modifications. After removal, the liver was firstly flushed with ice-cold ViaSpan Solution (Bristol-Myers Squibb Pharmaceuticals) via cannulas connecting to the portal vein system, and then transferred at cold and in sterile condition to the clean room for liver cell isolation. All microbiological contamination has been strictly controlled before, during and after the isolation process. Human liver cell isolation was performed using a two-step collagenase perfusion technique under a sterile laminar flow in clean rooms. The first perfusion consisted of 37° C. preheated EBSS solution without calcium and without magnesium (Cat. No. 14155-063, Life Tech, supplemented with 0.5 mM Ethylene glycol-bis(2-aminoethylether)-N,N,N',N'-tetraacetic acid (EGTA; Sigma), 2 mg/L gentamycine, 100 000 UI/L penicillin G. This first perfusion allows eliminating extracellular ionic calcium and weakening intercellular junctions of the parenchyma. The second step included enzymatic digestion with 0.8 mg/mL collagenase (Cat. No. 11213857001, Roche Applied Sciences) diluted in EBSS solution with calcium and with magnesium (Cat. No. 24010-043, Life Tech.) supplemented with 5 mM 4-(2-hydroxyethyl)-1-piperazineethanesulfonic acid (HEPES; Cat. No. 11344-041, Life Tech.), 0.03 mg/mL of trypsin inhibitor (Cat. No. 10109878001, Roche Applied Sciences), 2 mg/L gentamycin, 100000 UI/L penicillin G. The composition of these buffers can be adapted to the actual requirements for Good Manufacturing Processes by making use of additional or alternative GMP-grade reagents (e.g. specific enzymes or N-acetylcysteine).

Each perfusion step took approximately 10 minutes before the liver was completely digested and then mechanically disrupted. Residual collagenase activity was stopped by washing the digested parenchyma with a cold M199 solution (Lonza) containing 27.5 µg/mL trypsin inhibitor, 0.05% human albumin, 2.4 mg/L gentamycin, 100 000 UI/L penicillin G Digested liver cell suspension was filtered through 4.75 to 0.25 mm pore steel mesh then washed 3 times with M199 solution and centrifuged at low speed (e. g. 1200 rpm) for 3 minutes at 4° C. to remove cell debris and a majority of non-parenchymal cells. Cells are suspended in a cryopreservation medium that is prepared by adding to 750 ml of ViaSpan Solution, 16 mg Dexamethasone, 40 UI Insulin 0.5% HEPES, 1 g/L Glucose, 15%, human albumin 20%, 10% DMSO, and then are maintained in liquid nitrogen by using appropriate vials, bags, or other system for long-term storage and preservation of human cells. Also at this stage, the composition of these buffers can be adapted to the actual requirements for Good Manufacturing Processes by making use of additional or alternative GMP-grade reagents.

The resulting liver cell preparations are predominantly constituted by hepatocytes from parenchymal fraction, each containing $10^6$-$10^9$ cells (depending from the volume of the preparations and/or the specific human liver). The cryopreserved liver cell suspensions are used by quickly thawing them at 37° C. and washing them twice in 10× volume of human albumin 5% supplemented with 2.5 g/L Glucose, 0.084 g/L bicarbonate and 5000 IE/UI/ml Heparin LEO®. After centrifugation at 224 g for 10 minutes at 4° C., the cell pellet is suspended in the required cell culture media.

Preparation of ADHLSC Cells

The ADHLSC Cells are obtained applying a method as previously described (Najimi M et al., 2007; Khuu D N et al., 2011), with or without minor modifications. Briefly, liver cell preparations are re-suspended in Williams' E medium supplemented with 10% FBS, 25 ng/ml EGF (EGF may not be present in the cell culture medium if the preparation is performed on CellBind), 10 µg/ml INS, 1 µM DEX and 1% P/S. The cells are cultured either on rat tail collagen 1-coated flasks or Corning® CellBIND® flasks and cultured at 37° C. in a fully humidified atmosphere containing 5% $CO_2$. After 24 hours, medium is changed in order to eliminate the non-adherent cells and thereafter renewed twice a week, whereas the culture is microscopically followed every day. Culture medium is switched after 12-16 days to high glucose DMEM supplemented with 9% FBS and 0.9% P/S in order to accelerate the elimination of hepatocytes and stimulate expansion of ADHLSC Cells. A cell type with mesenchymal-like morphology emerges, and proliferates. When reaching 70-95% confluence, cells are trypsinized with recombinant trypsin (trypLE; LifeTech) and 1 mM EDTA and re-plated at a density of $1$-$10 \times 10^3$ cells/cm$^2$.

Preparation of H2Stem Cells

Cryopreserved liver cell suspensions are used for preparing cell cultures on rat tail collagen 1-coated T-75 flasks at cell densities between 5 000-20 000 cells/cm$^2$ and incubated at 37° C. in a fully humidified atmosphere 5% $CO_2$. Alternatively, hypoxic conditions that were applied in the incubator (such as 5% $O_2$) or that were generated by adding anti-oxidant agents in the cell culture medium (such as N-acetyl cysteine at a 1 mM or a lower concentration). Medium change and morphology analysis are performed twice per week using, as culture media, Williams' E medium supplemented with 9% FBS, 0.9% P/S, 1 µM Dex; 10 µg/ml INS and 12.5-25 ng/ml EGF during emergence phase. Once H2Stem Cells have appeared as adherent cell clusters that predominate in the cell culture, further expansion is done in Williams' E medium supplemented with 9% FBS, 0.9% P/S, 1 µM Dex; 10 µg/ml INS, 12.5-25 ng/ml EGF in the absence or in the presence (12.5-50 ng/ml) of HGF.

H2Stem Cells having a cuboidal meso-epithelial morphology arise as small clusters and start to expand within the following 7-12 days. The clusters formed by such cells are then trypsinized within the next 2-3 days (that is, within 10-15 days after plating of primary liver cells) and then cultivated at 5000-8000 cells/cm$^2$ in Williams' E-based medium for several passages in the same medium. Trypsinisation can be performed from Passage 1 onwards at 80-90% confluence on collagen-coated plates.

Differentiation of Cells as Adherent Hepatocyte-like cells

Cells are cultivated on BD BioCoat Cellware, Collagen Type I 6-Well coated plates (Cat. No. 356400, BD Biosciences) at a density of 5000-20000 cells/cm$^2$ in the same expansion media. Hepatic differentiation is started upon 95-100% confluence by change of media to IMDM containing 20 ng/ml HGF, 20 ng/ml OSM, 1 µM Dex. 1% ITS, with (for ADHLSC Cells) or without (for H2Stem Cells) 25 ng/ml EGF. This cell culture medium for hepatic differentiation (HepDif medium) is changed twice a week over at least the next 2 (for H2Stem Cells) or 4 (for ADHLSC Cells) weeks.

Morphological Characterization of Cells in Cell Culture Conditions

The images are taken by light microscopy (phase contrast; Olympus UC30 microscopy) using Olympus camera IX50 and Cellsens Digital Imaging Software or by using the live-imaging equipment Cell-IQ (CM technologies) where a light microscopic takes a re-focused picture of the same position at regular time intervals. Cell-IQ PC (Phase Contrast) is a fully integrated continuous live cell imaging and analysis platform incorporating phase contrast and brightfield imaging capability with an onboard Analyser Software Package (Machine Vision Technology) for automatic identification, analysis and quantification of image data.

Characterization of the Genes Expressed by Cell Populations Using RT-qPCR

Total RNA is extracted from cells using the GenElute Mammaliam Kit (Cat. No. RTN70, Sigma) following DNAse treatment with DNA-Free™ kit (Cat. No. AM1906, Ambion). First strand cDNA is synthesized using Transcriptor First Strand cDNA Synthesis Kit (Cat. No. 04379012001, Roche), according to the manufacturer's instructions, and subsequently diluted with nuclease free water (Cat. No. AM9938, Invitrogen) to cDNA at 10 ng/µl. RT-PCR amplification mixtures (20 µl) contain 0.2 µg template cDNA, 10 µl 2× Taqman Master Mix (Cat. No. 4369514, Applied Biosystem) and 1 µl 20× PrimeTime qPCR assay (IDT).

Samples are run in duplicate on an Applied Biosystems ViiA™ 7 Real-Time PCR System or any other Real-Time PCR Cycler from Applied Biosystems. The cycling conditions are as follows: 10 min polymerase activation at 95° C., 40 cycles at 95° C. for 15 sec and 60° C. for 45 sec. Gene transcript-specific pairs of primer sequences were obtained from Applied Biosystems as summarized in Table 1 below.

| Human gene | Primer Sequences (ABI reference number) | Amplicon length |
|---|---|---|
| CYP3A4 | Hs00604506_m1 | 119 |
| CYP2C9 | Hs00426397_m1 | 148 |
| CYP1A2 | Hs00167927_m1 | 67 |
| CYP2C19 | Hs00426380_m1 | 106 |
| CYP2D6 | Hs02576167_m1 | 85 |
| CYP2B6 | Hs03044633_m1 | 136 |
| OTC | Hs00166892_m1 | 95 |
| UGT1A1 | Hs00153559_m1 | 65 |
| Albumin | Hs00910225_m1 | 137 |
| Vimentin | Hs00185584_m1 | 73 |
| HNF-4 | Hs00230853_m1 | 49 |
| HNF-3b | Hs00232764_m1 | 66 |
| PPIA | Hs99999904_m1 | 98 |
| GAPDH | Hs99999905_m1 | 122 |

Relative quantification of gene expression was established by normalizing the signal intensity against the endogeneous control transcripts GAPDH (glyceraldehyde-3-phosphate dehydrogenase) or PPIA (cyclophilin A). After normalization, the data were plotted and compared among cell populations.

Characterization of the Cells by Flow Cytometry

Cells are harvested, suspended at a concentration of 500-1000/µl in PBS buffer (Cat. No. SH30028.03, Thermo Fisher) and incubated for 30 min at 4 with the following fluorochrome-labeled antibodies specific for the indicated antigens that are used at the concentration indicated by the manufacturers: CD45-PE Cy7 (Cat. No. 557748, BD Biosciences), CD90-FITC (Cat. No. 555595, BD Biosciences), CD73-PE (Cat. No. 550257, BD Biosciences), CD29-APC (Cat. No. 559883, BD Biosciences), CD44-FITC (Cat. No. 555478, BD Biosciences), CD133-PE (Cat. No. 130080901, Miltenyi Biotec), Albumin-FITC (Cat. No. CLFAG2140, Sanbio), monoclonal mouse Anti-Human Cytokeratin 19 (CK-19) (Clone RCK108; M0888, Dako), anti-mouse IgG-DyLight 488 (Cat. No. 715-485-150, Jackson Immunoresearch), CD117-APC (Cat. No. 333233, BD Biosciences), CD31-FITC (Cat. No. 555445, BD Biosciences), CD31-PE (Cat. No. 340297, BD Biosciences), CD326 (Cat. No. 347200, BD Biosciences). Corresponding control isotype antibodies are used for evaluating non-specific binding of monoclonal antibodies. Cells are then washed and suspended in PBS/BSA for reading with BD Biosciences FACSCanto II Flow Cytometer.

Characterization of the Cells by Immunofluorescence or by Immunocytochemistry

Cells are fixed with paraformaldehyde 4% (Cat. No. 43368, Alfa Aesar) at room temperature for 10-15 minutes and washed for three times with PBS. When needed, endogenous peroxidase is eliminated by means of 10 minutes-incubation with hydrogen peroxide 3% (Cat. No. 31642, Sigma). Next, cells are permeabilised for 10-15 minutes using 1% Triton X-100 (Cat. No. T8787, Sigma) in PBS buffer. Non-specific immunostaining is prevented by 1 hour incubation in PBS buffer containing 5% Normal donkey serum (Cat. No. 017-000-121, Jackson ImmunoResearch) for immunocytochemistry or by 1 hour incubation at 37° C. in PBS buffer containing 5% Bovine Serum Albumin (BSA) (Cat. No A2153, Sigma) for immunofluorescence. The incubation with the primary antibody is performed for 1 hour at room temperature (or overnight at 4° C.). The samples were then rinsed three times for 15 minutes and incubated with the secondary antibody for 30 minutes (for immunocytochemistry) or 1 hour (or immunofluorescence) at room temperature.

The following antibodies were used as primary antibody according to manufacturer's instructions for immunocytochemistry or immunofluorescence: monoclonal mouse anti-human serum Albumin (Cat. No. A6684, Sigma), monoclonal mouse anti-human vimentin (Cat. No. 10515, Progen), monoclonal mouse anti-human alpha smooth muscle actin (ASMA, Cat. No. M0851, Dako), monoclonal mouse Anti-Human Cytokeratin 19 (CK-19) (Clone RCK108; M0888, Dako), monoclonal mouse anti-human TDO2 antibody (Cat. No. SAB1406519, Sigma), monoclonal mouse anti-human CK-18 antibody (Cat. No SAB3300015, Sigma), monoclonal anti-human UGT antibody (Cat. No ab129729, Abcam), monoclonal anti-human MRP-2 (Cat. No ab3373, Abcam), anti-human hepatocyte nuclear factor 4 (HNF-4; Cat. No. sc-8987, Santa Cruz), and polyclonal mouse anti-human CYP3A4 (Cat. No. SAB1400064, Sigma).

The following labeled antibodies were used as secondary antibody for immunofluorescence according to manufacturer's instructions: Alexa Fluor®488-conjugated Donkey anti-mouse IgG (Cat. No. 715-545-151, Jackson ImmunoResearch), Cy3-conjugated Donkey anti-rabbit IgG (Cat. No. 711-165-152, Jackson ImmunoResearch). For immunocytochemistry, detection is performed using Envision™ anti-mouse (Dakocytomation, Cat. No. K4001, Dako) at room temperature for 30 minutes. Detection is performed after incubation for 5 min with peroxidase-labeled polymer and substrate chromogen (DAB, Cat No. D416, Dako), followed by a washing three times with PBS. The nuclei are counterstained using 4, 6-Diamidino-2-phenylindole (Vectashield®+DAPI, Cat. No. H-1200, ABCYS) for immunofluorescence or with Mayer's Hematoxylin (Cat. No. MHS16, Sigma) for immunochemistry. Cells are mounted for immunocytochemistry and next examined at 10, 20 and 40× magnification using an Olympus inverted microscope IX50 coupled to camera UC30. Digital images are acquired using Cellsens Software. Human primary hepatocytes (obtained as indicated above) are stained in parallel as positive control for hepatic markers and negative control for mesenchymal markers. The images are taken by fluorescence microscopy (Olympus AX70) equipped with an Olympus camera XC30 and Cellsens Software.

Characterization of the Cells by Biological Activities

For luminescent CYP3A4 activity assay, differentiated hepatocyte-like cells obtained from ADHLSC Cells or H2Stem Cells are trypsinized, transferred to 96-well-microplates (Cat. No. 734-1662, Costar) at the concentration of 100000 cells/well, and activity is measured using P450-Glo™ CYP3A4 Assay with Luciferin-IPA (Cat. No. V9002, Promega). Luminescence is measured using the Victor IV luminometer (Perkin-Elmer Life Sciences). Untreated cells are measured in parallel to subtract background noise. Results are normalized to the CYP3A4 microsomes standard that is provided by the Human CYP3A4 Enzyme System (Cat. No. V4820, Promega) and calculated as picomoles/cell.

For urea secretion assay, cells are trypsinized and incubated in IMDM without phenol red (Cat. No. 21056023, Invitrogen), in collagen coated 48 well-microplates (Cat. No. 356505, BD Biosciences). As substrate for enhancing urea secretion, 1 mM Ornithine (Cat. No. 02375, Sigma) and 5 mM $NH_4Cl$ (Cat. No. A0171, Sigma) are added to the culture medium. After 2-24 hours, urea secretion is measured using the colorimetric Quantichrome urea assay kit (Cat. No. DIUR-500, BioAssay Systems). The intensity of the colour (proportional to the urea concentration in the sample) is read at 520 nm after 5-20 min incubation and is directly proportional to the urea concentration in the sample.

Total urea (mg/dl) in the culture supernatant is calculated using urea standard curve prepared in IMDM without phenol red, as recommended by the manufacturer's instructions, before establishing the amount of secreted urea as pg/cell/ 2-24 h. To evaluate any interference in the detection of actual signal, urea secretion assessment is conducted on media including ornithine/ammonia chloride and cellular controls, incubated without ornithine/ammonia chloride. These samples serve as negative control to determine specificity and prevent false positivity.

For bilirubin conjugation assay, cells are incubated with 20-50 μM non-conjugated bilirubin (Cat. No. B4126, Sigma). Conjugation of bilirubin and total bilirubin is measured after 2-24 hours using the colorimetric Direct bilirubin Assay (Cat. No. DZ151A-K, Diazyme) and Total bilirubin assay (Cat. No. DZ150A-K, Diazyme). In this assay, (un) conjugated bilirubin is mixed with the Diazyme's ready-to-use reagent, containing the detergent and the vanadate or only vanadate (pH 3), after which total or direct bilirubin in the sample is oxidized to biliverdin, respectively. Latter oxidation results in an absorbance decrease specific to bilirubin. Total/direct bilirubin concentration in the sample can be determined by measuring the absorbance before and after the vanadate oxidation. Direct/Total bilirubin concentration (mg/dl/cell/2-24 h) in the culture supernatant is next calculated against the bilirubin calibrator standard curve prepared in IMDM without phenol red, as recommended by the manufacturer's instructions. To evaluate any interference, bilirubin conjugation assessment is conducted on media including 20-50 μM bilirubin and cellular controls, incubated without bilirubin. These samples serve as negative control to determine specificity and prevent false positivity.

Results

ADHLSC Cells and H2Stem Cells are cell populations that can be both derived from preparations of cryopreserved human primary liver cells that are produced using normal adult human livers. However, the protocol for their emergence from preparation of primary human liver cells and subsequent expansion procedure in cell culture differ, in particular when making use of collagen (or other appropriate substrate) for adhesion and growth in cell culture conditions (see Materials & Methods for more details). Within 7-12 days after plating, clusters of cells having cuboidal, meso-epithelial morphology spontaneously emerge, presenting a large and transparent cytoplasm without protrusions, developing intercellular junctions, and displaying growth contact inhibition. H2Stem Cells having cuboidal, meso-epithelial morphology proliferate in clusters or colonies and, about 2-3 days after emergency, can be trypsinized and passaged at a density of 5000-20000 cells/cm². These features distinguish H2Stem Cells from the larger, later appearing, elongated ADHLSC Cells described in Najimi M et al. 2007 (FIG. 2A).

When compared to ADHLSC Cells that are cultured on either CellBind or collagen-coated supports (e.g. plates, flasks), H2Stem Cells grow with a faster proliferation rate and can be preferentially identified from cell culture and expanded. Population doubling time (PDT) for ADHLSC Cells is about 72-96 hours, while H2Stem Cells display a PDT of 48-72 hours and are rapidly expanded at least for 4-5 passages.

H2Stem Cells are positive, in accordance with other human liver progenitor cells such as ADHLSC Cells, for a series of mesenchymal markers on cell surface (including CD90, CD73, CD29, CD44) or intracellular (such as Vimentin, ASMA), as well as for hepatic markers (including HNF-3B, Albumin and cytokeratin 18), as assessed by flow cytometry (wherein positivity to a marker is defined when at least 60% of cells present the given feature), immunocytochemistry, and/or RT-PCR analysis. Both ADHLSC Cells and H2Stem Cells express at very low level (i.e. less than 15% of tested cells, and mostly below than 10%, presents a specific staining) cell surface markers for other cell lineages (hematopoietic, epithelial, and/or endothelial) such as CD45, CD117, CD31, CD133, and CD326.

However, H2Stem Cells can also be distinguished from ADHLSC Cells by comparing the presence of intracellular markers. For example, a cytoskeletal component such as cytokeratin 19 (CK-19; a cholangiocyte epithelial marker) is almost undetectable in ADHLSC Cells and hepatocytes (Najimi M et al., 2007). In H2Stem Cells (even at initial step when emerging in cell culture), CK-19 is found expressed in a percentage of H2Stem Cells comprised between 20% and 40% when evaluated by flow cytometry, a difference that cannot be defined as a negativity and that is consistently reproduced across preparations of H2Stem Cells. In fact, when CK-19 expression is evaluate by immunocytochemistry (a generally more sensitive technique for detecting intracellular proteins than flow cytometry), it is evident that CK-19 is expressed by a large majority of H2Stem even at early stages (FIG. 2B), thus providing a further marker that can be used for distinguishing and following-up populations of H2Stem Cells and H2Stem Progeny throughout the process for producing them in cell culture.

The detection of CK-19 can be associated to the detection of other intracellular proteins such as transcription factors, and in particular of those ones associated to hepatic functions, directly (by RT-PCR or antibody-based methods) or indirectly (on the basis of the coordinated expression of liver-specific genes). In this manner, H2Stem Cells have been characterized as more strongly expressing transcription factors like HNF-3b and HNF-4, when compared to ADHLSC Cells. At the intracellular level, these transcription factors are among the most important ones for obtaining the morphologic, phenotypic and functional maturation of hepatocytes, for instance by activating the expression of both hepatic serum proteins (such as albumin and alpha-1-antitrypsin) and of enzymes for (non-)metabolic functions (Snykers S et al., 2009), that can be detected in cell extracts or directly in cell culture supernatants for evaluating the presence of H2Stem Cells.

The emergence of H2Stem Cells during the initial step for the process for obtaining H2Stem Cells can be also followed, identifying which primary human liver cells can originate clusters of adherent, proliferating H2Stem Cells having a distinctive morphology and that cab be analysed by immunofluorescence or immunohistochemistry (FIG. 3).

Further features distinguishing ADHLSC Cells and H2Stem Cells can be established during or following the in vitro differentiation of these cell populations, in particular towards adherent, hepatocyte-like cells. When comparing the differentiation process of H2Stem Cells with the one of ADHLSC cells, the latter cells require more time (one month versus 1 to 2 weeks for H2Stem Cells), as well as EGF within the cell culture medium. Moreover, the morphology of the hepatocyte-like cells that are generated using the two cell types differ, wherein the cells obtained from H2Stem Cells (the H2Stem Progeny also named as H2Screen Cells; see FIG. 1) present features more similar to those of metabolically active primary hepatocytes. H2Screen Cells adopt a cuboidal hepatocyte-like morphology with mono- and binucleated cells having intracellular granularity, pointing to increased enzymatic activities (FIG. 4A).

The liver-specific metabolic activities of H2Stem Cells can be compared with those of other adult liver progenitor cells (such as ADHLSC Cells) by measuring the degradation of compounds that are accumulated in the liver and that, if inefficiently metabolized by hepatocytes, may be hepatoxic and associated to liver diseases. This analysis is of interest not only for evaluating the use of cells for clinical applications but also for drug discovery and development in the pharmaceutical industry, since drug-induced hepatotoxicity is one of the most important reasons for attrition of candidate drugs during the later stages of drug development. The effect of the exposure to different CYP450 inducers on gene expression responses and CYP450-specific enzymatic activities are often measured in different models based on cells of hepatic origin for distinguishing between potentially hepatotoxic and non-hepatotoxic compounds before administering such compounds in vivo but, none of the models under study satisfy all the criteria for early, reliable and precise detection of hepatotoxic compounds (Gerets H H et al., 2012).

In particular, hepatic CYP3A4 contributes to the metabolism of nearly 50% of currently used drugs as well as endogenous and exogenous corticosteroids. The CYP3A4 enzyme is strongly expressed in hepatocytes within adult liver and acquisition of CYP3A4 functionality is considered as important criteria of hepatogenic differentiation and maturation. Immunocytochemistry and RT-PCR already show that CYP3A4 expression is much higher in H2Stem Cells than in ADHLSC Cells (that is, already before any liver-specific differentiation), a finding that was also confirmed at activity level. H2Stem Cells show such specific activity in the range of $10^{-8}$ pMol/cell/4 h, (already well above the limit of detection at $10^{-9}$ pMol/cell) but increasing in the range of $10^{-7}$ pMol/cell/4 h after in vitro differentiation into H2Screen Cells, wherein ADHLSC Cells present an activity above $10^{-8}$ pMol/cell/4 h only after differentiation (FIG. 4B).

This comparison of liver-specific metabolic activities between H2Stem Cells and ADHLSC Cells, with or without further in vitro, liver-specific differentiation, may be performed using other indicators of metabolic activity that can be assessed using commercial kits or by applying techniques that are described in the literature (as for CYP1A2-, CYP2C19-, CYP2C9-, CYP2E1-, or CYP2D6-specific mRNA expression and/or enzymatic activity). In particular, a strong up-regulation in CYP1A2, CYP2C9, and CYP2E1 expression was observed for H2Stem Cells. These findings were confirmed when H2Screen Cells are compared to differentiated ADHLSC Cells, and also extended to the expression of genes for other liver-specific enzymatic activities (such as Ornithine Transcarbamylase, CYP2D6 or CYP2C19).

In the case of urea secretion (another major liver-specific metabolic activity), H2Screen Cells appear capable to synthesize urea in the presence of substrates (ammonia chloride and ornithine) with substantially higher metabolic properties when compared to differentiated ADHLSC Cells. H2Screen Cells present an improvement of this activity corresponding to more than 1 log and demonstrating the presence of very specific and integrated hepatic functionality within these cells (FIG. 4C).

Immunohistochemistry also confirms that, when compared to H2Stem Cells, a strong intracellular expression of CK-19, CK-18, and of some hepatic markers (such as Albumin, TDO2, and UDP-glucuronosyl transferase) is maintained, if not further increased, in H2Screen Cells, which also present the expression of a major efflux transporter protein such as MRP-2 protein at cell-to-cell interface, a feature of main importance for evaluating drug-induced toxicity related to transporter polymorphism (FIG. 4D).

Qualitatively similar evidences were obtained when comparing the capability of differentiated ADHLSC Cells and H2Screen Cells to conjugate bilirubin, another liver-specific biological activity due to the expression of UGT1A1 gene. H2Screen Cells display a much higher activity, possibly due to higher expression and/or increased nuclear localization of transcription factors such as HNF-3b and HNF-4. The UGT1A1-related bilirubin activity in differentiated ADHLSC Cells is measured at 0.05 mg/dl-0.3 mg/dl (0.5 mg/dl by exception), corresponding to 5-35% (50% by exception) conjugation after 24 hours exposure. The UGT1A1-related bilirubin activity in H2Screen Cells is measured at 0.2 mg/dl-0.6 mg/dl after 24 hours exposure or as 23-70% conjugation. Moreover, when UGT1A1 expression is compared to human hepatocytes by RT-PCR, it reaches 10% of the level observed in primary hepatocytes, a particularly high level when compared with cells that are obtained by differentiating in vitro other types of liver progenitor-derived cells.

Thus, H2Stem Cells appear as novel adult liver progenitor cells that, when compared to other cells of the same type (in particular those produced by a longer, more complex method such as ADHLSC Cells), present some major, unexpected advantages for different features (e.g. proliferation, expression of cell type-specific markers, or liver-specific enzymatic activities) that make them of interest for both clinical applications and pharmaco-toxicological studies.

Example 2: Generating Distinct Types of H2Stem Progeny as Three-Dimensional Cell Clusters Materials & Methods
Generating H3Stem Cells from H2Stem Cells H3Stem Cells are generated in Ultra-Low Attachment cell culture flasks by suspending about $1\text{-}10 \times 10^6$ H2Stem Cells in 15 ml medium before plating them on Ultra-Low Attachment cell culture flasks (75 cm$^2$; cat. No. 3814; Corning). H3Stem Cells are generated in the Ultra-Low Attachment 96-well microplates by suspending 5 000-20 000 H2Stem Cells in 0.1-0.2 ml medium and plated per well on Ultra-Low Attachment, U-shaped/round 96-well culture microplates (Cat. No. 7007; Corning). Alternatively, 75 000-100 000 H2Stem Cells are suspended in 2.0-3.0 ml medium and plated per well on Ultra-Low Attachment 6-well culture plates (cat. No. 3471; Corning).

Culture medium is by preference in Williams E medium supplemented with 9% FBS, 0.9% P/S, 1 µM Dex; 10 µg/ml INS and 12-25 ng/ml EGF in absence or presence (12.5-50 ng/ml) of HGF. Alternative commercial cell culture media that can be used instead of Williams E medium are IMDM or DMEM that are supplemented as indicated above for Williams E medium. Fresh cell culture medium is added or substituted twice a week for flask and multiwell plate/microplate formats, respectively. The formation of three-dimensional H2Stem Progeny is followed by phase contrast microscopy. Individual cells start forming these clusters after 24 hours and are harvested for measuring CYP3A4 activity, for performing immunohistochemistry, or for generating H3Screen-2 Cells within the following 10-25 days, when they reach a dimension superior to 200 µm (clusters of H3Stem Cells having a diameter up to 600 µm can be obtained).

Generating H3Screen-1 Cells from H2Screen Cells

H2Screen Cells that are obtained as described in Example 1, are trypsinised for obtaining three-dimensional H2Stem Progeny by maintaining this cell suspension in the same medium that was used for differentiating H2Stem Cells into H2Screen Cells and in an a appropriate cell culture system. When a "Hanging Drop" culture system, such as 96 well-plate Gravity$^{Plus}$Plate (Insphero), was used, half of the medium is changed 2-3 times per week by aspiration of 20 µl and addition of 20 µl fresh medium in each well of the plate. Alternatively, 1-10×10$^6$ H2Screen Cells were plated on Ultra-Low Attachment cell culture flasks, adding 5 ml of fresh cell culture medium with same frequency. Otherwise Ultra-Low Attachment, U-shaped/round 96-well culture microplates were used as described above for generating H3Stem Cells.

The formation of H3Screen-1 Cells in these cell culture systems is followed, obtained, and evaluated similarly to H3Stem Cells.

Generating H3Screen-2 Cells from H3Stem Cells

H3Stem Cells, obtained upon expansion as described above, are centrifuged for 5 minutes at 224 g in order to remove the expansion medium. Differentiation is then started in the same Ultra-Low attachment cell culture flasks using HepDif cell culture medium (see Example 1), adding 5 ml of fresh cell culture medium twice a week. Otherwise Ultra-Low Attachment, U-shaped/round 96-well culture microplates were used as described above using the same cell culture medium for differentiation. Hepatic differentiation and CYP3A4 activity are evaluated in the three-dimensional cell clusters within the following 10-20 days.

Generating H3Screen-2a Cells and H3Screen-2b Cells from H3Screen-2 Cells

H3Screen-2a Cells correspond to H3Screen-2 Cells that are maintained in suspension using Ultra-Low Attachment cell culture flasks, U-shaped/round 96-well culture microplates, or a "Hanging Drop" culture system and in HepDif medium (see Example 1)

H3Screen-2b Cells correspond to H3Screen-2 Cells that are transferred in different multi-well formats of BD Bio-Coat Cellware, Collagen Type I coated plates (with 6, 24, or 48 wells). In this condition, polygonal and granular hepatocytes are observed within 3-4 days from plating onwards in HepDif medium (see Example 1).

Generating H3Screen-2 Cells from H2Stem Cells

H3Screen Cells can directly be generated from H2Stem Cells without intermediate expansion step as H3Stem Cells. In this case, 5000-20 000 H2Stem Cells are suspended in 0.1-0.2 ml HepDif medium (see Example 1) and plated on Ultra-Low Attachment 96-well culture plates. Alternatively, 75 000-100 000 H2Stem Cells are suspended in 2.0-3.0 ml medium and plated per well on Ultra-Low Attachment 6-well culture plates. Further steps of cell culture are performed as for generating H3Stem Cells from H2Stem Cells, maintaining the cells in the HepDif medium and observing clusters of H3Screen-2 Cells of similar dimension and in a comparable period of time as shown for clusters of H3Stem Cells.

Generating H3Screen-2c Cells from H3Stem Cells

H3Screen-2c Cells correspond to H3Stem Cells that are transferred in different multi-well formats of BD BioCoat Cellware, Collagen Type I coated plates (with 6, 24, or 48 wells) and cultured in HepDif medium (see Example 1).

Immunocytochemistry (IHC), Immunofluorescence (IF), and Morphological Characterization of Three-Dimensional H2Stem Progeny Size of three-dimensional cell clusters and images are taken by light microscopy (phase contrast; Olympus UC30 microscopy) using Olympus camera IX50 and Cellsens program.

The different types of three-dimensional H2Stem Progeny are harvested and then fixed overnight in 4% paraformaldehyde (Cat. No. 43368, Alfa Aesar) at 4° C., subsequently embedded in agarose 2% (Cat. No. 16500, Invitrogen) at 65° C. and then in paraffin. Five µm-wide sections are deparaffinised and rehydrated in graded alcohol series.

Before performing immunohistochemistry is performed, the sections are incubated in citric acid monohydrate solution (pH 6.0) at 97° C. for 90 minutes. Endogenous peroxidase activity is blocked by incubating slides in a 3% hydrogen peroxide methanol solution for 15 minutes. Non-specific immunostaining is prevented by incubating sections at room temperature in PBS buffer containing 1% bovine serum albumin (BSA, Cat. No. A2153-50G, Sigma) for 1 hour.

The sections are then incubated overnight at 4° C. with one of the following primary antibodies diluted in 0.1% BSA and according to manufacturer's instructions: monoclonal mouse anti-human serum Albumin (Cat. No. A6684, Sigma; for IHC), monoclonal mouse anti-human CYP3A4 (Cat. No. SAB1400064, Sigma; for IHC), polyclonal rabbit anti-human Ornithine carbamoyltransferase (Cat. No. HPA000570, Sigma; for IHC), polyclonal rabbit anti-human UDP-glucuronosyltransferase 1A1 (Cat. No. sc-27415, Santa Cruz; for IHC), MRP-2 (Cat. No. ab3373, Abcam; for IHC), monoclonal mouse anti-Human Cytokeratin 19 (CK-19) (Clone RCK108; M0888, Dako; for IHC), monoclonal anti-CK19 (Cat. No. SAB3300018, SIGMA, for IF), monoclonal anti-CK-18 (Cat. No. SAB3300015, SIGMA; for IF), monoclonal mouse anti-human vimentin (Cat. No. 10515, Progen; for IHC), monoclonal anti-vimentin (Cat. No. V6630, SIGMA; for IF), anti-human hepatocyte nuclear factor 4 (HNF-4) (Cat. No. sc-8987, Santa Cruz; for IHC), monoclonal anti-HNF4 (Cat. No. SAB4501409, SIGMA; for IF), monoclonal anti-HNF3B (Cat. No. SAB2500409, SIGMA; for IF). The following labeled antibodies were used as secondary antibody for immunofluorescence (IF) according to manufacturer's instructions: Alexa Fluor®488-conjugated Donkey anti-mouse IgG (Cat. No. 715-545-151, Jackson ImmunoResearch), Cy3-conjugated Donkey anti-rabbit IgG (Cat. No. 711-165-152, Jackson ImmunoResearch). For immunohistochemistry, Horseradish Peroxidase (HRP)-based staining is used for detecting primary antibodies using Envision anti-mouse (Cat. No. K4001, Dakocytomation), anti-rabbit (Cat. No. K4003, Dakocytomation) or anti-goat IgG-HRP (Cat. No. sc-2020, Santa Cruz) and SIGMA-FAST™ 3,3'-Diaminobenzidine tablets (Cat. No. D4168, Sigma) as chromogenic substrate. The nuclei are counterstained using 4, 6-Diamidino-2-phenylindole (Vectashield®+DAPI, Cat. No. H-1200, ABCYS) for immunofluorescence or with Mayer's hematoxylin (Cat. No. MHS16, Sigma) for immunohistochemistry. Analysis is done using an Olympus inverted microscope IX50 coupled to camera UC30. Digital images are acquired using Cellsens Software.

Characterization of Three-Dimensional H2Stem Progeny by Western Blot Analysis

Cells (at a concentration of 5×10$^6$ cells par ml) are lysed in a buffer containing 10 mM HEPES pH 7.4, 80 mM KCl, 2 mM EDTA, 15 mM beta-mercaptoethanol, 0.1% Triton X-100 et 1% PIC (proteases Inhibitor Cocktail). Protein extracts are incubated under agitation at 4° C. for 30 minutes, and then homogenized using Potter Dounce (10

A.R.) into ice. Cell lysates are then centrifuged at 4000 g for 10 minutes to pellet cell debris. The protein concentration in the resulting supernatant is next determined following the classical Bradford method, using a commercial kit (Bio-Rad). Protein extracts are separated by electrophoresis using SDS-PAGE and then electrotransferred on a nitrocellulose membrane (Amersham, UK). The membrane is then incubated at room temperature for 2 hours in TBS-t buffer (Tris Buffered Salin-tween: Tris/HCl 50 mM, NaCl 150 mM, Tween® 20 0.1%) containing skimmed milk (5% (W/v); Merck). The membrane is then incubated at 4° C. under agitation overnight in the same TBS-t/milk 5% but containing the primary antibody according to manufacturer's instructions. After being washed three times for 15 minutes with TBS-t buffer, the membrane is incubated at room temperature for 2 hours with the peroxidase-labeled secondary antibody in the TBS-t/5% milk buffer. After being washed three times for 15 minutes with TBS-t buffer, protein signal is revealed by chemioluminescence (kit ECL, Amersham Pharmacia Biotech.).

The following antibodies are used as primary antibody according to manufacturer's instructions: polyclonal rabbit anti-human CYP3A4 (Cat No, AB1254, Chemicon), polyclonal anti-rabbit anti-UGT1A1 (Cat. No. 4371, Cell Signaling Technology) and anti-SULT1 (Cat. No. sc-32928, Santa Cruz)

Characterization of the Genes Expressed by Three-Dimensional H2Stem Progeny Using RT-qPCR The three-dimensional H2Stem Progeny from a well of a 6-well plate (or from 1 to 10 wells from a 96-well microplate) are collected in a 1.5 ml tube and rinsed with 1 ml PBS, waiting for cell clusters to fall at the bottom of the tube by gravity, before removing the PBS. Cell clusters are lysed using 350 µl of RLT buffer Plus, vortexing the tube for 30 seconds and disrupting the spheroids by mechanical action using a motorized system to rotate pistons (Cat. W14044, Fisher Scientific) with RNase free pistons (Cat. W5290W, Fisher Scientific).

Total RNA is extracted from cells using RNeasy® Plus Mini Kit (Cat. No. 74134 QIAGEN), following DNAse treatment with DNA-Free™ kit (Cat. No. AM1906, Ambion), First strand cDNA is synthesized using Transcriptor First Strand cDNA Synthesis Kit (Cat. No. 04379012001, Roche), according to the manufacturer's instructions, and subsequently diluted with nuclease free water (Cat. No. AM9938, Invitrogen) to cDNA at 10 ng/µl. RT-PCR amplification mixtures (20 µl) contain 0.2 µg template cDNA, 10 µl 2× Taqman Master Mix (Cat. No. 4369514, Applied Biosystem) and 1 µl 20× PrimeTime qPCR assay (IDT). Samples are run in duplicate on an Applied Biosystems ViiA™ 7 Real-Time PCR System or any other Real-Time PCR Cycler from Applied Biosystems. The cycling conditions are as follows: 10 min polymerase activation at 95° C., 40 cycles at 95° C. for 15 sec and 60° C. for 45 sec. Gene transcript-specific pairs of primer sequences were obtained from Applied Biosystems as described in Example 1.

Characterization of the Three-Dimensional H2Stem Progeny by Biological Activities The CYP3A4 activity of the three-dimensional H2Stem Progeny can be measured using luminescence assay with a procedure similar to the one performed for adherent cells (see Example 1). Up to five three-dimensional cell clusters, each containing approx. 20 000 cells, are washed with PBS buffer to remove residual medium and then transferred to BD BioCoat™ Collagen 48-well-plates (Cat. No. 356505, BD Biosciences). After a 4-hour incubation with 200 µl IMDM (Cat. No. 21980032, Invitrogen) containing 0.2 µL luciferin-IPA (Cat. No. V9002, Promega). The cell suspension (100 µl of medium) is transferred into 96-well-plates (Cat. No. 734-1662, Costar) and analysed as described in Example 1. The cell culture medium that is not incubated with the three-dimensional cell clusters is used as control of the background noise.

Urea secretion and bilirubin conjugation assays for testing liver-specific metabolic activity were performed using three-dimensional cell clusters, each containing approx. 100 000 cells (equivalent to 5 spheres of H3Stem Cells or H3Screen-2a Cells), that are incubated with adequate reagents as described above in Example 1.

SULT activity was tested in combination with UGT1A (i.e. including UGT1A1 and other UGT1A isoforms) using paracetamol as a substrate for the reaction. The glucuronidation and sulfate conjugation products of paracetamol are quantified by HPLC as described (Lau G and Crichley J, 1994). Briefly, the cells are incubated for 24 hours with 5 mM paracetamol (Cat. No. A7302, Sigma). After incubation, media supernatants is centrifuged, filtrated and analysed by means of UV-HLPC at 254 nm. 2-acetaminophenol is added as internal standard. The specific standards for quantification are paracetamol-sulfate (Cat. No UC448, Sigma) and P-Acetamidophenyl-β-D-Glucuronide (Cat. No A4438, Sigma). Nova-Pak C18 Radial-Pak Column, 60 Å, 4 µm, 8.0 mm×100 mm (Waters) is applied as stationary phase. The mobile phase consists of 0.1M $KH_2PO_4$, 0.1% acetic acid & 0.75% propan-2-ol at pH 3.8 (debit of 1.5 ml/min). The results are expressed as the production of pmol glucu-ou sulfo-metabolites per minute and per mg protein. Protein concentration is assessed according to the classical Bradford method, using the Bio-Rad kit.

CYP-dependent enzymatic activities were determined by LC/MS/MS after incubating the cells with a substrate cocktail (10 mM Phenacetin, 100 mM Bupropion, 10 mM Diclofenac and 3 mM Midazolam). To evaluate the transporter functionality, the cells were incubated at 37° C. (or at 4° C. for some experiments) in 500 µL of HBSS containing [$^{14}$C] transporter marker substrate at 10 µM (0.5 µCi/mL). Following substrates were used: Taurocholate (TC), Estrone-3-sulphate (E3S) and 1-methyl-4-phenylpyridinium (MPP). At the end of incubation, supernatants were removed and monolayers were washed 3 times with ice cold PBS. Then, 300 µL NaOH 0.1 N was added into each well to lyse cells. An aliquot (100 µL) was taken and mixed with 2 mL Ultima Gold scintillant for evaluating concentration of marker substrate inside the cells with a Tri Carb Counter. Inducibility of phase I CYP-dependent activity was evidenced after co-treatment with rifampicin (10 µM) (CYP3A4, CYP2C9, CYP2B6) and Beta-naftoflavone (25 µM) (CYP1A2) for three days.

Enzymatic activity of carboxylesterase-1 (CES-1) was measured using an ELISA Kit (Cat. No. ab109717, Abcam) using the protein taken from cell cultures from H2Stem, H3Stem, ADHLSC, using primary human hepatocytes and HepG2 as positive controls. The protocol was used according to manufacturer's instructions. Secreted alpha-antitrypsin was quantified in conditioned culture media from H2Stem and ADHLSC using an ELISA kit (Cat. No. ab108799, Abcam), according to the manufacturer's instructions.

Results

As a further feature distinguishing H2Stem Cells and H2Screen Cells from undifferentiated and differentiated ADHLSC Cells (or other human liver progenitor cells), these new cell populations that are described in Example 1 provide suspensions of distinct types of three-dimensional cell clusters (i.e. three-dimensional H2Stem Progeny) that comprise liver progenitor cells or hepatocyte-like cells, depending on the cell culture conditions.

When H2Stem Cells or H2Screen Cells are maintained in either hanging drop culture systems or low adherence plates, three-dimensional cell clusters having a diameter of 50-100 µm are quickly formed within the first 2-4 days, reaching a size of more than 300 µm and even up to 600 µm after 15-25 days (FIGS. 5 and 6). These cell clusters, presenting some supportive stroma between the cells, can be maintained in cell culture at least to 1-2 months. In contrast, ADHLSC Cells (either undifferentiated or differentiated, cultured in the same conditions) provide at most 20 µm-sized, essentially two-dimensional aggregates that do not present the strong liver-specific metabolic activities that are observed for H2Stem Progeny that form three-dimensional cell clusters. Three-dimensional H2Stem Progeny that comprise either undifferentiated (H3Stem Cells) or differentiated (H3Screen Cells) cells can be generated in hanging drop culture systems, Ultra-Low Attachment cell culture flasks, plates, or microplates with U-shaped/round wells. These containers were developed for culturing embryoid bodies or other cells as spheroids in suspension. Surface exposed to cell culture is covered by a covalently bound hydrogel layer that is hydrophilic, neutrally charged, and inhibits cell immobilization (Saleh F. et al. 2012).

Depending on the further use, the content of a single well, plate, or flask (or the result of pooling the content of wells in a microplate in order to obtain 5, 10 or more spheres of three-dimensional H2Stem Progeny), or each sphere-like cluster can be used or tested separately, in the same well or otherwise, allowing an high throughput assessment of effects of compounds or cell culture condition in parallel to other criteria (such as enzymatic activity or gene/protein expression) on a given three-dimensional H2Stem Progeny.

H3Stem Cells are a three-dimensional H2Stem Progeny that is mainly constituted by liver progenitor cells and can be obtained by culturing H2Stem Cells. Three-dimensional H2Stem Progeny contains hepato-active cells following the incubation into an appropriate medium (as in the case of H3Screen-1 Cells and H3Screen-2 Cells). In particular, H3Screen Cells can be maintained as three-dimensional H2Stem Progeny that are either adherent (in the case of H3Screen-2b Cells and H3Screen-2c Cells) or in suspension (in the case of H3Screen-2a Cells and H3Screen-1 Cells), depending on the cell culture conditions, that is, if conditions for generating these different types of three-dimensional H2Stem Progeny are applied in a specific sequence or simultaneously. At morphologic and phenotypic level, three-dimensional H2Stem Progeny resembles a micro-liver scaffold consisting of a supportive stromal scaffold and an inner hepatic cell mass (FIG. 5). The use of U-shaped/round, 96 well microplate results in more standardized three-dimensional H2Stem Progeny, having a more uniform size and a more controlled generation of the cell clusters in each well. In fact, H2Stem Progeny that is transferred in such systems for cell culture rapidly aggregates in a single, sphere-like cluster of cells that may contain more than 100000 cells (FIGS. 5D and 6).

Three-dimensional H2Stem Progeny still express markers that are identified in H2Stem Cells such as a mesenchymal marker like vimentin and a hepatic marker such as Albumin. Moreover, three-dimensional H2Stem Progeny generally present higher expression levels of major liver-specific metabolic activities, directly (like CYP3A4, CYP1A2, CYP2B6, CYP2C9, CYP2E1, Ornithine transcarbamylase, and UGT1A1), or indirectly (for transcription factors such as HNF-3b and HNF-4), when compared not only to ADHLSC Cells but also to H2Stem Cells and H2ScreenCells. These observations suggest that the three-dimensional H2Stem Progeny is able to reproduce much better not only the structural three-dimensional organization but also the functionalities that hepatocytes present in vivo. When analysed by immunohistochemistry, H3Screen-1 Cells show strong expression of albumin, CYP3A4, Ornithine transcarbamylase (OTC; an enzyme of urea cycle) and UDP-glucuronosyl transferase 1A1 (UGT1A1; the enzyme for bilirubin conjugation), together with strong CK-19 and CK-18 expression.

At the level of enzymatic activity, the CYP3A4 activity in the three-dimensional H2Stem Progeny comprising hepatocyte-like cells was measured in comparison with primary hepatocytes and H2Stem Cells and H2Screen Cells. When the absolute values are compared (FIG. 7A), the already significantly higher CYP3A4 activity of H2Stem Cells, when compared to ADHLSC Cells before or after differentiation (see Example 1 and FIG. 4B), are already reached by H3Stem Cells and are further increased in H3Screen Cells, such as H3Screen-2a Cells. These values, when defined on the basis of cell number, indicate a CYP3A4 activity in the range of $10^{-2}$-$10^{-3}$ pmol/cell cluster of H3Screen-2a Cells, corresponding to a range of $10^{-5}$-$10^{-6}$ pmol/cell (depending on the total number and density of cells), thus obtaining at least a further one log improvement when comparing to H2Screen Cells. Such a value is well above the levels of CYP3A4 activity that are measured in differentiated ADHLSC Cells, and approaching the level that are measured in primary hepatocytes.

Further validation of the liver-specific metabolic activities of the different types of H3Screen Cells can be performed, similarly to what was described in Example 1 for H2Stem Cells and H2Screen Cells, such as urea secretion (see FIG. 4). Alternatively, other indicators of metabolic activity can be assessed using commercial kits or by applying techniques that are described in the literature for determining the level of mRNA and/or protein expression for relevant markers and/or of enzymatic activity (e.g. in connection to CYP1A2-, CYP2C19-, CYP2C9-, or CYP2D6-specific metabolization of compounds).

Moreover, significantly higher enzymatic activity were measured in H3Screen Cells (and in particular, H3Screen-2a and -2b Cells) when compared to H2Stem Cells or H2Screen Cells after induction with Rifampicin and beta-naphtoflavone (a test for evaluating the measurable effects of drug-drug interactions), resulting in a fold induction of 36.22× for CYP1A2 activity, 93.71× for CYP2B6 activity, 2.13× for CYP2C9 activity and 31.23× for CYP3A4 activity. H3Stem Cells and H3Screen Cells also display substantial UGT1A and SULT protein expression and activity (FIGS. 7B and C), approaching also in this case the levels that are measured in primary hepatocytes, that is 10% up to almost 100%. This extensive glucuronidation capacity is not only of major importance for the development of toxicological screening models but also unveil a clinical application potential of these novel cells for e.g. Crigler-Najjar Syndrome. H3Screen Cells are furthermore capable to synthesize urea in the presence of substrates (ammonia chloride and ornithine), with substantially increased or accumulated urea production over time, confirming their extensive metabolic capacity.

Figure 7:
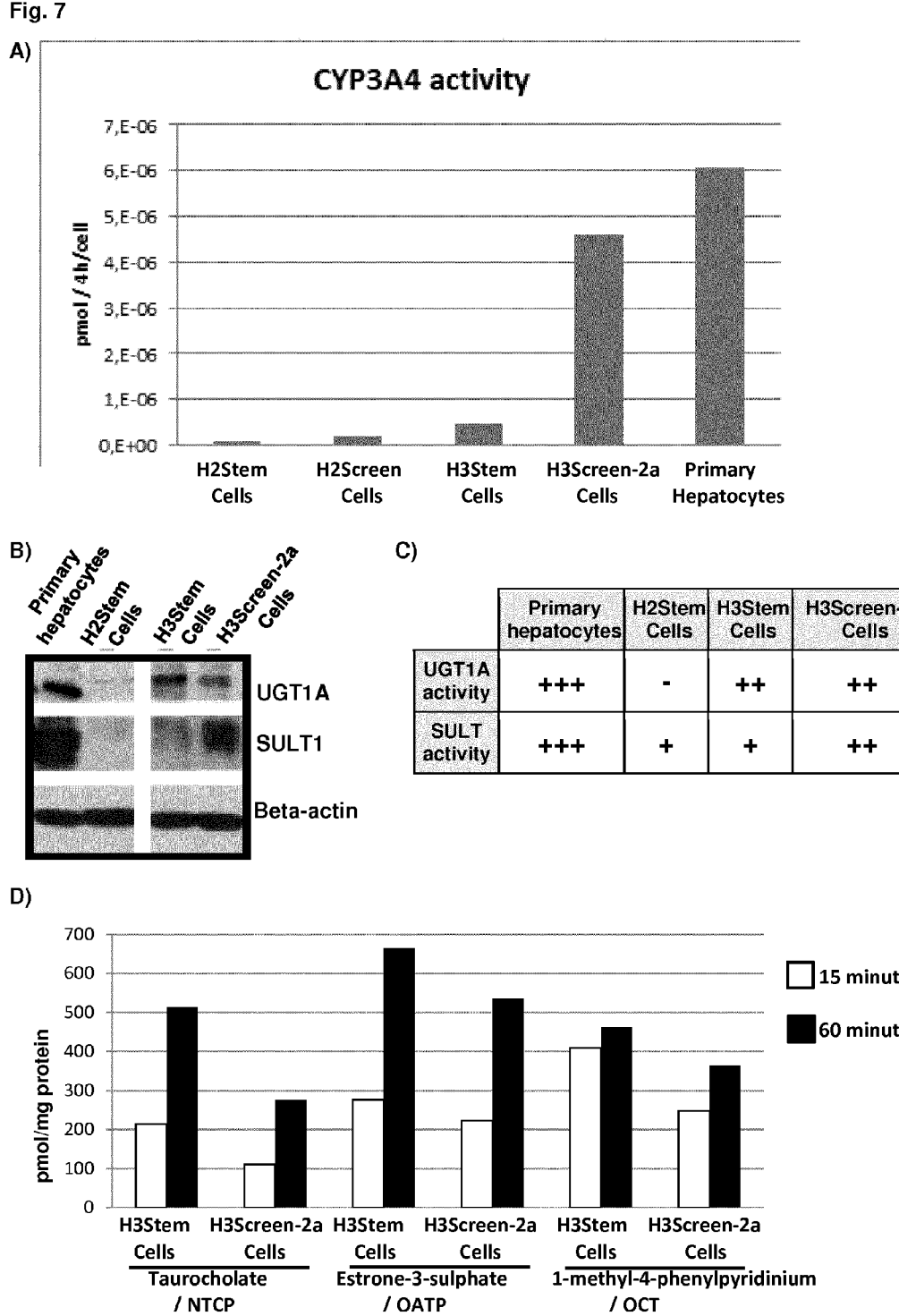
FIG. 7: Comparison of protein expression and activities of liver enzymes in different categories of H2Stem Progeny, and in a preparation of primary human hepatocytes. CYP3A4 activity over a period or 4 hours is compared (A). Western blot analysis (B) shows that, in the presence of similar amounts of protein in the extracts (as confirmed by using an anti-beta actin antibody as a control), H2Stem Cells present low amount of SULT1 and of UGT1A proteins that are more expressed in H3Stem Cells and (in particular for SULT1) in H3Screen-2a Cells. Multiple bands are visible for SULT1 since the antibody that has been used is a commercial preparation of a rabbit polyclonal antibody that recognizes an epitope common to different human SULT1A isoforms (Sulfotransferase 1A1, 1A2 and 1A3) and is partially cross-reactive with other SULT family members of human origin (see description for SULT1 antibody H-55; Santa Cruz cat. No. sc-32928). The data on protein expression are confirmed qualitatively by testing the corresponding enzymatic activities (C). The ability of H3Stem Cells and H3Screen-2a Cells to uptake three specific chemical substrates (Taurocholate, Estrone-3-sulphate, 1-methyl-4-phenylpyridinium) by their respective transporters (sodium taurocholate co-transporting polypeptide, NTCP; organic anion transporting polypeptide, OATP; organic cation transporter, OCT) has been determined in such cells at two time points, with a kinetic profile of the uptake that confirms how H3Screen-2b shows a genuinely active process, and not simple a passive diffusion process, for such compounds (D). Qualitatively comparable data were obtained on basal and induced metabolization of drugs by Phase I enzymes (Phenoacetin by CYP1A2; Bupropion by CYP2B6; Diclofenac by CYP2C9; Midazolam by CYP3A4) after 4 hours, by comparing H3Stem and H3Screen-2a with primary hepatocytes.

The functionality of uptake transporters sodium taurocholate co-transporting polypeptide (NTCP), organic anion transporting polypeptides (OATPs, such as OATP1B1 and OATP1B3) and organic cation transporters (OCTs (OCT1 and 2) was evaluated by measuring the uptake of Taurocholate, Estrone-3-sulfate, or MPP. Both H3Stem and H3Screen-2a Cells showed an increased uptake of such compounds over 15-60 minutes (FIG. 7D). Moreover, both H3Stem Cells and H2Stem Cells present liver-specific activities like CES1 (liver carboxylase) that are not only superior to ADHLSC Cells or a commonly used cell line like HepG2, but also approaching the ones detected in vitro for primary human hepatocytes (FIG. 8A). Similarly, the secretion of alpha-1-antitrypsin by H2Stem Cells is considerably superior by the one observed for ADHLSC Cells (FIG. 8B), a further feature that can be further evaluated in H3Stem Cells and H3Screen Cells. These evidences confirm the presence of active uptake and metabolization of specific compounds in H3Stem and H3Screen Cells that can be exploited for testing candidate drugs.

Thus, H2Stem Cells can be used to provide H2Stem Progeny that can be maintained as three-dimensional cell clusters (three-dimensional H2Stem Progeny) that comprise liver progenitor cells or hepato-active cells, grow efficiently in cell culture conditions, and are useful for providing metabolically active and/or proliferating cells. Metabolism- and proliferation-related features can be combined to other features (such as the presence/absence of cell type- or activity-specific surface markers, the diameter, the type of stromal structure, or other biological activities) for determining which type of three-dimensional H2Stem Progeny three-dimensional as identified above (or a further sub-type that can be functionally or morphologically determined) has the more appropriate functional, morphological, or antigenic profile for a given use.

For instance, a specific range of diameters (corresponding to an average number of cells and amount of protein/DNA), a process combining or not in vitro differentiation (see FIGS. 1 and 6), the transformation with vectors for expressing recombinant proteins, and/or a specific antigenic profile may be preferred when the three-dimensional H2Stem Progeny is intended for in vivo administration (e.g. by intraportal injection or intra/extra-hepatic implantation, with or without any preliminary treatment with trypsin, within or not a device or a biocompatible matrix).

Alternatively, larger three-dimensional H2Stem Progeny that are generated in suspension either from H2Screen Cells (H3Screen-1 Cells) or H3Stem Cells (H3Screen-2a Cells or H3Screen-2b Cells) may be more appropriate for in vitro uses that involve the exposure to liver-targeting viruses, the transformation with vectors for expressing recombinant proteins, and/or the exposure to a panel of compounds. These experiments may provide relevant information on how such a model would allow expressing efficiently viral or human proteins, or evaluating the therapeutic efficacy, the metabolism, the stability, and/or toxicity of compound on hepatic metabolism, in particular for pharmacological or toxicological pre-clinical screening and testing.

Example 3: Molecular Features Characterizing H2Stem Cells

Materials & Methods
Proteomic Analysis of ADHLSC Cells and H2Stem Cells

Proteomic analysis was performed in two-dimensional (2D) gels using Ettan™ DIGE system (2D-DIGE; GE Healthcare Life Sciences) as previously described (Vanheel A et al., 2012) with some minor adaptations. Briefly, cell pellets were prepared by harvesting cells in cultures at 95% confluence, counting and centrifuging at 300 g for 5 minutes at 4° C. The cells were washed with 10 ml (per $5 \times 10^6$ cells) of ice-cold wash buffer that is prepared using 45 ml Phosphate Buffered Saline (PBS), 5 ml EDTA solution (50 mM; Cat. No. 17-1324-01, GE Healthcare) and 1 tablet of Protease inhibitor cocktail (cOmplete; Cat. No. 11873580001, Roche Applied Sciences). Upon homogenization, the cells were washed and centrifuged twice in 1 ml ice-cold wash buffer per $5 \times 10^6$ cells. Finally, the supernatant was removed and cell pellets were snap-frozen in liquid nitrogen and stored at −80° C.

After determining protein concentration in the cell extracts, minimal labeling with N-hydroxysuccinimidyl-ester dyes Cy2, Cy3 and Cy5 (GE Healthcare Life Sciences) was performed as described by the manufacturer. CyDye-labeled 2D-DIGE gels were scanned on the Ettan DIGE Imager (GE Healthcare Life Sciences). Gel images from all three CyDyes were loaded into DeCyder 7.0 software (GE Healthcare Life Sciences) and analyzed.

Principal Component Analysis (PCA)

Statistical significance of the variation in abundance within a group to the magnitude of change between groups was calculated using Student's t test and analysis of variance (ANOVA). Spots present in 70% of the gel images, and with a statistically significant ANOVA ($p \leq 0.05$) were considered for further analysis. The Principal Component Analysis (PCA) was performed using the DeCyder extended data analysis (EDA) module (GE Healthcare). The fluorescence intensity of each spot is normalized to this internal standard, making a comparison between gels possible. This process is performed by the DeCyder software (GE Healthcare).

Protein-Based Cell Detection

Flow cytometry or Western blots analysis were performed on a selection of potential surface biomarkers that were identified by proteomics analysis. The FACSCANTO cytometer and FACSDiva software were used (BD biosciences). Cells were incubated after fixation with primary antibodies PE Mouse Anti-Human CD140b (BD Pharmingen; Cat. No. 558821) and PE anti human SUSD2 (W5C5 and W3D5 antigens, Cat. No. 327406 and 327506, BioLegend) before analysis. Viability was measured using 7AAD (Cat. No. 559925, BD Pharmingen). For Western blot analysis, a commercial anti-beta-actin antibody was used as control according to manufacturer's instructions. For flow cytometry, the percentages of positive cells were normalized with 3% positivity of appropriate control isotype.

Results

Examples 1 and 2 present experimental data about a first series of molecular or enzymatic features can allow distinguishing H2Stem Cells and H2Stem Progeny from other cell types by using commercially available products (antibodies, PCR primers, and/or kits). However a more general qualitative and quantitative characterization of H2Stem Cells and H2Stem Progeny can be performed by different technologies for broadly analyzing the transcriptome, lipidome, metabolome and/or proteome of these cells. Then, by comparing the set of results between each other or with similar data obtained from distinct cell populations (e.g. different preparations of H2Stem Cells, H2Stem Progeny, primary human hepatocytes, or ADHLSC Cells) a more precise biological profile of H2Stem Cells and H2Stem Progeny can be established by identifying biomarker(s) that may help distinguishing between different cell populations.

Figure 9:
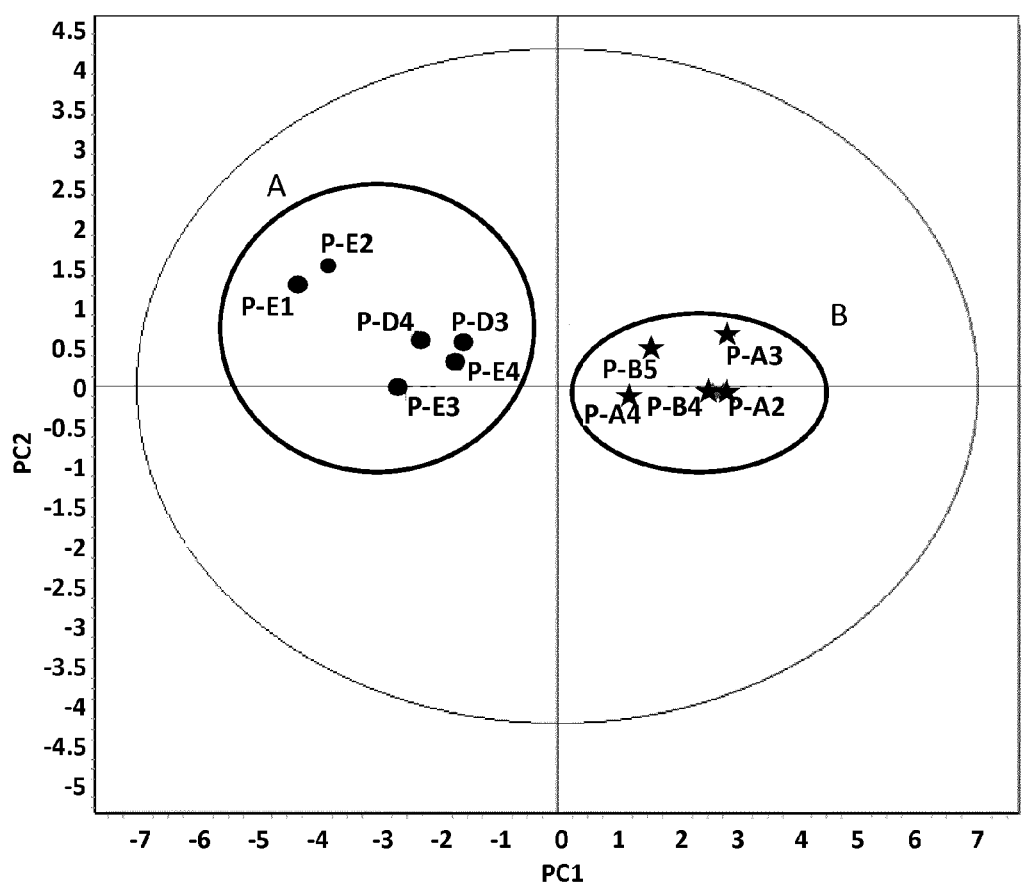
FIG. 9: The proteome of ADHLSC Cells and H2Stem Cells can be characterized by Principal Component Analysis (PCA), identifying groups of proteins that are over-/under-represented in these specific adult liver progenitor cell populations when compared to each other. The overall proteome of distinct cell preparations are graphically represented (see spots for distinct ADHLSC Cells preparations and stars for distinct H2Stem Cells preparations). This approach allows concluding that different ADHLSC Cells and H2Stem Cells preparations can still be grouped by cell type (A). This proteomics-based analysis on the combined presence (or absence) of specific proteins (or protein isoforms) as established by such an approach may be further validated by transcriptomic-based studies, RT-PCR or by antibody-based technologies (such as Flow Cytometry, Western Blot, Immunocytochemistry). This approach can be also applied for identifying markers distinguishing H2Stem Cells (or a type of H2Stem Progeny) from other cell populations in vivo and/or in vitro, as well as for evaluating liver-specific metabolic activities or H2Stem Cells-specific features among different preparations of H2Stem Cells or H2Stem Progeny.

As a first approach, the proteome of ADHLSC Cells and H2Stem Cells was compared by extracting the whole protein content from proliferating cultures of these cells and subjecting it to two-dimensional gel analysis to identify changes in expression, turnover and/or protein modification. Differential spots were picked up by means of differential expression analysis and quantified by 1-way ANOVA in order to perform a Principal Component Analysis (PCA), an unsupervised multivariate statistical method used to analyse the variability between experimental groups. A PCA was performed with all ANOVA 0.05-relevant spots, leading to two distinct clusters of spots that would suggest distinct biomarker profile (in addition to functional features) between distinct preparations of the two cell populations (FIG. 9).

More in depth analysis of these differential spots can be performed by protein sequencing using mass spectrometry for actually identifying the relevant proteins and then confirming these evidences with other technologies and commercial products (e.g. by using antibodies in Western blot or flow cytometry, primers for RT-PCR). Alternatively, array-based technologies and other approaches providing large panels of gene-specific detecting agents (being primers, labeled antibodies, or lectins) may allow comparing the amount of specific proteins (grouped by activity, localization or other criteria) in distinct samples and then restricting the number of proteins that deserve a more detailed analysis in different cell populations and/or cell culture conditions.

When data from immunological, transcriptomic and/or glycomic analysis are combined, further information on H2Stem Cells or H2Stem Progeny can suggest features of these cells that may be of potential interest for further validation (including medical uses, paracrine effects, and interactions with other cells, extracellular matrix or other biological effectors). Such an approach may involve the comparison with other cell populations (e.g. primary human hepatocytes, different preparations of H2Stem Cells or different H2Stem Progeny, maintained as adherent cells or three-dimensional cell clusters) as well as biological materials derived from such cell populations (such as conditioned medium or specific cellular or protein fractions).

Different technologies allow obtaining preliminary data on the over- or under-representation of specific proteins in such biological materials from H2Stem Cells and distinct types of H2Stem Progeny and compared not only to ADHLSC Cells but also to adult liver progenitor cell populations or even primary human hepatocytes. These evidences on the over- or under-representation of specific proteins in distinct cell populations can be used for different in vivo and/or in vitro applications that require establishing the quality and/or quantity of adult liver progenitor cell populations in general, and of H2Stem Cells (or of one or more types of H2Stem Progeny) in particular, by using appropriately validated biomarkers in the initial step of their process of production and in later passages (as defined in the Detailed Description above).

Preferred approaches for determining such biomarkers are those that can be validated without the limitation due to low throughput or large amount of cells to be tested and destroyed. Thus, further studies may be focused on biomarkers that can be assessed into the supernatant of cell culture medium and/or by flow cytometry. At this scope, the abundance of proteins can be initially assessed into H2Stem Cells and ADLHSC Cells using the two-dimensional (2D) gel electrophoresis techniques. The proteins that are on cell surface and/or found secreted in cell culture supernatant are previously stained for the two cell populations using distinct fluorescent probes, or isolated in specifically enriched protein preparations using biotinylation and affinity chromatography (for example, by using Pierce Cell Surface Protein Isolation Kit, Thermo scientific). In parallel, total protein extracts and other internal controls/standards are also prepared for each cell population. The samples are then applied to gels for separating proteins by 2D gel electrophoresis. Bioinformatics and imaging techniques are then used to compare the abundance of cell surface and/or secreted proteins in the gels and the interesting spots (for which a statistically significant difference in abundance is detected between the cell populations) are then picked from the gel and digested using trypsin at the scope of identifying the identity of the protein in such spot by mass spectrometry.

Among the proteins that have been identified as differentially expressed between H2Stem Cells and ADHLSC Cells using such methods, the Sushi domain containing protein 2 (SUSD2) and Fibrinogen Beta chain (FGB) or other coagulation-related secreted proteins have been found strongly expressed in H2Stem Cells when compared to ADHLSC Cells and may thus be of interest as biomarkers (separately or in combination) for H2Stem Cells and H2Stem Progeny.

Even if SUSD2 biological function of SUSD2 has not been fully established so far, the literature provides some relevant information on this cell surface protein having a large extracellular domain. This protein has been identified in many studies comparing gene and/or protein expression and, for instance, has been found over-expressed immediately after a partial hepatectomy (White P et al, 2005). SUSD2 and the corresponding mouse protein (SVS-1) appear affecting activities of cancer cells in vitro or animal models by altering their interaction with extracellular matrix, at least when tested using natural (such as Fibronectin or Galectin-1) or synthetic (such as Matrigel) molecules (Sugahara T et al., 2007; Watson A et al., 2013). Finally, SUSD2 has been identified as containing cell surface epitopes (W5C5, W3D5) that are defined as characterizing mesenchymal stem cells from human bone marrow, endometrium, cartilage, and other tissues (Sivasubramaniyan K et al., 2013; Benz K et al., 2013; Masuda H et al., 2012; Pilz G et al., 2011; Buhring H J et al., 2007).

The initial finding made using 2D gel electrophoresis on the much stronger SUSD2 expression in H2Stem Cells was confirmed using a commercial antibody (purified anti-human SUSD2; Cat. no. 327401, Biolegend) against human SUSD2 in Western blot (FIG. 10A) and in immunofluorescence, using a confocal microscope. SUSD2 extracellular domain may be also present in the cell culture medium as a soluble protein and identified together with secreted proteins (such as FGB, CES1, or alpha-1-antitrypsin and their corresponding activity) that may be used as secreted biomarkers for characterizing H2Stem Cells and specific H2Stem Progeny during their emergence and production, or for identifying features that would suggest specific in vitro and/or in vivo uses.

Interestingly, a few other surface proteins have been characterized as more expressed by ADHLSC Cells than by H2Stem Cells, suggesting an alternative approach for characterizing H2Stem Cells and specific H2Stem Progeny during their emergence and production. For instance, CD140b, often cited amongst the markers characterizing mesenchymal stem cells, appears as having an expression profile opposite from the one of SUSD2 that can be determined by flow cytometry. In fact, such approach may be complementary and combined to Western Blot analysis to show how strongly SUSD2 is expressed in most of H2Stem Cells, and how SUSD2 expression is much lower in a much lower percentage of ADHLSC Cells (FIGS. 10B and C). This combination of biomarker positivity/negative, together with functional features, allows further distinguishing H2Stem Cells from ADHLSC Cells, as well as mesenchymal stem cells previously described (Benz K et al., 2013) that do not present hepatic markers or liver-specific activities.

REFERENCES

Allameh A and Kazemnejad S, Clin Biochem (2012). 45: 385-96.
Azuma H et al., Hepatology (2003). 37: 1385-94.
Baudoin R et al., Xenobiotica (2013). 43:140-52.
Benz K et al., J Transl Med (2013). 11: 27
Bühring H J et al., Ann N Y Acad Sci (2007). 1106:262-71.
Dan Y Y, Methods Mol Biol (2012). 826: 11-23.
Darwiche H and Petersen B E, Prog Mol Biol Transl Sci (2010). 97: 229-49.
Gerets H H et al., Cell Biol Toxicol (2012). 28: 69-87.
Gomez-Lechon M J et al., Methods Mol Biol (2012). 806: 87-97.
Halladay J S et al., J Pharmacol Toxicol Methods (2012). 66: 270-5.
Herrera M B et al., Stem Cells (2006). 24: 2840-50.
Hoffmann S A et al., Biotechnol Bioeng (2012). 109: 3172-81.
Hook L A, Drug Discov Today (2012). 17: 336-42.
Khuu D N et al., Cell Transplant (2011). 20: 287-302.
Lau G and Crichley J, J Pharm Biomed Anal (1994). 12: 1563-72.
Lu Y et al., Biotechnol Bioeng (2012). 109: 595-604.
Lubberstedt M et al., J Pharmacol Toxicol Methods (2011). 63: 59-68.
Massie I et al., Tissue Eng Part C Methods (2011). 17: 765-74.
Masuda H et al., Cell Transplant (2012). 21: 2201-14.
Meng Q, Expert Opin Drug Metab Toxicol (2010). 6: 733-46.
Mitaka T and Ooe H, Drug Metab Rev (2010). 42: 472-81.
Miyazaki M et al., Stem Cells (2007). 25: 2855-63.
Najimi M et al., Cell Transplant (2007). 16: 717-28.
Parveen N et al., Curr Pharm Biotechnol (2011). 12: 226-30.
Pilz G et al., Stem Cells Dev (2011). 20: 635-46.
Russo F P and Parole M, Best Pract Res Clin Gastroenterol (2012). 26: 35-45.
Sahin M B et al., Liver Transpl (2008). 14: 333-45.
Saito R et al., Artif Organs (2011). 35: 80-3.
Saleh F. et al. in "Progenitor Cells" in Meth. Mol. Biol. (2012). 916: 31-45.
Santamaria E et al., Methods Mol Biol (2012). 909: 165-80.
Schmelzer E et al., J Exp Med (2007). 204: 1973-87.
Shiojiri N and Nitou M, Methods Mol Biol (2012). 826: 3-10.
Sivasubramaniyan K et al., Stem Cells Dev (2013). 2: 1944-54.
Slany A et al., J Proteome Res (2010). 9: 6-21.
Smith C M et al., J Pharm Sci (2012). 101: 3989-4002.
Snykers S et al., Stem Cells (2009). 27:577-605.
Sokal E M, Cell Prolif (2011). 44 Suppl 1: 39-43.
Soto-Gutierrez A et al., Cell Transplant (2010). 19: 815-22.
Sugahara T et al., Cancer Sci (2007). 98: 900-8.
Tanaka M and Miyajima A, Methods Mol Biol (2012). 826: 25-32.
Torres D M and Harrison S A, Hepatology (2012). 56: 2013-5.
Tostoes R M et al., Hepatology (2012). 55: 1227-36.
Vanheel A et al., PLoS One (2012). 7: e35544.
Wang C et al., Hepatology (2012). 55: 108-20.
Watson A et al., Mol Cancer Res (2013) 11: 74-85.
White P et al., J Biol Chem (2005). 280: 3715-22.
Wu X et al., PLoS Pathog (2012). 8: e1002617.
Yu J et al., PLoS One (2012). 7: e35230.
Zhu C et al., J Tissue Eng Regen Med (2013). 7: 757-66.

The invention claimed is:

1. An isolated, human adult liver progenitor cell characterized in that said cell is measured positive for expression of:
   (a) at least one hepatic marker selected from the group consisting of albumin, HNF-3B, HNF-4, CYP1A2, CYP2C9, CYP2E1 and CYP3A4;
   (b) at least one mesenchymal marker selected from the group consisting of Vimentin, CD90, CD73, CD44, and CD29;
   (c) at least one liver-specific activity selected from the group consisting of urea secretion, bilirubin conjugation, alpha-1-antitrypsin secretion, and CYP3A4 activity;
   (d) Sushi domain containing protein 2 (SUSD2); and
   (e) Cytokeratin-19 (CK-19);
   wherein said cell is also optionally measured
   (f) negative for one or more markers selected from the group consisting of CD140b, CD45, CD117, CD31, CD133, and CD326;
   (g) positive for Cytokeratin-18 (CK-18) and/or alpha smooth muscle actin (ASMA); and/or
   (h) positive for at least one liver-specific activity selected from the group consisting of sulfotransferase activity, tryptophan-2,3-dioxygenase activity, liver carboxylase activity, ammonia metabolism, and glycogen storage;
   wherein said cell has a cuboidal meso-epithelial morphology.

2. The cell of claim 1 wherein said cell is measured:
   (a) positive for albumin, Vimentin, CD90, CD73, urea secretion, bilirubin conjugation, alpha-1-antitrypsin secretion, CYP3A4 activity, Sushi domain containing protein 2, Cytokeratin-19, and liver carboxylase activity; and
   (b) negative for CD140b.

3. The cell of claim 1 wherein said cell is capable of forming three-dimensional cell clusters in suspension and/or differentiating into cells presenting liver-specific activities.

4. An isolated cell population comprising at least 60%, or between 60% and 99%, or between 70% and 90%, of cells of claim 1.

5. The cell population of claim 4 wherein the population comprises adherent cells or forms three-dimensional cell clusters in suspension, and optionally presents inducible Phase I CYP-dependent activity and uptake of at least one compound selected from the group consisting of Taurocholate, Estrone-3-sulfate, and 1-methyl-4-phenylpyridinium.

6. The cell of claim 1 wherein said cell or a population thereof is modified by means of one or more chemical agents, cell culture medium, growth factors, and/or nucleic acid vectors.

7. A method for obtaining adult liver progenitor cells of human origin as set forth in claim 1, comprising:
   (a) disassociating adult liver or a part thereof to form a population of primary liver cells;
   (b) generating a preparation of the population of primary liver cells of (a);
   (c) culturing cells comprised in the preparation of (b) onto a support that allows adherence and growth of cells thereto and the emergence of a population of cells having cuboidal meso-epithelial morphology;
   (d) passaging the cells of (c) at least once; and
   (e) isolating a population of cells obtained after the passaging of step (d) that maintain a cuboidal meso-epithelial morphology, that are positive for at least one hepatic marker and at least one mesenchymal marker, and that have at least one liver-specific activity, wherein (f) the cells of step (c) and/or the cell population of step (e) are measured positive for cytokeratin 19, albumin, alpha-1-antitrypsin secretion, Sushi domain containing protein 2, and CYP3A4.

8. The method of claim 7 wherein the cells of step (c) and/or the cell population of step (e) are further measured positive for Cytokeratin-18 (CK-18) and/or alpha smooth muscle actin (ASMA) and are measured negative for CD140b.

9. The method of claim 7 wherein the cell population of step (e) is maintained in cell culture conditions that allow formation of three-dimensional cell clusters in suspension.

10. A composition comprising the cell of claim 1 or a population thereof.

11. A method for treating a liver disease in a subject in need thereof, the method comprising administering a therapeutically effective amount of the cells of claim 1, or a population or composition thereof, to the subject.

12. The method of claim 11 wherein the liver disease is an inborn error of liver metabolism, an inherited Blood Coagulation Disorder, progressive familial intrahepatic cholestasis type 1/2/3, alpha 1-Antitrypsin Deficiency, defect of liver cell transporters, Porphyria, fatty liver or fibrotic liver disease, primary biliary cirrhosis, sclerosing cholangitis, liver degenerative disease, or acute or chronic liver failure.

13. A kit comprising a cell of claim 1 or a population or composition thereof.

14. The kit of claim 13 wherein said kit further comprises one or more vials containing said cell, said cell population, or said composition, and one or more of the following elements: devices, disposable materials, solutions, chemical products, biological products, and/or instructions for using elements of said kit.

* * * * *